US008137962B2

(12) United States Patent
Flotte et al.

(10) Patent No.: US 8,137,962 B2

(45) Date of Patent: Mar. 20, 2012

(54) COMPOSITIONS FOR TREATING CYSTIC FIBROSIS

(75) Inventors: Terence R. Flotte, Alachua, FL (US); Jeffrey R. Sirninger, Gainesville, FL (US); William B. Guggino, Baltimore, MD (US); Liudmila Cebotaru, Baltimore, MD (US); Christian Müller, Gainesville, FL (US)

(73) Assignees: University of Florida Research Foundation, Gainesville, FL (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 11/713,291

(22) Filed: Mar. 2, 2007

(65) Prior Publication Data

US 2008/0003204 A1 Jan. 3, 2008

Related U.S. Application Data

(63) Continuation-in-part of application No. PCT/US2005/031576, filed on Sep. 2, 2005.

(60) Provisional application No. 60/607,324, filed on Sep. 3, 2004.

(51) Int. Cl.
*C12N 15/00* (2006.01)
*A61K 48/00* (2006.01)

(52) U.S. Cl. .................................... 435/320.1; 424/93.2

(58) Field of Classification Search ............... 435/320.1, 435/93.2, 320, 91.33; 514/44 R
See application file for complete search history.

(56) References Cited

U.S. PATENT DOCUMENTS 5,990,279 A * 11/1999 Carter et al. .................. 530/350
7,056,502 B2 6/2006 Hildinger et al.

FOREIGN PATENT DOCUMENTS

WO WO 99/43789 * 9/1999
WO WO/01/83692 * 8/2001

OTHER PUBLICATIONS

Auricchio et al Journal of Clinical Invest. 2002; 110(4): 499-504.*

Carroll et al The Journal of Biological Chemistry, 1995, 270, 20, 11941-11946).*

Sirninger et al Hum Gene Ther. Sep. 1, 2004; 15(9):832-41.*

International Preliminary Report on Patentability; Written Opinion of the International Searching Authority, Sep. 15, 2006.

Auricchio A et al. "Noninvasive gene transfer to the lung for systemic delivery of therapeutic proteins." J Clin Invest. Aug. 2002;110(4):499-504.

Beck Se et al. "Repeated delivery of adeno-associated virus vectors to the rabbit airway." J Virol. Nov. 1999;73(1 1):9446-55.

Koehler Dr et al. "Protection of Cftr knockout mice from acute lung infection by a helper-dependent adenoviral vector expressing Cftr in airway epithelia." Proc Natl Acad Sci U S A. Dec. 23, 2003;100(26):15364-9.

Moss Rb et al. "Repeated adeno-associated virus serotype 2 aerosol-mediated cystic fibrosis transmembrane regulator gene transfer to the lungs of patients with cystic fibrosis: a multicenter, double-blind, placebo-controlled trial." Chest. Feb. 2004;125(2):509-21.

Zolotukhin S et al. "Production and purification of serotype 1, 2, and 5 recombinant adeno-associated viral vectors." Methods. Oct. 2002;28(2):158-67.

International Search Report for International Application No. PCT/US2005/31576, issued Jun. 23, 2006 and mailed Sep. 15, 2006.

* cited by examiner

*Primary Examiner* — Anoop Singh

(74) *Attorney, Agent, or Firm* — Edwards Wildman Palmer LLP; Peter F. Corless; Andrew W. Shyjan, Esq.

(57) ABSTRACT

The invention relates to compositions and methods of treating cystic fibrosis. More specifically, this invention relates to the use the AAV vectors and constructs to provide gene therapy to cystic fibrosis patients.

4 Claims, 28 Drawing Sheets

```
  1 ttggccactc cctctctgcg cgctcgctcg ctcactgagg ccgggcgacc aaaggtcgcc
 61 cgacgcccgg gctttgcccg ggcggcctca gtgagcgagc gagcgcgcag agagggagtg
121 gccaactcca tcactagggg ttcctagatc tgaattcggt accctagtta ttaatagtaa
```

```
 181 tcaattacgg ggtcattagt tcatagccca tatatggagt tccgcgttac ataacttacg
 241 gtaaatggcc cgcctggctg accgcccaac gacccccgcc cattgacgtc aataatgacg
 301 tatgttccca tagtaacgcc aatagggact ttccattgac gtcaatgggt ggactattta
 361 cggtaaactg cccacttggc agtacatcaa gtgtatcata tgccaagtac gcccccctatt
 421 gacgtcaatg acggtaaatg gcccgcctgg cattatgccc agtacatgac cttatgggac
 481 tttcctactt ggcagtacat ctacgtatta gtcatcgcta ttaccatggt cgaggtgagc
 541 cccacgttct gcttcactct ccccatctcc ccccctccc cacccccaat tttgtattta
 601 tttatttttt aattattttg tgcagcgatg ggggcggggg gggggggggg gcgcgcgcca
 661 ggcggggcgg ggcggggcga ggggcggggc ggggcgaggc ggagaggtgc ggcggcagcc
 721 aatcagagcg gcgcgctccg aaagtttcct tttatggcga ggcggcggcg gcggcggccc
 781 tataaaaagc gaagcgcgcg gcgggcggga gtcgctgcga cgctgccttc gccccgtgcc
 841 ccgctccgcc gccgcctcgc gccgcccgcc ccggctctga ctgaccgcgt tactcccaca
 901 ggtgagcggg cgggacggcc cttctcctcc gggctgtaat tagcgcttgg tttaatgacg
 961 gcttgtttct tttctgtggc tgcgtgaaag ccttgagggg ctccgggagc tagagcctct
1021 gctaaccatg ttcatgcctt cttctttttc ctacagctcc tgggcaacgt gctggttatt
1081 gtgctgtctc atcattttgg caaagaattc ctcgaagatc cgaaggggtt caagcttaaa
1141 aactagtgcc gccaccatga tcgagaacat ccaatctgtt aaggcatact gctgggaaga
1201 agcaatggaa aaaatgattg aaaacttaag acaaacagaa ctgaaactga ctcggaaggc
1261 agcctatgtg agatacttca atagctcagc cttcttcttc tcagggttct ttgtggtgtt
1321 tttatctgtg cttccctatg cactaatcaa aggaatcatc ctccggaaaa tattcaccac
1381 catctcattc tgcattgttc tgcgcatggc ggtcactcgg caatttccct gggctgtaca
1441 aacatggtat gactctcttg gagcaataaa caaaatacag gatttcttac aaaagcaaga
1501 atataagaca ttggaatata acttaacgac tacagaagta gtgatggaga atgtaacagc
1561 cttctgggag gagggatttg gggaattatt tgagaaagca aaacaaaaca ataacaatag
1621 aaaaacttct aatggtgatg acagcctctt cttcagtaat ttctcacttc ttggtactcc
1681 tgtcctgaaa gatattaatt tcaagataga aagaggacag ttgttggcgg ttgctggatc
```

FIG. 12B

```
1741 cactggagca ggcaagactt cacttctaat gatgattatg ggagaactgg agccttcaga
1801 gggtaaaatt aagcacagtg gaagaatttc attctgttct cagttttcct ggattatgcc
1861 tggcaccatt aaagaaaata tcatctttgg tgtttcctat gatgaatata gatacagaag
1921 cgtcatcaaa gcatgccaac tagaagagga catctccaag tttgcagaga aagacaatat
1981 agttcttgga gaaggtggaa tcacactgag tggaggtcaa cgagcaagaa tttctttagc
2041 aagagcagta tacaaagatg ctgatttgta tttattagac tctccttttg gatacctaga
2101 tgttttaaca gaaaaagaaa tatttgaaag ctgtgtctgt aaactgatgg ctaacaaaac
2161 taggattttg gtcacttcta aaatggaaca tttaaagaaa gctgacaaaa tattaatttt
2221 gcatgaaggt agcagctatt tttatgggac attttcagaa ctccaaaatc tacagccaga
2281 ctttagctca aaactcatgg gatgtgattc tttcgaccaa tttagtgcag aaagaagaaa
2341 ttcaatccta actgagacct tacaccgttt ctcattagaa ggagatgctc ctgtctcctg
2401 gacagaaaca aaaaaacaat cttttaaaca gactggagag tttggggaaa aaaggaagaa
2461 ttctattctc aatccaatca actctatacg aaaattttcc attgtgcaaa agactccctt
2521 acaaatgaat ggcatcgaag aggattctga tgagccttta gagagaaggc tgtccttagt
2581 accagattct gagcagggag aggcgatact gcctcgcatc agcgtgatca gcactggccc
2641 cacgcttcag gcacgaagga ggcagtctgt cctgaacctg atgacacact cagttaacca
2701 aggtcagaac attcaccgaa agacaacagc atccacagga aaagtgtcac tggcccctca
2761 ggcaaacttg actgaactgg atatatattc aagaaggtta tctcaagaaa ctggcttgga
2821 aataagtgaa gaaattaacg aagaagactt aaaggagtgc ctttttgatg atatggagag
2881 cataccagca gtgactacat ggaacacata ccttcgatat attactgtcc acaagagctt
2941 aatttttgtg ctaatttggt gcttagtaat tttctggca gaggtggctg cttctttggt
3001 tgtgctgtgg ctccttggaa acactcctct tcaagacaaa gggaatagta ctcatagtag
3061 aaataacagc tatgcagtga ttatcaccag caccagttcg tattatgtgt tttacattta
3121 cgtgggagta gccgacactt tgcttgctat gggattcttc agaggtctac cactggtgca
3181 tactctaatc acagtgtcga aaattttaca ccacaaaatg ttacattctg ttcttcaagc
3241 acctatgtca accctcaaca cgttgaaagc aggtgggatt cttaatagat tctccaaaga
```

FIG. 12C

```
3301 tatagcaatt ttggatgacc ttctgcctct taccatattt gacttcatcc agttgttatt
3361 aattgtgatt ggagctatag cagttgtcgc agttttacaa ccctacatct ttgttgcaac
3421 agtgccagtg atagtggctt ttattatgtt gagagcatat ttcctccaaa cctcacagca
3481 actcaaacaa ctggaatctg aaggcaggag tccaattttc actcatcttg ttacaagctt
3541 aaaaggacta tggacacttc gtgccttcgg acggcagcct tactttgaaa ctctgttcca
3601 caaagctctg aatttacata ctgccaactg gttcttgtac ctgtcaacac tgcgctggtt
3661 ccaaatgaga atagaaatga tttttgtcat cttcttcatt gctgttacct tcatttccat
3721 tttaacaaca ggagaaggag aaggaagagt tggtattatc ctgactttag ccatgaatat
3781 catgagtaca ttgcagtggg ctgtaaactc cagcatagat gtggatagct tgatgcgatc
3841 tgtgagccga gtctttaagt tcattgacat gccaacagaa ggtaaaccta ccaagtcaac
3901 caaaccatac aagaatggcc aactctcgaa agttatgatt attgagaatt cacacgtgaa
3961 gaaagatgac atctggccct caggggccca aatgactgtc aaagatctca cagcaaaata
4021 cacagaaggt ggaaatgcca tattagagaa catttccttc tcaataagtc ctggccagag
4081 ggtgggcctc ttgggaagaa ctggatcagg gaagagtact ttgttatcag ctttttgag
4141 actactgaac actgaaggag aaatccagat cgatggtgtg tcttgggatt caataacttt
4201 gcaacagtgg aggaaagcct ttggagtgat accacagaaa gtatttattt tttctggaac
4261 atttagaaaa aacttggatc cctatgaaca gtggagtgat caagaaatat ggaaagttgc
4321 agatgaggtt gggctcagat ctgtgataga acagtttcct gggaagcttg actttgtcct
4381 tgtggatggg ggctgtgtcc taagccatgg ccacaagcag ttgatgtgct tggctagatc
4441 tgttctcagt aaggcgaaga tcttgctgct tgatgaaccc agtgctcatt tggatccagt
4501 aacataccaa ataattagaa gaactctaaa acaagcattt gctgattgca cagtaattct
4561 ctgtgaacac aggatagaag caatgctgga atgccaacaa tttttggtca tagaagagaa
4621 caaagtgcgg cagtacgatt ccatccagaa actgctgaac gagaggagcc tcttccggca
4681 agccatcagc ccctccgaca gggtgaagct ctttccccac cggaactcaa gcaagtgcaa
4741 gtctaagccc cagattgctg ctctgaaaga ggagacagaa gaagaggtgc aagatacaag
4801 gctttagaga gcagcataaa tgttgacatg ggacatttgc tcatggaatt ggcaggccta
```

FIG. 12D

```
4861 ataaagagct cagatgcatc gatcagagtg tgttggtttt ttgtgtgtac tgaggaaccc
4921 ctagtgatgg agttggccac tccctctctg cgcgctcgct cgctcactga ggccgcccgg
4981 gcaaagcccg ggcgtcgggc gacctttggt cgcccggcct cagtgagcga gcgagcgcgc
5041 agagagggag tggccaaccc cccccccccc ccccctgcag cccagctgca ttaatgaatc
5101 ggccaacgcg cggggagagg cggtttgcgt attgggcgct cttccgcttc ctcgctcact
5161 gactcgctgc gctcggtcgt tcggctgcgg cgagcggtat cagctcactc aaaggcggta
5221 atacggttat ccacagaatc aggggataac gcaggaaaga acatgtgagc aaaaggccag
5281 caaaaggcca ggaaccgtaa aaaggccgcg ttgctggcgt ttttccatag gctccgcccc
5341 cctgacgagc atcacaaaaa tcgacgctca agtcagaggt ggcgaaaccc gacaggacta
5401 taaagatacc aggcgtttcc ccctggaagc tccctcgtgc gctctcctgt tccgaccctg
5461 ccgcttaccg gatacctgtc cgcctttctc ccttcgggaa gcgtggcgct ttctcaatgc
5521 tcacgctgta ggtatctcag ttcggtgtag gtcgttcgct ccaagctggg ctgtgtgcac
5581 gaaccccccg ttcagcccga ccgctgcgcc ttatccggta actatcgtct tgagtccaac
5641 ccggtaagac acgacttatc gccactggca gcagccactg gtaacaggat tagcagagcg
5701 aggtatgtag gcggtgctac agagttcttg aagtggtggc ctaactacgg ctacactaga
5761 aggacagtat ttggtatctg cgctctgctg aagccagtta ccttcggaaa aagagttggt
5821 agctcttgat ccggcaaaca aaccaccgct ggtagcggtg gtttttttgt ttgcaagcag
5881 cagattacgc gcagaaaaaa aggatctcaa gaagatcctt tgatcttttc tacggggtct
5941 gacgctcagt ggaacgaaaa ctcacgttaa gggattttgg tcatgagatt atcaaaaagg
6001 atcttcacct agatcctttt aaattaaaaa tgaagtttta aatcaatcta aagtatatat
6061 gagtaaactt ggtctgacag ttaccaatgc ttaatcagtg aggcacctat ctcagcgatc
6121 tgtctatttc gttcatccat agttgcctga ctccccgtcg tgtagataac tacgatacgg
6181 gagggcttac catctggccc cagtgctgca atgataccgc gagacccacg ctcaccggct
6241 ccagatttat cagcaataaa ccagccagcc ggaagggccg agcgcagaag tggtcctgca
6301 actttatccg cctccatcca gtctattaat tgttgccggg aagctagagt aagtagttcg
6361 ccagttaata gtttgcgcaa cgttgttgcc attgctacag gcatcgtggt gtcacgctcg
```

FIG. 12E

```
6421 tcgtttggta tggcttcatt cagctccggt tcccaacgat caaggcgagt tacatgatcc
6481 cccatgttgt gcaaaaaagc ggttagctcc ttcggtcctc cgatcgttgt cagaagtaag
6541 ttggccgcag tgttatcact catggttatg gcagcactgc ataattctct tactgtcatg
6601 ccatccgtaa gatgcttttc tgtgactggt gagtactcaa ccaagtcatt ctgagaatag
6661 tgtatgcggc gaccgagttg ctcttgcccg gcgtcaatac gggataatac cgcgccacat
6721 agcagaactt taaaagtgct catcattgga aaacgttctt cggggcgaaa actctcaagg
6781 atcttaccgc tgttgagatc cagttcgatg taacccactc gtgcacccaa ctgatcttca
6841 gcatctttta ctttcaccag cgtttctggg tgagcaaaaa caggaaggca aaatgccgca
6901 aaaaagggaa taagggcgac acggaaatgt tgaatactca tactcttcct ttttcaatat
6961 tattgaagca tttatcaggg ttattgtctc atgagcggat acatatttga atgtatttag
7021 aaaaataaac aaataggggt tccgcgcaca tttccccgaa aagtgccacc tgacgtctaa
7081 gaaaccatta ttatcatgac attaacctat aaaaataggc gtatcacgag gccctttcgt
7141 ctcgcgcgtt tcggtgatga cggtgaaaac ctctgacaca tgcagctccc ggagacggtc
7201 acagcttgtc tgtaagcgga tgccgggagc agacaagccc gtcagggcgc gtcagcgggt
7261 gttggcgggt gtcggggctg gcttaactat gcggcatcag agcagattgt actgagagtg
7321 caccatatgc ggtgtgaaat accgcacaga tgcgtaagga gaaaataccg catcaggaaa
7381 ttgtaaacgt taatattttg ttaaaattcg cgttaaattt ttgttaaatc agctcatttt
7441 ttaaccaata ggccgaaatc ggcaaaatcc cttataaatc aaaagaatag accgagatag
7501 ggttgagtgt tgttccagtt tggaacaaga gtccactatt aaagaacgtg gactccaacg
7561 tcaaagggcg aaaaaccgtc tatcagggcg atggcccact acgtgaacca tcaccctaat
7621 caagtttttt ggggtcgagg tgccgtaaag cactaaatcg gaaccctaaa gggagccccc
7681 gatttagagc ttgacgggga aagccggcga acgtggcgag aaaggaaggg aagaaagcga
7741 aaggagcggg cgctagggcg ctggcaagtg tagcggtcac gctgcgcgta accaccacac
7801 ccgccgcgct taatgcgccg ctacagggcg cgtcgcgcca ttcgccattc aggctacgca
7861 actgttggga agggcgatcg gtgcgggcct cttcgctatt acgccagctg gctgcagggg
7921 gggggggggg gggg
```

FIG. 12F

COMPOSITIONS FOR TREATING CYSTIC FIBROSIS

RELATED APPLICATIONS

The application is a continuation-in-part of, and claims the benefit of priority of International Application PCT/US2005/031576, filed Sep. 2, 2005, which claims priority to U.S. Provisional Application No. 60/607,324, entitled "Compositions And Methods For Treating Cystic Fibrosis," filed Sep. 3, 2004, both of which are hereby incorporated by reference in their entireties.

GOVERNMENT SUPPORT

It is acknowledged that the U.S. Government has certain rights in the invention described herein, which was made in part with funds from the National Institute of Health, Grant Nos. HL51811, HL67260, NIH PO1 HL51811-06, NHLBI P01, NIDDK R01 and DK51809.

BACKGROUND OF THE INVENTION

Cystic Fibrosis (CF) is caused by a defect in a single gene within the DNA that codes' for a protein called the cystic fibrosis transmembrane conductance regulator (CFTR). This protein acts as a channel to allow salt to get across (trans-), cell membranes; i.e., to conduct sodium and chloride in and out of the cell. The CFTR protein also regulates the function of other membrane salt channels, and so a defect in this gene can have a large impact on the salt concentration in body fluids. Fluids made in a variety of organs are affected, including the lung, pancreas, liver, and sexual organs, but pathology of the airways within the lung is responsible for most of the life threatening problems in CF patients (>90%). Problems with the salt concentration in airway fluids, and abnormalities in protein processing, as well as cytokine production, lead to an increased frequency, duration, and severity of lung infections. The body's own defending immune cells try to eliminate these infections, but in the long term end up secondarily damaging the surrounding lung tissue. This results in severe progressive destruction of the lungs, which the body tries to heal by scarring (fibrosis). This self-destructive process ends up leaving hardened, scarred non-functional lung tissue that contains fluid filled sacs (cysts).

There is currently no cure for CF and thus there is a need in the art to provide a treatment for CF that may slow or even stop the progression of the disease in children before their lungs become severely damaged.

BRIEF SUMMARY OF THE INVENTION

According to one aspect, an AAV gene therapy particle comprises an AAV capsid protein from AAV and a sequence encoding a cystic fibrosis gene or a portion thereof.

In certain preferred embodiments, the AAV capsid protein is selected from AAV2, AAV3, AAV4, AAV5, and AAV6. In a particularly preferred embodiment the capsid protein is an AAV5 capsid protein.

According to another aspect, a pharmaceutical composition comprises an AAV gene therapy particle and a biocompatible pharmaceutical carrier.

According to yet another aspect, a method of gene therapy for the treatment of a subject having a mutation in the CFTR gene comprises administering a therapeutically effective amount of a gene therapy particle to the cells of a subject.

In another aspect, a method of treating cystic fibrosis comprises administering to a subject in need thereof a therapeutically effective amount of an AAV gene therapy particle.

In another aspect, the invention provides a method of treating airway inflammation, i.e., airway inflammation caused by allergic bronchopulmonary aspergillosis, in a subject having a mutation in the CFTR gene by administering to a subject in need thereof a therapeutically effective amount of an AAV gene therapy particle.

In another aspect, the invention provides a method of treating aberrant epithelial cytokine signaling in a subject having a mutation in the CFTR gene, by administering to a subject in need thereof a therapeutically effective amount of an AAV gene therapy particle.

In another aspect, the invention provides a method of decreasing IgE levels in a subject having a mutation in the CFTR gene, by administering to a subject in need thereof a therapeutically effective amount of an AAV gene therapy particle.

In one aspect, a method of reducing or eliminating cystic fibrosis symptoms comprises administering to a subject in need thereof a therapeutically effective amount of an AAV gene therapy particle.

Another aspect of the invention is a recombinant adenoviral associated virus (rAAV) gene therapy particle comprising an AAV5 capsid protein and a DNA sequence encoding a CFTR protein or a biologically active portion thereof operatively linked to a promoter, and further comprising a first and a second AAV inverted terminal repeat (ITR) sequence flanking the sequence encoding the CFTR protein or portion thereof. Some embodiments of the gene therapy particle express a biologically active truncated CFTR protein lacking amino acids 1-264 or amino acids 27-264 of the human CFTR protein sequence.

Some embodiments of the rAAV gene therapy particle are optimized for high levels of expression of the CRTR protein and comprise a chicken beta actin (CB) promoter or a cytomegalovirus enhancer/chicken beta-actin promoter.

Certain preferred rAAV gene therapy particles of the invention are pseudotyped rAAV vectors, wherein the ITR nucleotide sequences are derived from AAV serotype 2 (AAV-2) and at least one capsid protein is derived from AAV serotype 5 (AAV-5).

Certain rAAV gene therapy particles in accordance with the present invention comprise the DNA sequence represented by SEQ ID NO: 1 or SEQ ID NO:8.

Yet another aspect of the invention is a method of gene therapy for the treatment of a subject having a mutation in the CFTR gene comprising administering a therapeutically effective amount of a recombinant adenoviral associated virus (rAAV) gene therapy particle to cells of the subject, wherein the gene therapy particle comprises an AAV5 capsid protein and a DNA sequence encoding a CFTR protein or a biologically active portion thereof operatively linked to a promoter, and further comprises a first and a second AAV inverted terminal repeat (ITR) sequence flanking the sequence encoding the CFTR protein or portion thereof.

The method may be practiced using any of the above described rAAV gene therapy particles.

Other embodiments of the invention are disclosed infra.

Figure 2:
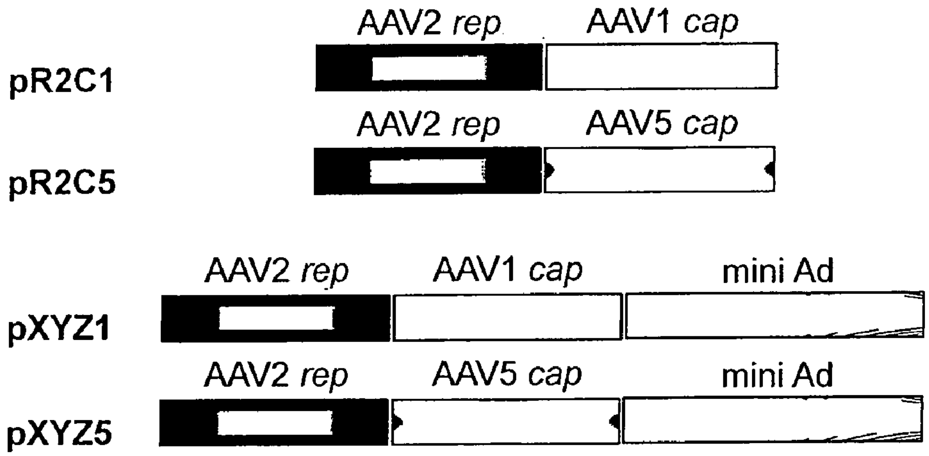

FIG. 2 is a diagram of AAV serotype helper plasmids. Plasmid pR2C1 is a hybrid helper plasmid containing an open reading frame (ORF) coding for AAV2 rep genes derived from the plasmid pACG2, linked to an ORF coding for AAV1 cap genes, amplified by a PCR-mediated protocol from wt AAV1 DNA. Plasmid pR2C5 contains the same rep gene ORF as in pR2C1, linked to the ORF coding for AAV5 cap genes, derived from pAAV5-2. Plasmids pXYZ1 and pXYZ5 contain rep2cap1 and rep2cap5 helper cassettes respectively, inserted into pXYZ background. Plasmid pXYZ is a mini Ad plasmid helper constructed from plasmid pAdEasy, which contains E2A, E4, and VA genes of Ad5.

Figure 3:
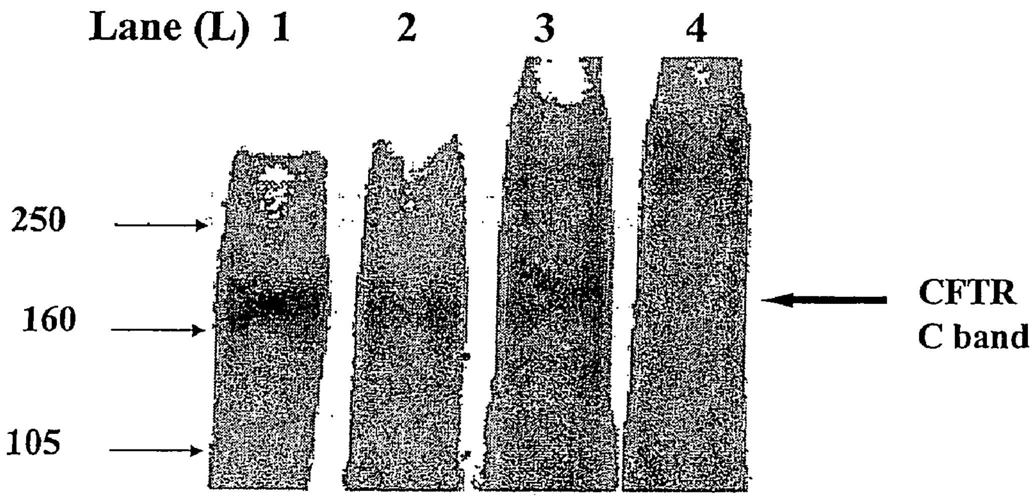

FIG. 3 depicts CFTR expression as assessed by in vitro phosphorylation. Cell lysates from 16HBE cells (0.6 mg (lane 1, L1) and 0.3 mg (L2)); rabbit ileum (2.5 mg (L3)); and monkey lung (L4) were immunoprecipitated by 2 mg μg monoclonal antibody M3A7. Immunoprecipitates were then phosphorylated in vitro by the addition of the catalytic subunit of protein kinase A and $^{32}$P-ATP. CFTR was not detectable in the control monkey because the level of expression was low.

Figure 4:
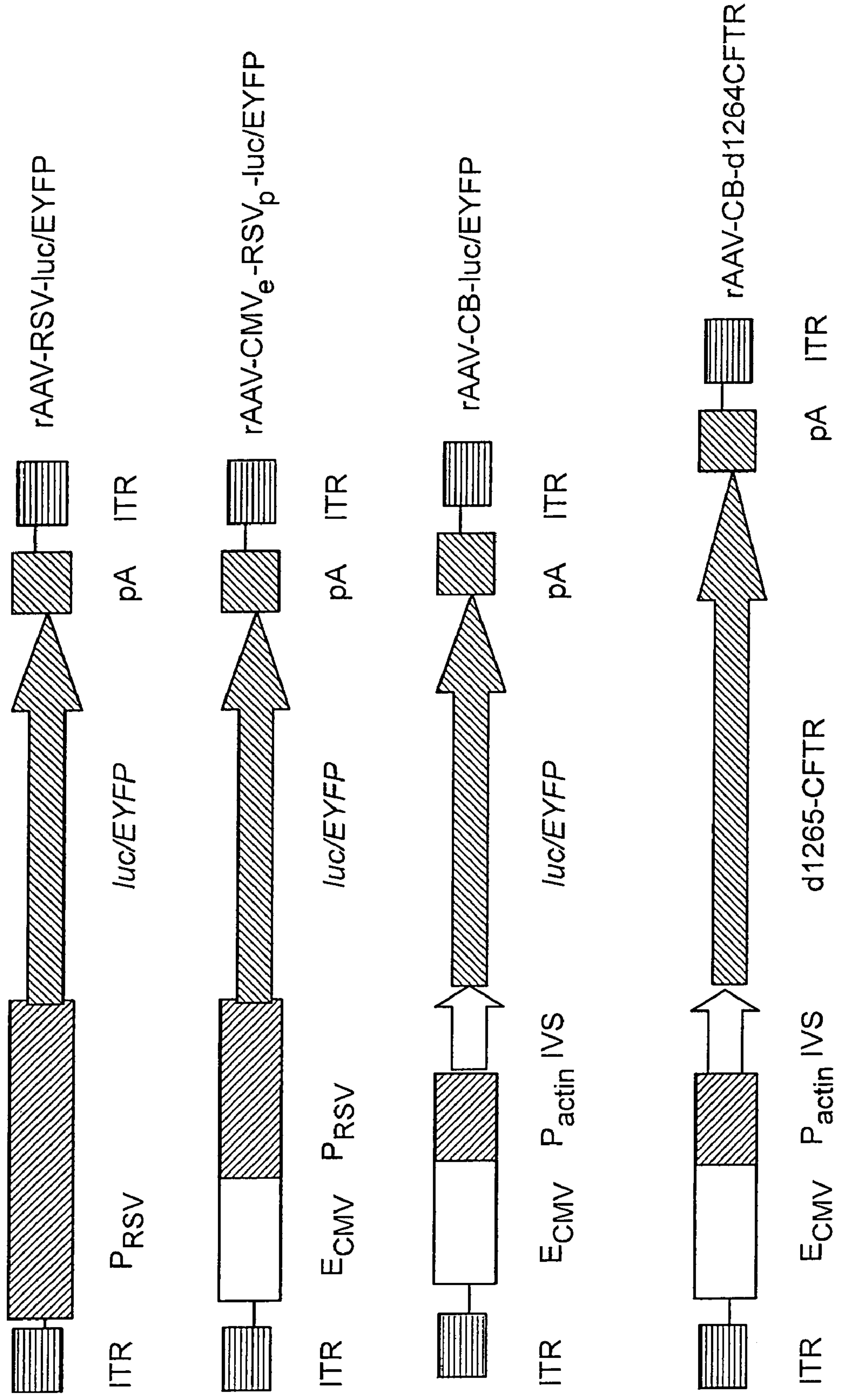

FIG. 4 is a diagram showing structures of rAAV plasmids. The structures of the plasmid constructs used for transient transfection and vector transduction are shown. ITR=AAV2 inverted terminal repeat; $P_{RSV}$=Rous Sarcoma Virus LTR promoter; luc/EYFP=luciferase-enhanced yellow fluorescent protein translational fusion protein; pA=synthetic polyadenylation signal; $E_{CMV}$=Human cytomegalovirus immediate early enhancer; $P_{actin}$=chicken beta actin promoter; IVS=hybrid chicken beta actin/rabbit beta globin intron; Δ264CFTR=version of CFTR coding sequence deleted for the first 264 amino acids.

Figure 5:
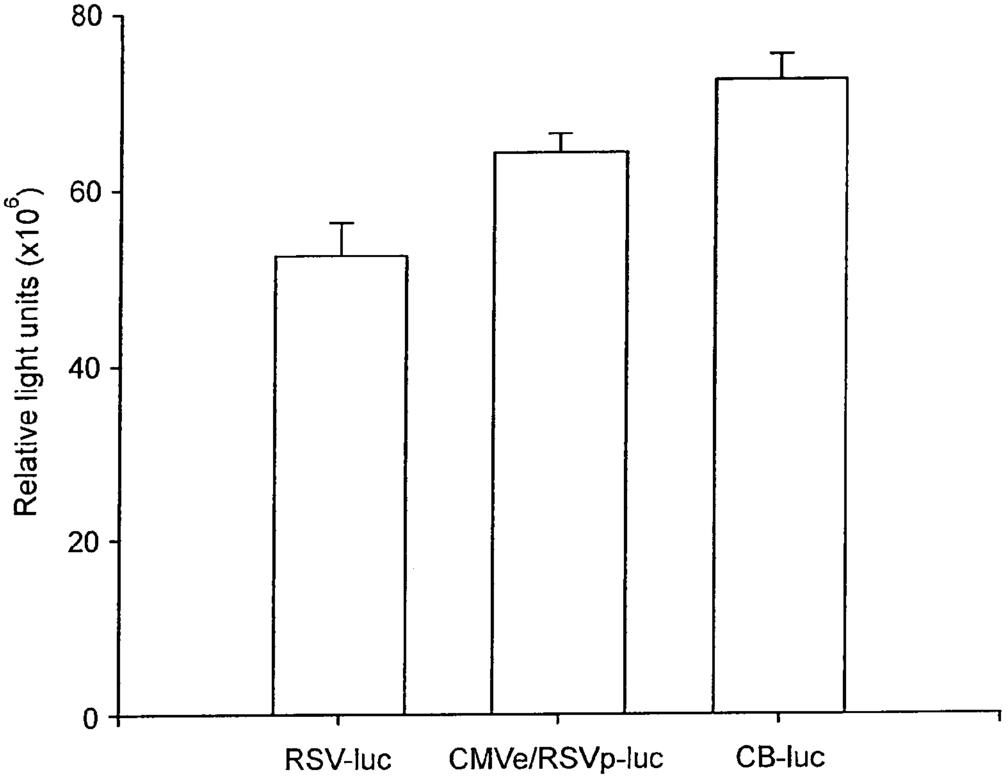

FIG. 5 depicts in vitro comparison of promoter efficacy in a CF bronchial epithelial cell line. Matched cultures of IB3-1 cells (CF bronchial epithelial cell line) were transfected with each of the indicated constructs, and luciferase expression was measured. N=4 for each construct. Results are shown as mean ±standard error.

Figure 6A:
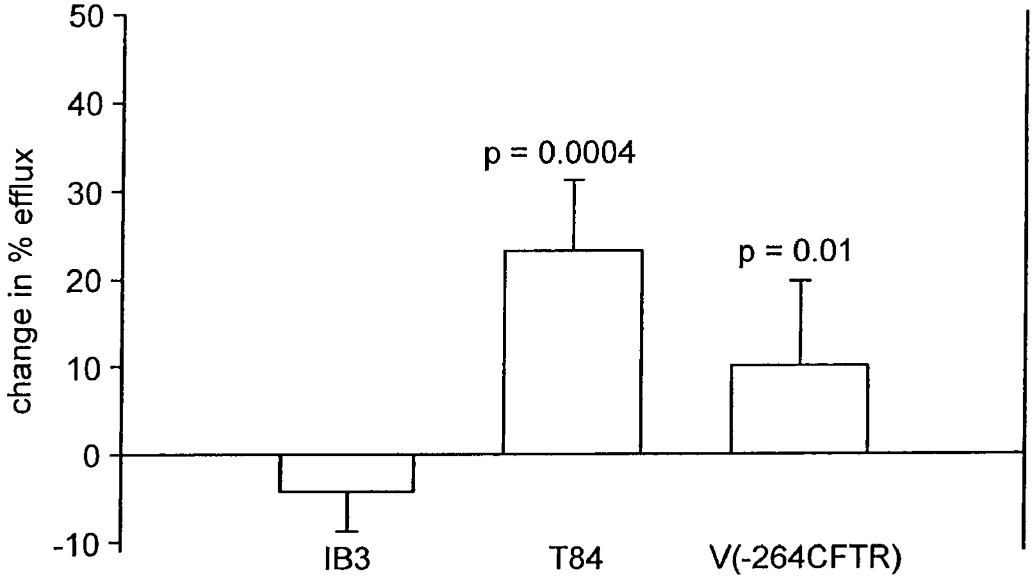
Figure 6B:
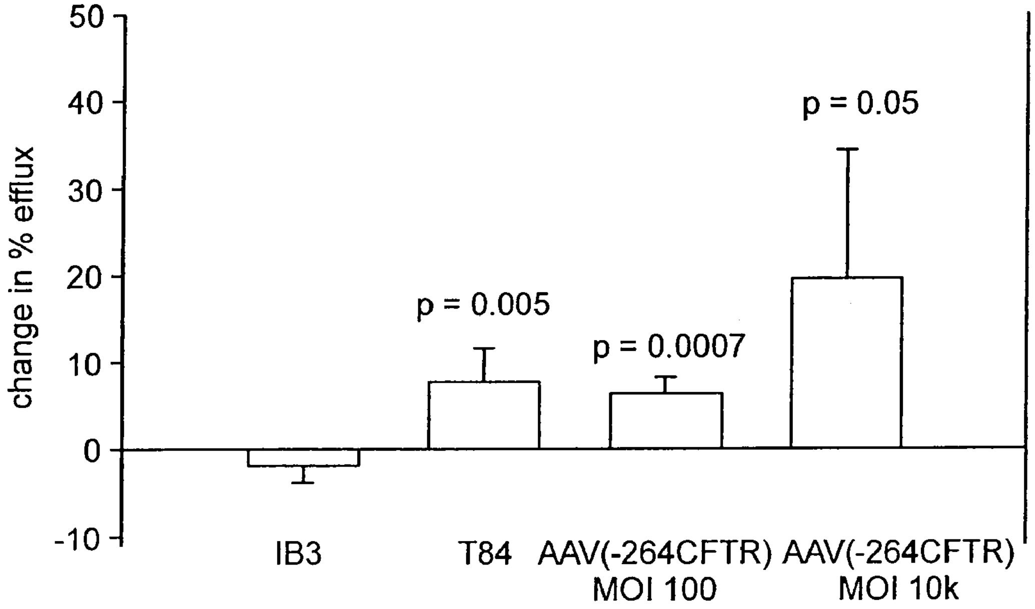

FIG. 6 depicts the results of an isotope tracer ($^{36}Cl^-$) efflux assay to detect functional CFTR expression in transfected or transduced IB3-1 cells. FIG. 6A shows cultures of CF bronchial epithelial IB3-1 cells (negative control), T84 cells (positive control), or pAAV-CB-Δ264CFTR-transfected IB3-1 cells loaded with $^{36}Cl^-$ and then monitored for isotope efflux before and after addition of a CFTR-specific cAMP-agonist cocktail. The percent increase in efflux after addition of agonist is depicted. N=6 for each condition. P values are vs. IB3-1. FIG. 6B depicts similar cAMP-stimulated chloride efflux values in IB3-1 cells transduced with packaged rAAV-CB-Δ264CFTR virions or particles, at particle multiplicities of 100 or 10,000 vector genome particles per cell. N=6 for each, P values are vs. IB3-1.

Figure 7A:
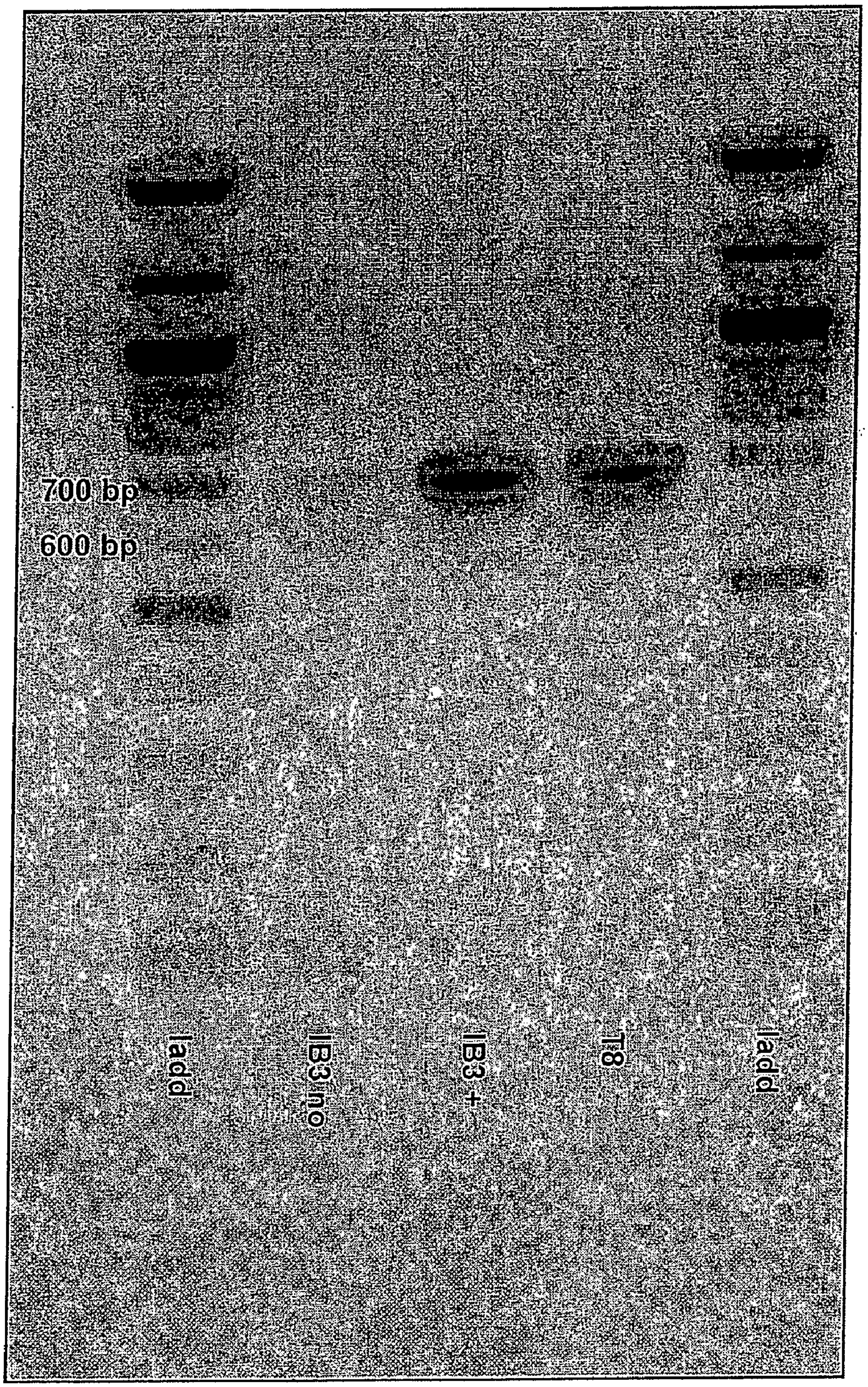
Figure 7B:
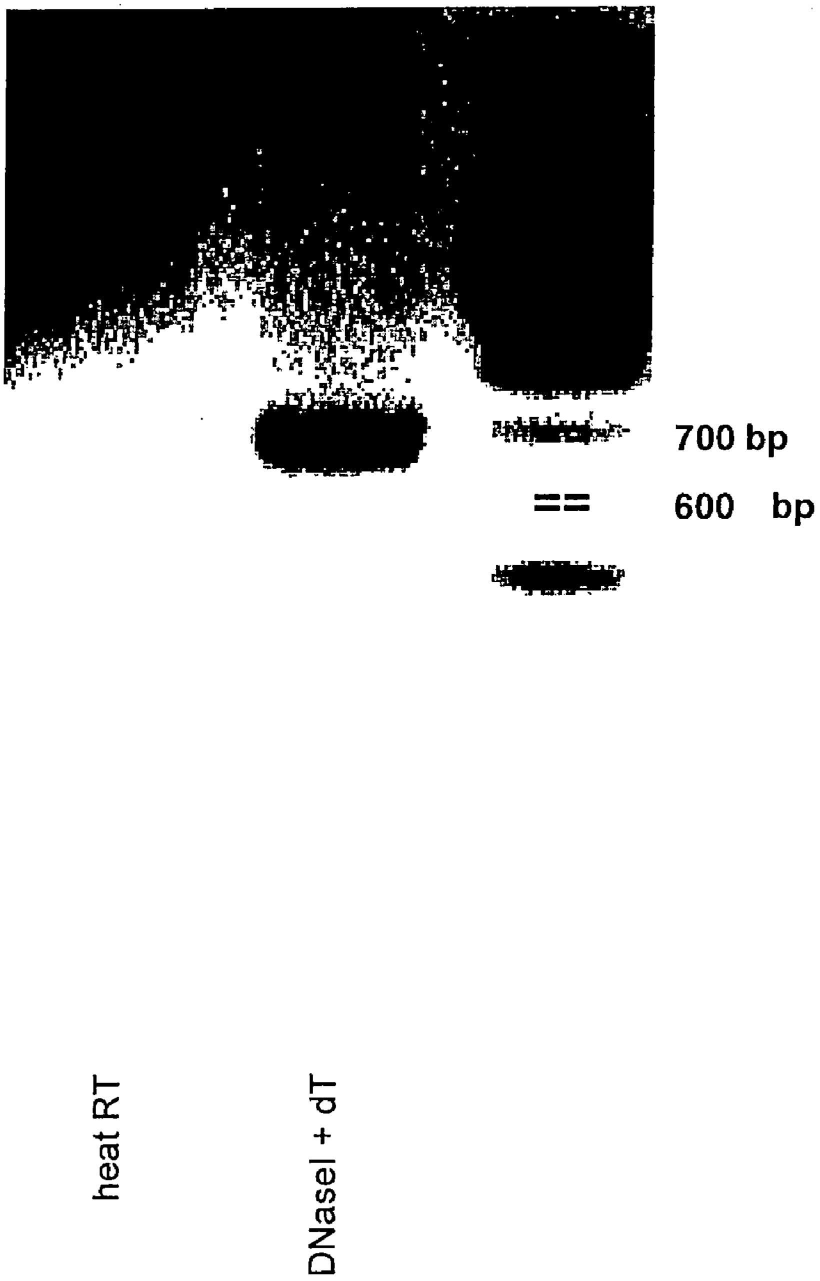

FIG. 7 depicts the results of reverse transcriptase (RT)-PCR to detect vector-derived CFTR mRNA after transduction of IB3-1 cells with rAAV-CB-Δ264CFTR. FIG. 7A shows negative images of ethidium bromide stained agarose gels showing an RT-PCR product of the predicted size. A low baseline level of mRNA in untransduced IB3-1 cells is as previously observed with this cell line. FIG. 7B demonstrates that the band is not present without active RT, thus ruling out the possibility of DNA contamination of these DNase-treated, dT-column purified RNA extracts.

FIG. 8A-D depicts results of excised, inside-out patch clamp analysis of IB3-1 cells transfected either with full length CFTR (8A, 8B) or the pAAV-CB-Δ264CFTR construct (8C, 8D). In the current vs. time plots (8B and 8D), channel openings appear as step-like downward deflections in the panels after application of a CFTR-specific cAMP agonist cocktail.

Figure 9:
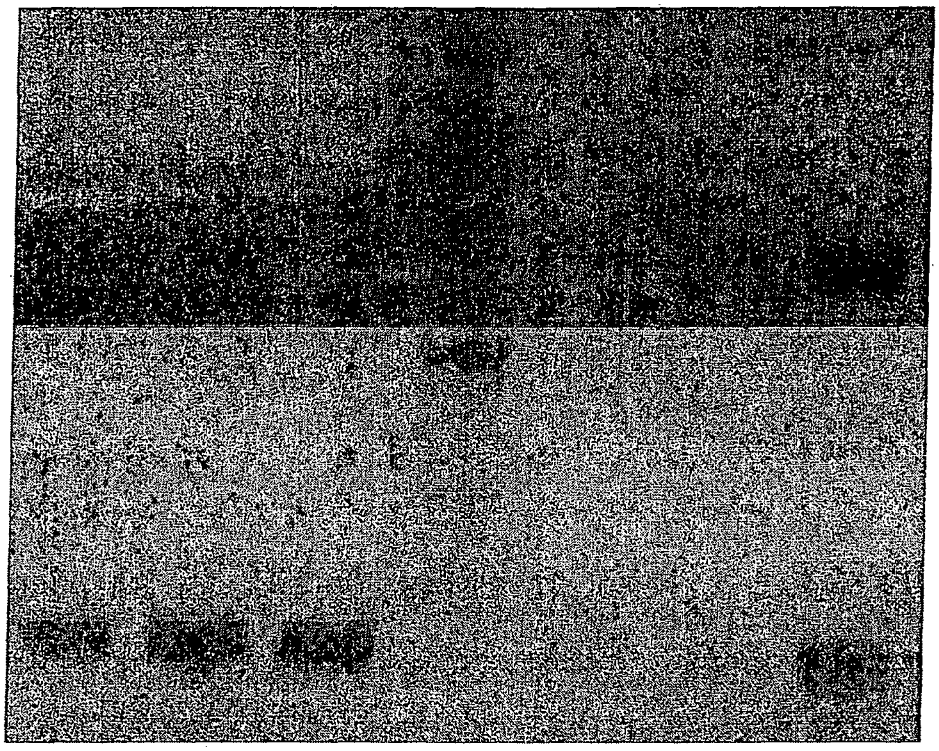

FIG. 9 depicts the results of an RT-PCR reaction, which demonstrates CFTR mRNA expression in lungs of rAAV5-CB-Δ264CFTR-treated CF mice. RT-PCR was performed on whole lung RNA samples in a manner analogous to that presented for cell line mRNA in FIG. 7. The CFTR-specific band is shown in the upper panel, and a GAPDH control to demonstrate the presence of intact mRNA in each sample is shown in the bottom panel. Lung RNA samples from three independent saline-injected control animals are shown on the left half of the figure ("control" lanes), while lung RNA samples from three vector-injected animals are shown on the right half (rAAV5-CFTR).

Figure 10:
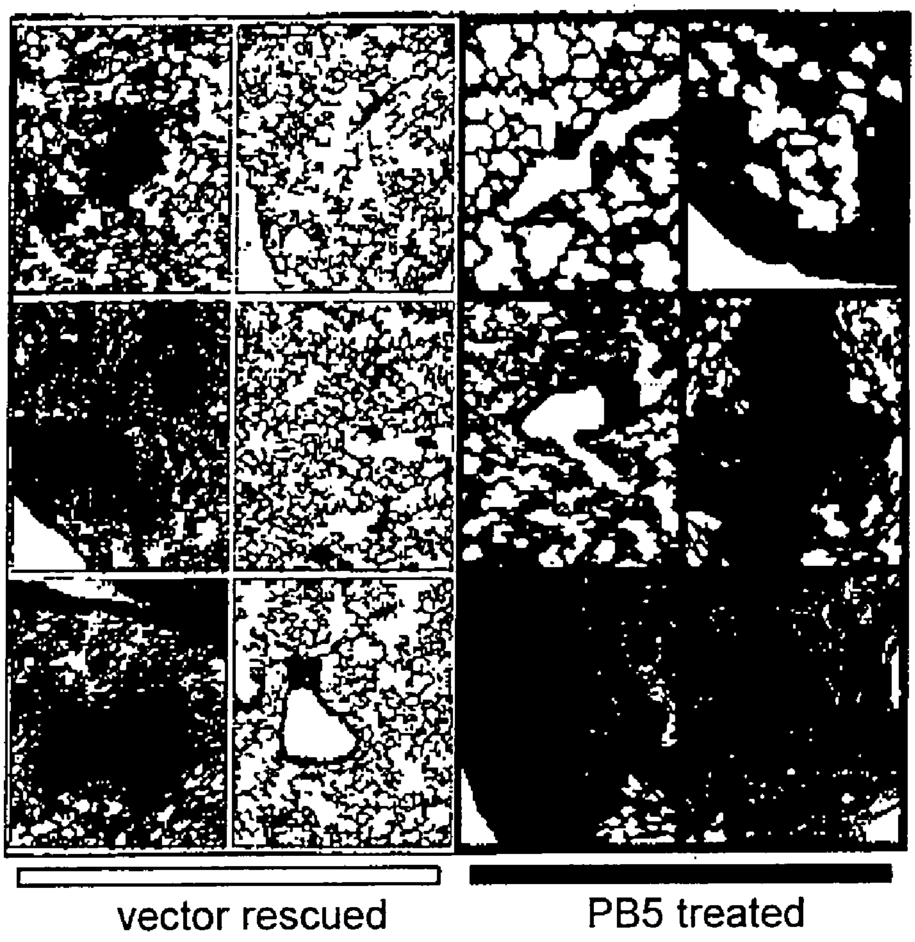

FIG. 10 illustrates prevention of lung inflammation by rAAV5-CB-Δ264CFTR gene therapy in *Pseudomonas*-infected CF mice. The top six panels show randomly-selected, representative fields of hematoxylin-eosin stained lung sections from PBS-treated control CFTR −/− mice 3 to 4 days after *Pseudomonas* challenge. The bottom 6 panels show similar fields from animals pre-treated with rAAV5-CB-Δ264CFTR.

Figure 11:
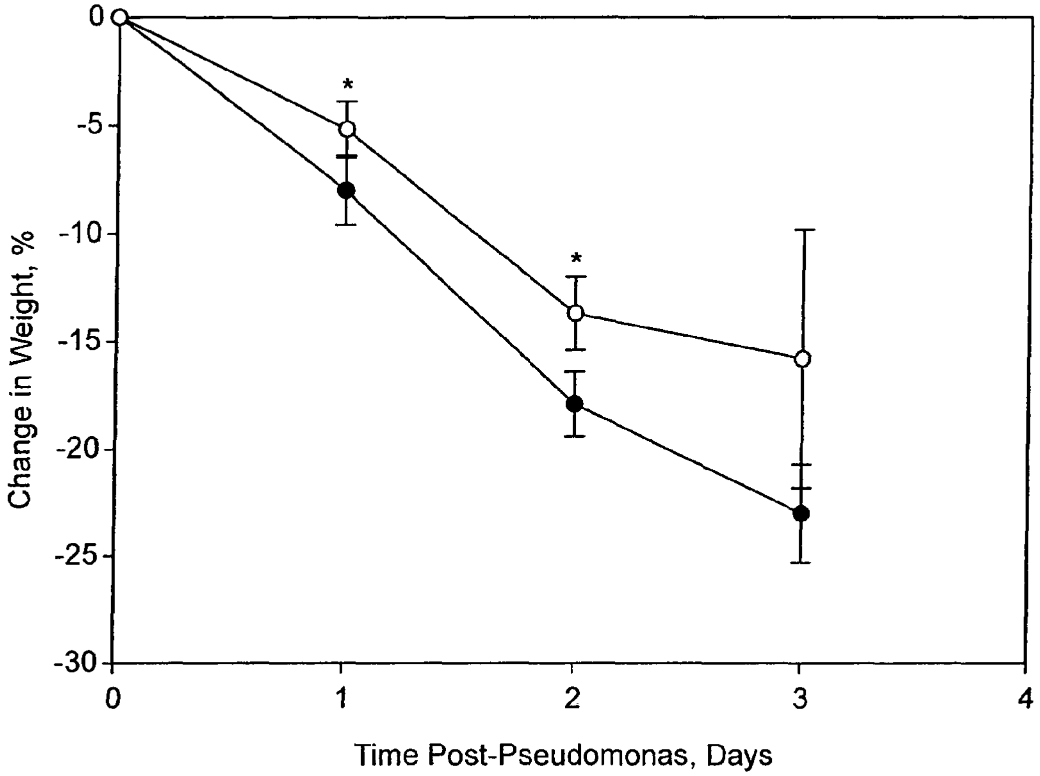

FIG. 11 graphically depicts the amelioration of weight loss by rAAV5-CB-Δ264CFTR gene therapy in *Pseudomonas*-infected CF mice. Shown are the means ±standard deviations of the percent changes in weight after *Pseudomonas*-agarose bead intratracheal challenge for CFTR−/− mice in a rAAV5-CB-Δ264CFTR-treated group and in a GFP-treated control group. N=6 for each time point. "*" indicates $P<0.05$ difference between the two groups.

FIG. 12A-F depicts the nucleic acid sequence (SEQ ID NO: 1) of a rAAV plasmid vector comprising a nucleic acid sequence encoding a truncated biologically active CFTR protein, in accordance with the invention.

Figure 13:
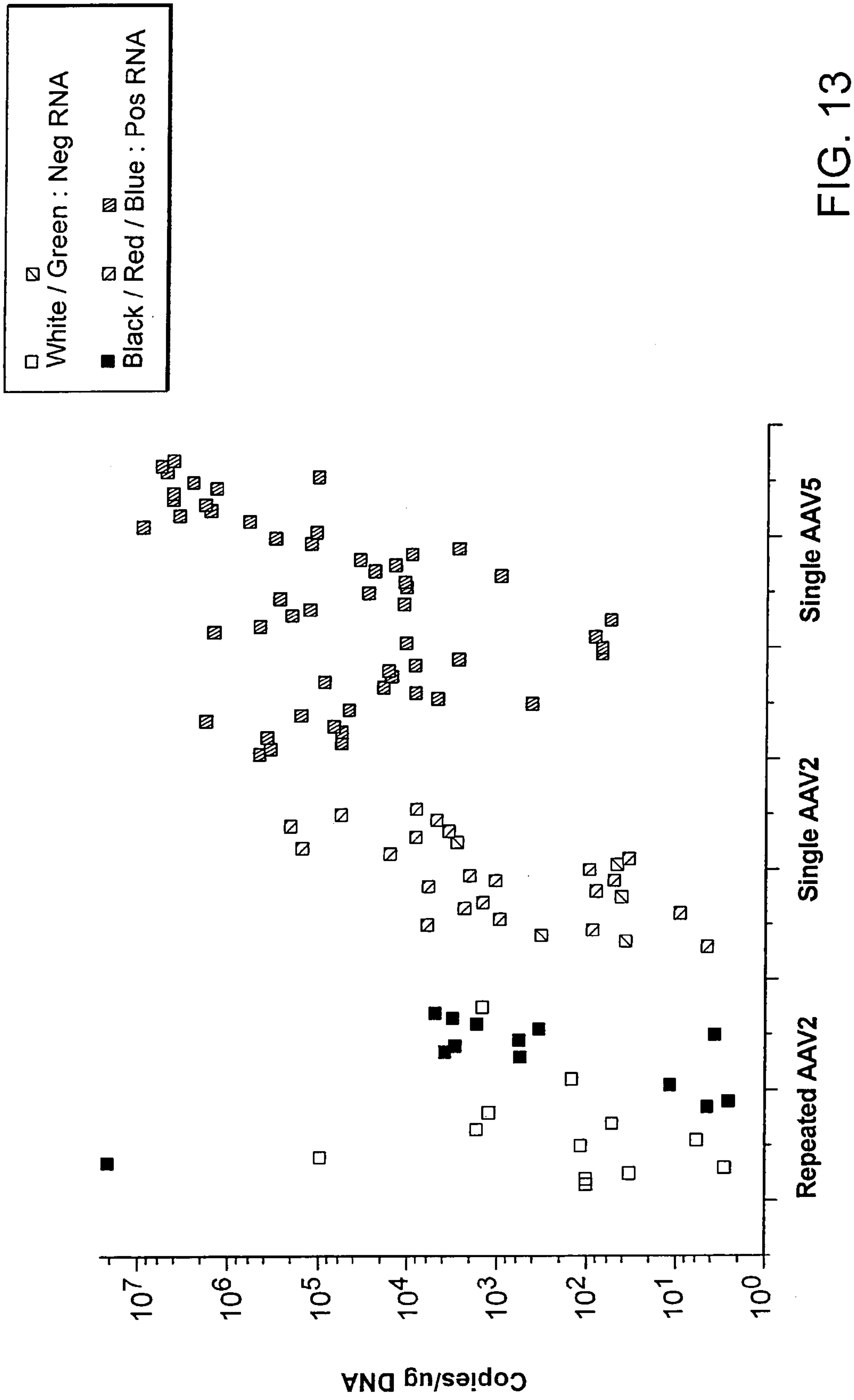

FIG. 13 is a graph illustrating copies/μg of DNA in each lung region measured in monkeys infected with either repeated or single dosing of AAV2, or a single dose of AAV5-GFP. All data points represent copies of DNA measured in each lung region; filled boxes representing black, red, or blue color as shown in the boxed legend depict those samples that were both positive for DNA and RNA transfer.

Figure 14:
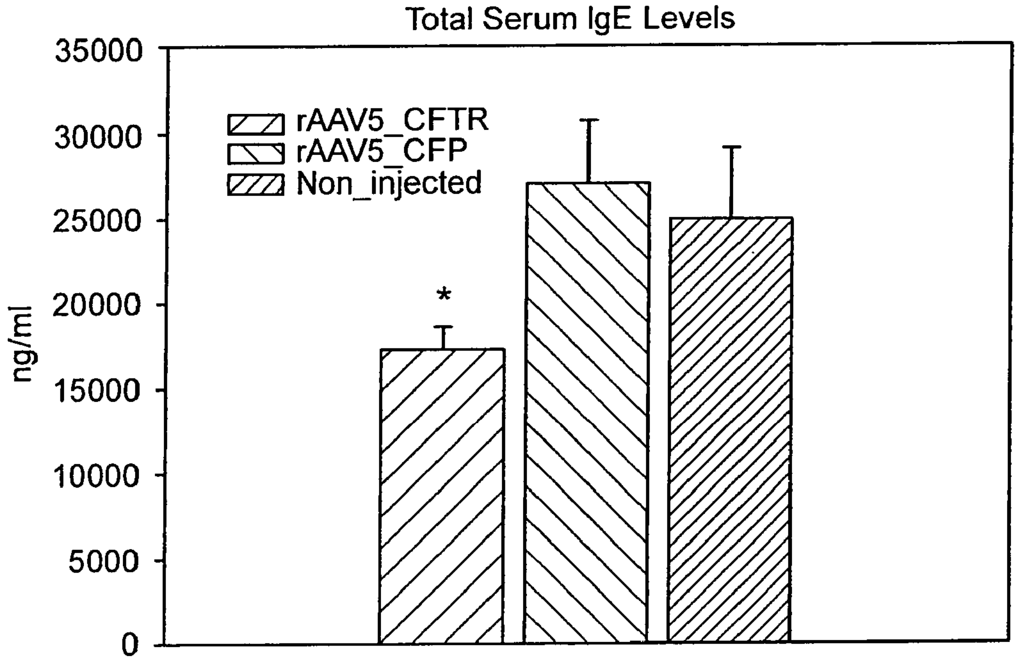

FIG. 14 is a graph showing down regulation of IgE responses following AAV5-CFTR gene therapy. Total serum IgE levels were measured by ELISA. CFTR S489X −/−; FABP-hCFTR (+/+) mice were injected with rAAV virus expressing the delta264CFTR mini gene or GFP, driven by a CB promoter. Subsequently the mice were sensitized with *Aspergillus Fumigatus* (Af) crude extract via the intraperitoneal route and challenged with nebulized Af extract in an enclosed chamber. Serum was harvested 48 hrs after the last challenge for IgE analysis.

Figure 15A:
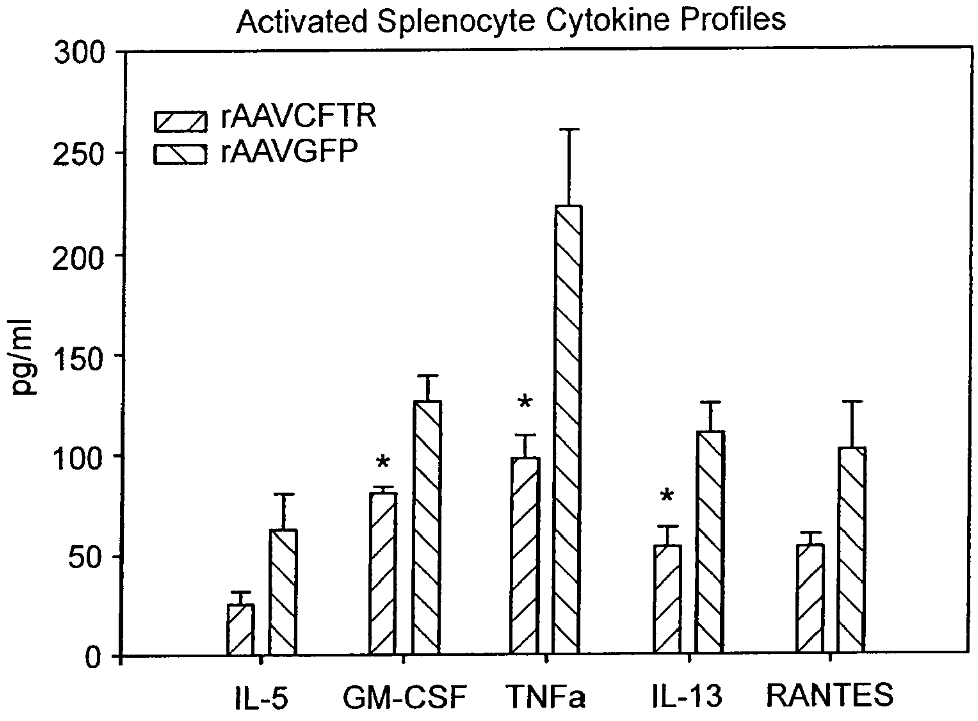

FIGS. 15A and 15 B are two graphs depicting the effects of rAAV5-CFTR gene therapy on the secretion of cytokines by splenocytes. Splenocytes from rAAV5-CFTR and rAAV5-GFP treated mice were harvested 48 hrs after the last Af challenge. The splenocytes were plated in 96-well plates at a density of $10^5$ cells/well and activated with ConA. Supernatants were collected at 48 hrs and subsequently analyzed for levels of cytokines including IL-5, GM-CSF, TNF-α, IL-13, RANTES, IL-2, IL-4 and INF G, using a Luminex 100 system.

Figure 16A:
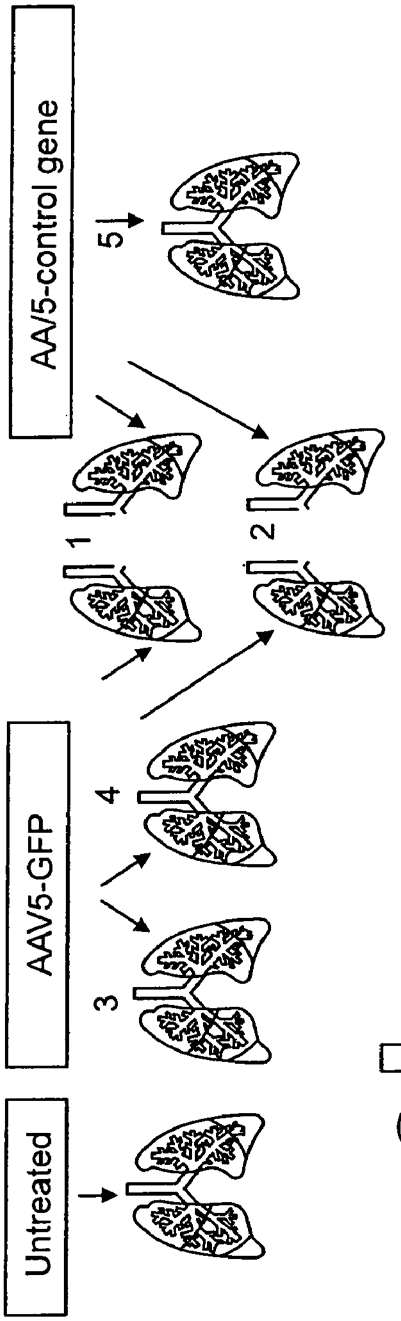
Figure 16B:
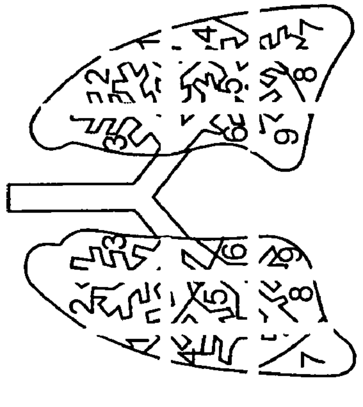
Figure 16C:
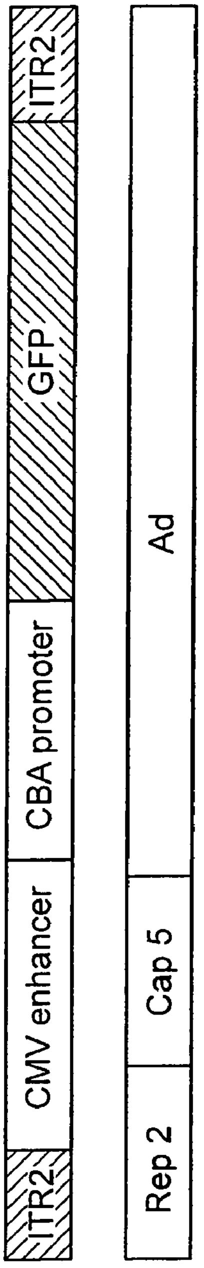

FIG. 16A-C shows schematic representations of experimental methods in accordance with an embodiment of the invention. As shown in FIG. 16A, six rhesus macaques were dosed with up to $2\times10^{14}$ DRP of either a pseudotyped AAV5-GFP or pseudotyped AAV5-irrelevant gene and one macaque remained as an untreated control. Five macaques were dosed with the following regimen: AAV5-GFP to the right lungs and an AAV5-irrelevant gene to the left lungs (1, 2); or AAV5-GFP to both lungs (3, 4). Two animals received $0.5\times10^{14}$ DRP/lung (1, 3) and two received $1\times10^{14}$ DRP/lung (2, 4). The dose of the pseudotyped, irrelevant control gene was the same ($1\times10^{14}$ DRP/lung). FIG. 16B is a schematic representation of the lung regions as defined. There are nine regions per lung (18 regions per animal) biplanar, non-anatomic sections for regional analysis, previously characterized by scintigraphy and described in this airway delivery model. FIG. 16C schematically depicts the structures of plasmids that were cotransfected into 293 cells to form a pseudotyped AAV5 vector, which was then bronchscopically administered to the lungs of the macaques using a Microsprayer™.

Figure 17A:
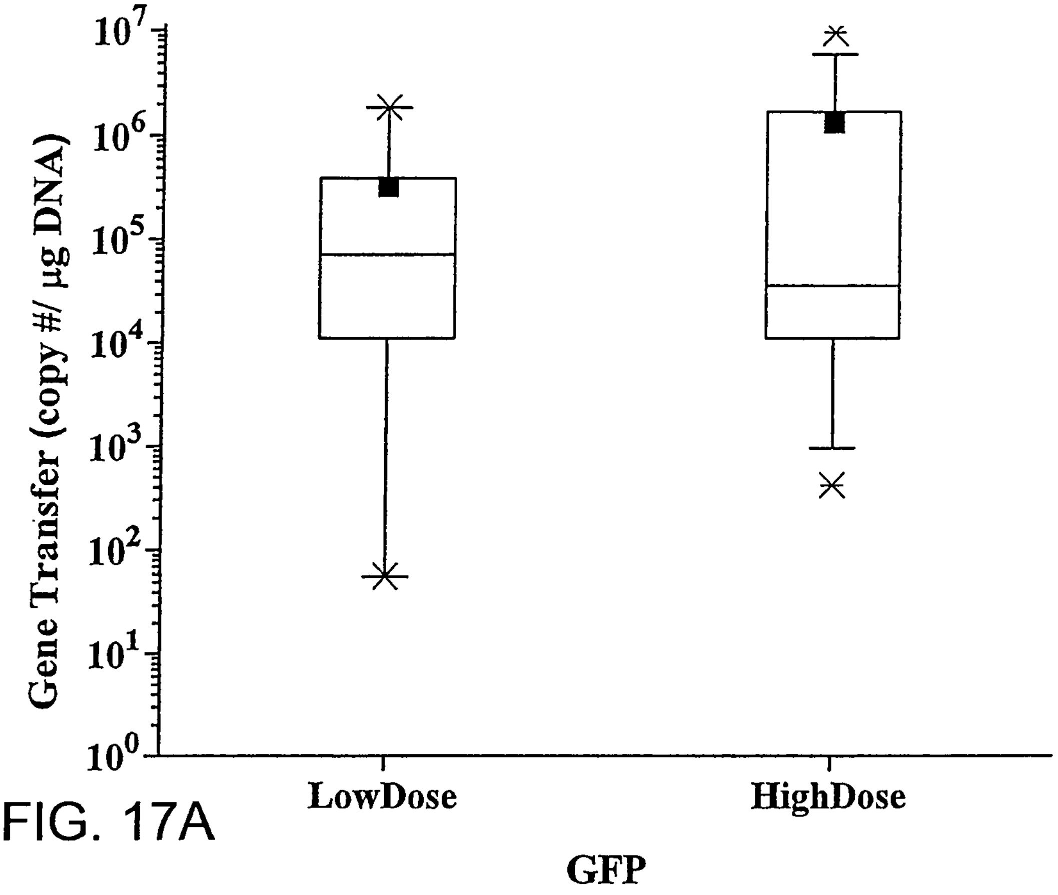
Figure 17B:
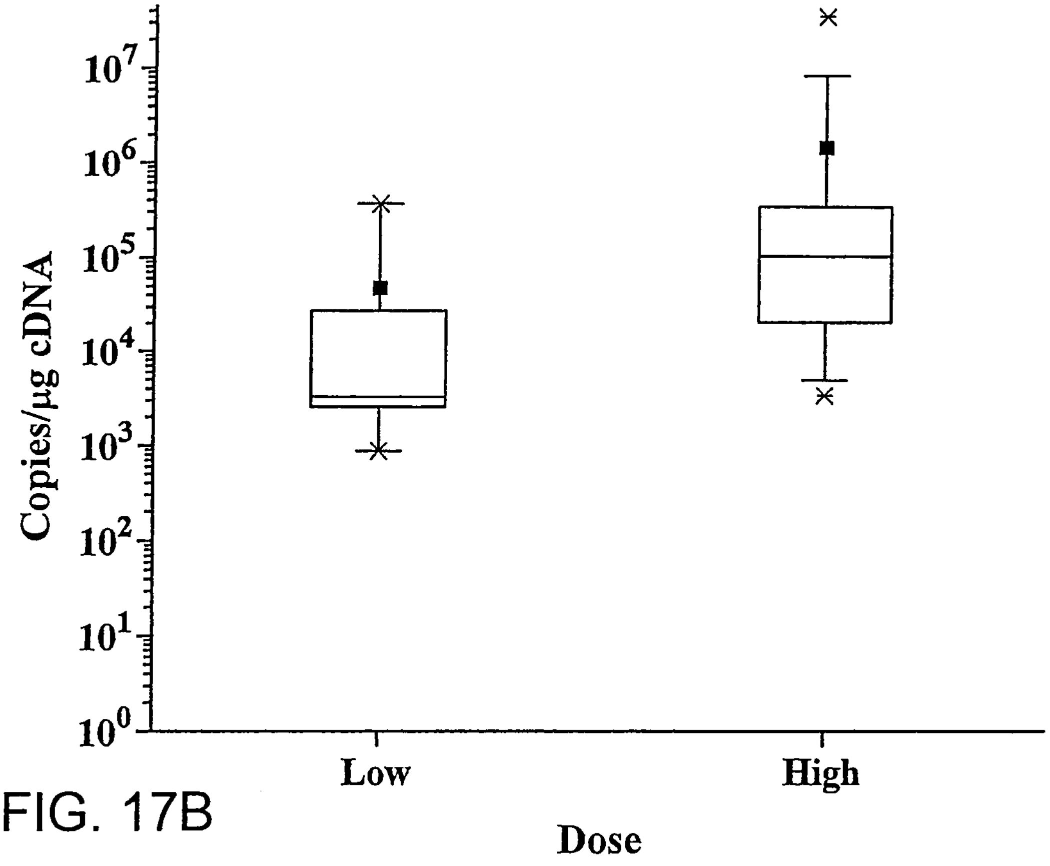
Figure 17C:
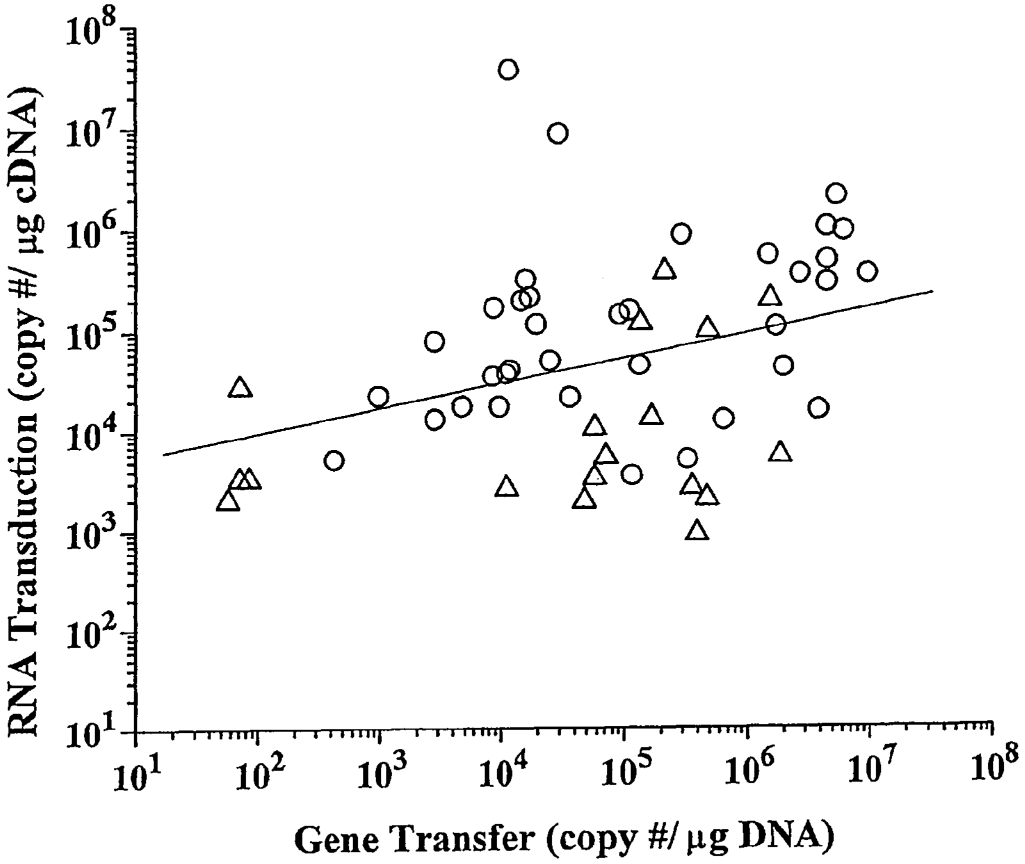

FIG. 17A-C depicts GFP doses per lung. FIG. 17A is a box plot demonstrating GFP dose per lung region versus DNA transfer (copy #/μg DNA). The GFP doses were either a low dose ($0.5\times10^{14}$ DRP/lung) for 18 samples, or high dose ($1\times10^{14}$ DRP/lung) for 28 samples. The black squares (■) represent the averaged mean and the line (-) represents the median. The x's (x) represent the 95% and 5% confidence intervals. FIG. 17B is a box plot showing GFP dose per lung region versus RNA transduction (vector copy #/μg cDNA). The GFP doses were either a low dose ($0.5\times10^{14}$ DRP/lung) for 18 samples or high dose ($1\times10^{14}$ DRP/lung) for 28 samples. The black squares (■) represent the averaged mean and the line (-) represents the median. The x's (x) represent the 95% and 5% confidence intervals. FIG. 17C is a graph demonstrating the gene transfer (copy #/μg DNA) per lung region analyzed versus RNA transduction (vector copy #/μg DNA). The circles (°) represent low dose GFP ($0.5\times10^{14}$ DRP/lung) and the triangles (Δ) represent high dose GFP $1\times10^{14}$ DRP/lung.

Figure 18A:
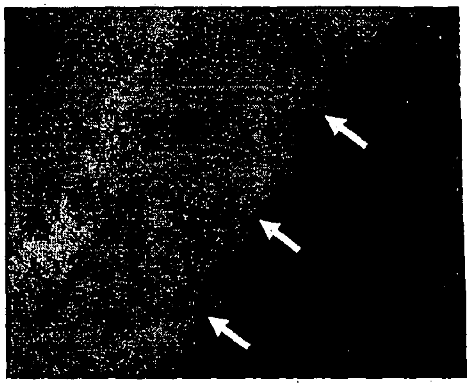
Figure 18C:
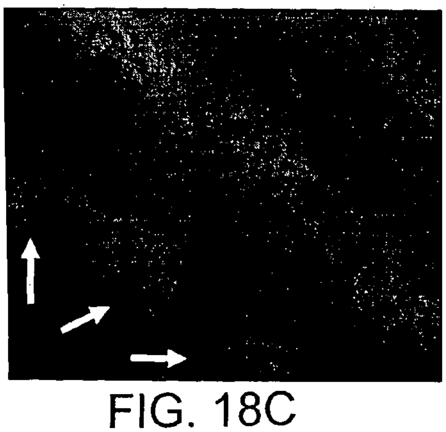
Figure 18B:
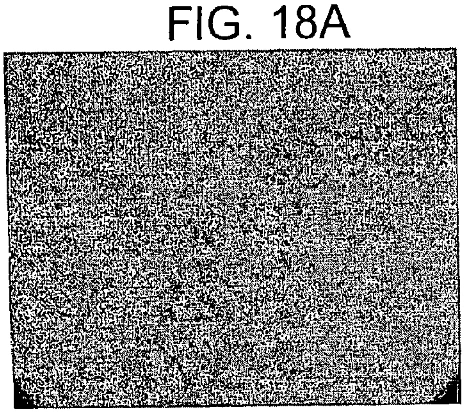
Figure 18D:
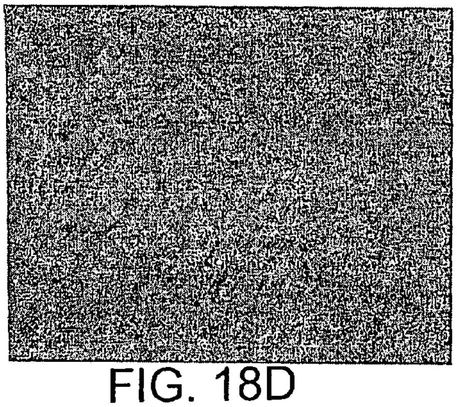
Figure 18E:
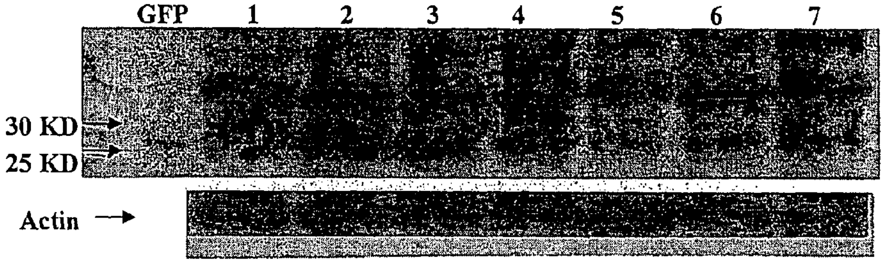
Figure 19A:
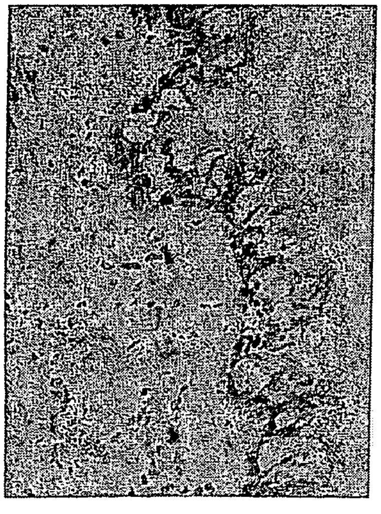
Figure 19B:
Figure 19C:
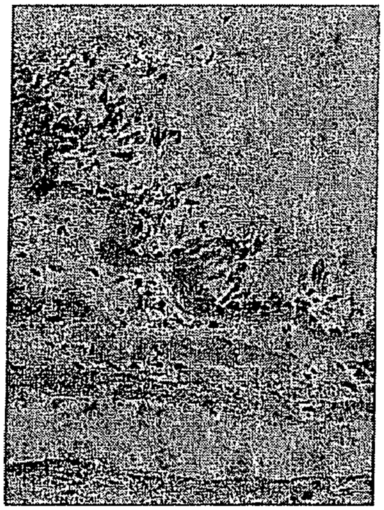
Figure 19D:
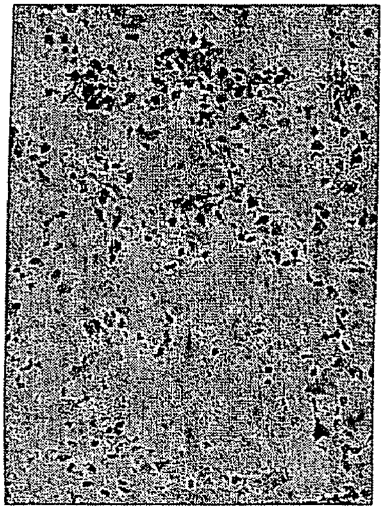
Figure 19E:
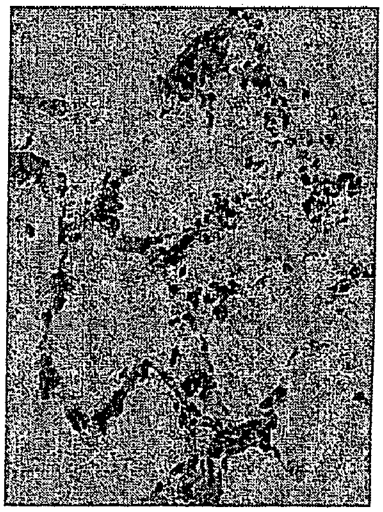
Figure 19F:
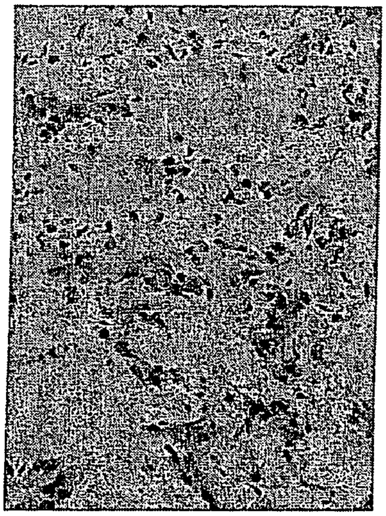

FIG. 18A-E demonstrates GFP protein expression in monkey lungs. Fluorescent GFP expression is shown upon microscopy in bronchial epithelium three weeks after dosing with the vector. Lungs were sectioned into nine regions/lung and dissected at the level of segmental branching and underwent frozen sectioning before being analyzed for GFP fluorescent expression by microscopy. GFP expression is shown in the cytoplasm of ciliated airway epithelial cells in a pseudotyped AAV5-GFP treated macaque (18A) and there is an absence of GFP-specific expression in pulmonary sections from a control macaque (18C). FIGS. 18B and 18D are bright field images of the corresponding sections. Magnification is 1000×. FIG. 18E is a Western blot showing rAAV5-mediated GFP expression in the lung.

FIG. 19A-F depicts histological images from lungs of monkeys comparing experimental to control animals. Hematoxylin and eosin-stained lung sections depict representative experimental (19A and 19D) and control animals (19B and 19E), and an untreated control (19C and 19F), and demonstrate the overall absence of pathologic inflammation near the proximal airways and airway epithelium (19A-C) as well as in the distal alveoli (19D-F). Magnification is 20×.

Figure 20A:
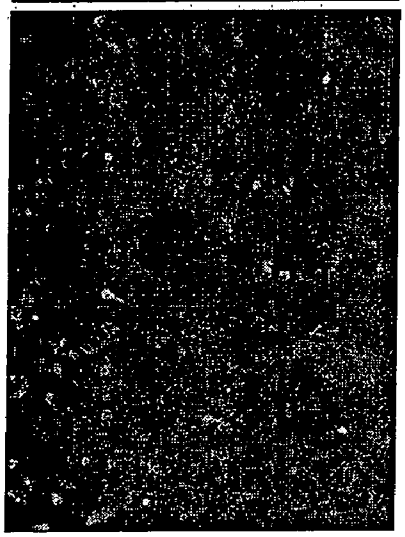
Figure 20B:
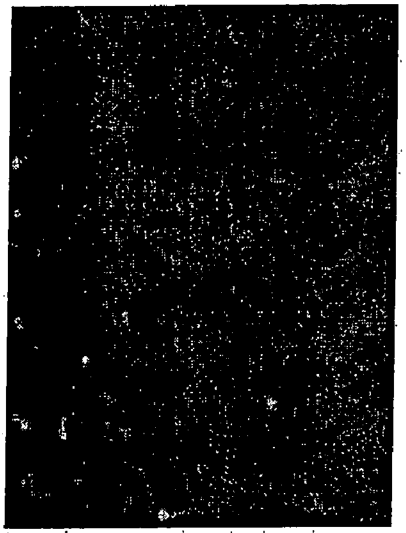
Figure 20C:
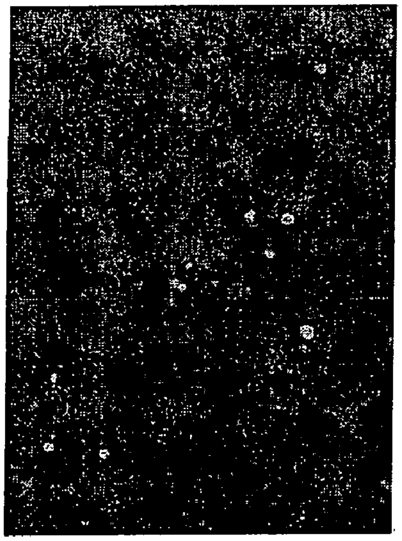
Figure 20D:
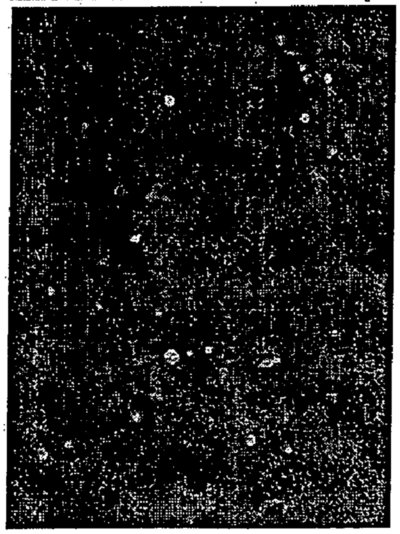
Figure 20E:
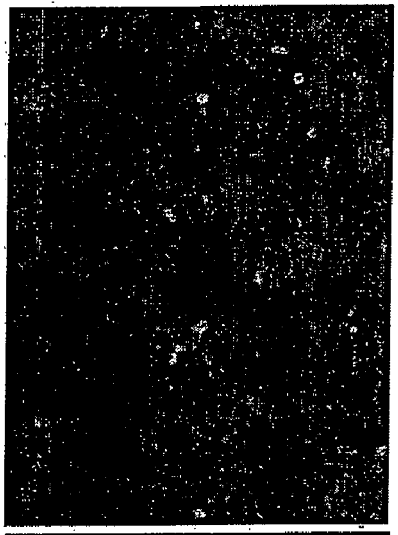
Figure 20F:
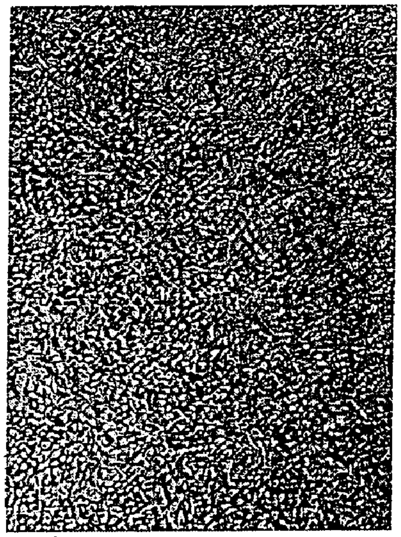

FIG. 20A-F depicts analysis of anti-AAV neutralizing antibody activity in sera from monkeys. FIGS. 20A-B show fluorescent micrographs of hepatoma c12 cells infected with a pseudotyped rAAV5-GFP viral vector and preincubated with monkey sera either prior to dosing (20A) or three weeks post dosing (20B). Similar fluorescent micrographs are shown for sera from an animal treated with irrelevant gene prior to dosing (20D) or three weeks post dosing (20E). FIG. 20C represents the positive in vitro control of AAV5-GFP c 12 cells co-infected with Ad5 without sera and FIG. 20F depicts a representative bright field image. FIG. 20F depicts an ELISA demonstrating no anti-GFP reactivity in the sera. Serum from all macaques was obtained prior to vector exposure and three weeks following vector exposure. Reactivity of the sera (diluted 1:500) to Immulon plates coated with 50 μg GFP was not demonstrated in any of the macaques that had been exposed to pseudotyped AAV5-GFP or pseudotyped AAV5-control gene. The positive control demonstrated strong anti-GFP reactivity with an anti-GFP antibody diluted to the same dilution.

Figure 21:
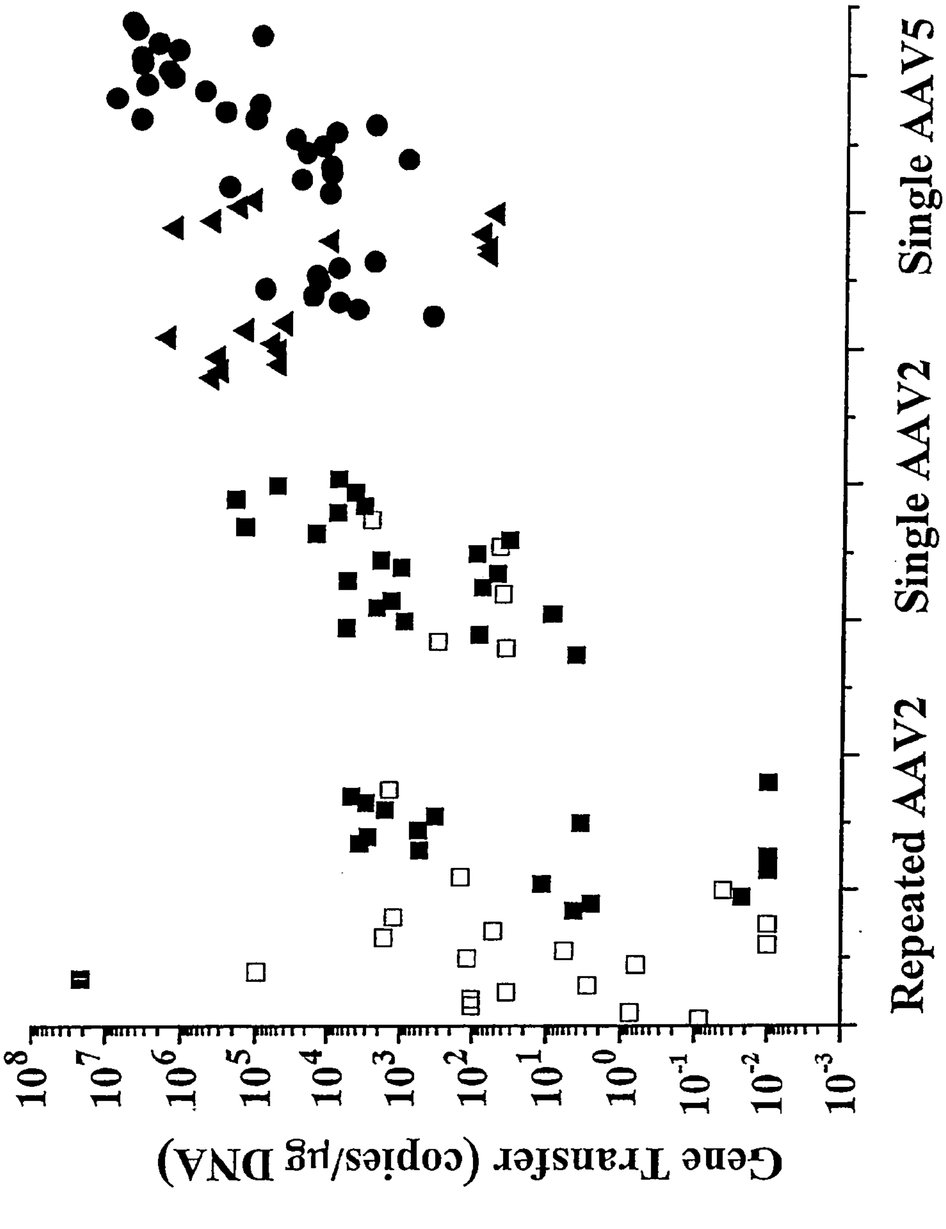

FIG. 21 is a graph depicting an increase in GFP transfer and transduction in monkey lung. GFP DNA transfer was quantified by real-time PCR and expressed as copies/μg DNA and compared to the transfer previously quantified in the prior single and repeat dosing studies of AAV2 (dose=$0.5\times10^{14}$ DRP/lung). Also shown is a study of single dose [high dose (●) and low dose (▲) of $0.5\times10^{14}$ or $1.0\times10^{14}$ DRP/lung, respectively] of pseudotyped AAV5-GFP. Also shown is the increase in number of samples positive for RNA expression (■, ▲, ●) while the open symbols (□) reflect the absence of RNA expression for given lung section and were only detected in the prior AAV2 studies. Single dosing with AAV2-GFP resulted in 22/27 positive RNA regions, repeated dosing studies with AAV2-GFP resulted in 18/36 regions, whereas single dosing with pseudotyped AAV5-GFP resulted in regions positive for RNA transduction in all regions.

Figure 22:
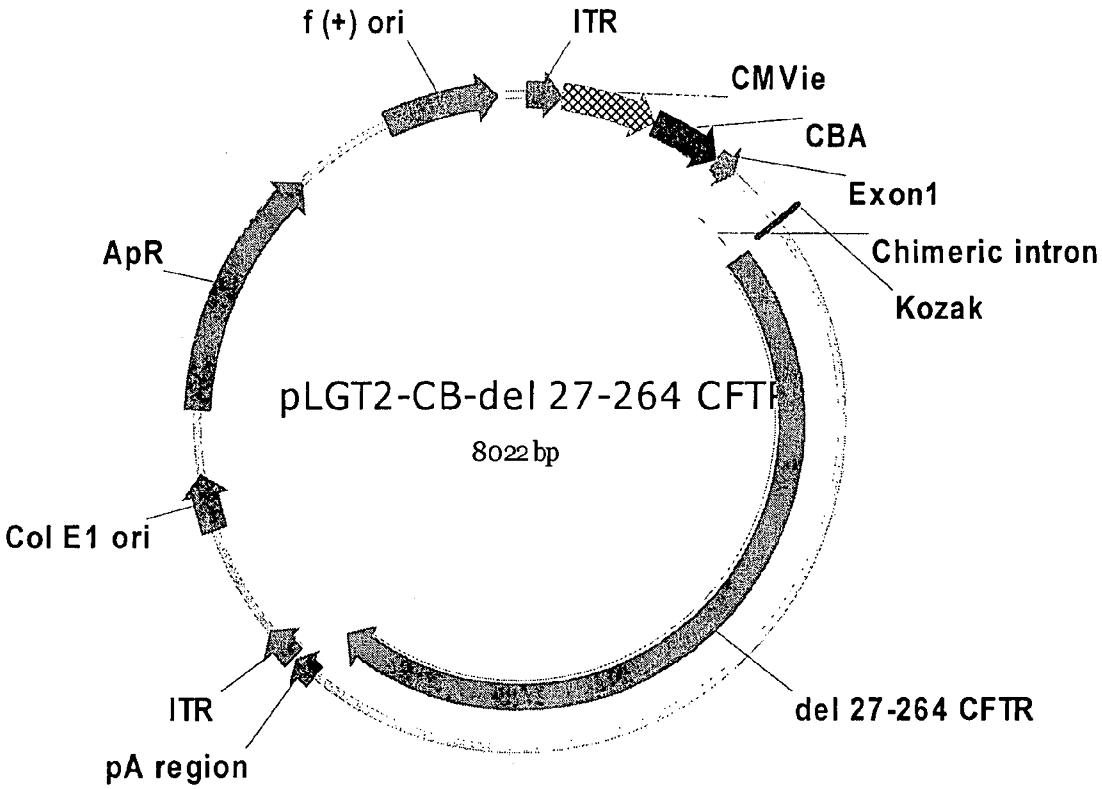

FIG. 22 is a schematic diagram illustrating components of an AAV vector plasmid (pLGT2-CB-del 27-264 CFTR) expressing a biologically active truncated CFTR protein suitable for packaging in rAAV viral vector such as an AAV serotype 5 vector, in accordance with an embodiment of the invention.

DETAILED DESCRIPTION OF THE INVENTION

Disclosed herein is an AAV gene therapy particle. Further disclosed herein are pharmaceutical compositions and methods for treating, preventing or reducing symptoms of cystic fibrosis.

We provide compositions and methods of cystic fibrosis treatment utilizing transgene expression from, for example, rAAV5 and rAAV2 pseudotypes. We also provide several preferred embodiments of pseudotyped rAAV2/5 vectors comprising AAV2 ITRs and effective fragments of the CFTR gene encapsidated with AAV5 proteins. One embodiment, the rAAV5-CB-Δ264CFTR vector, is capable of correcting both the CFTR chloride transport defect in vitro and a CF lung disease phenotype in vivo. Another preferred embodiment is a rAAV5-pLGT2-CB-Δ127-264CFTR vector in which the expressed protein is lacking amino acids 27-264 of the CFTR protein and expression of the protein is in an appropriate location, at the plasma membrane. The reduced size of the nucleic acid sequence encoding the functionally effective truncated CFTR gene product is particularly advantageous for packaging into AAV viral vectors in which packaging capacity is limited. A further advantage of certain pseudotyped rAAV2/5 gene therapy particles of the invention is a powerful promoter of suitable size for packaging with a CFTRgene (further described infra) to drive robust expression of the CFTR transgene in recipient cells.

The adeno-associated virus (AAV) is a single-stranded DNA parvovirus, which integrates into a host genome during the latent phase of infectivity. AAV2, for example, is a particular serotype of AAV that is endemic to the human and primate populations and frequently integrates site-specifically into human chromosome 19 q13.3. AAV is considered a dependant virus because it requires helper functions from either adenovirus or herpes-virus in order to replicate. In the absence of either of these helper viruses, AAV can infect cells, uncoat in the nucleus, and integrate its genome into the host cell chromosome, but cannot replicate or produce new viral particles.

AAVs are useful as transducing vectors, in part, because none of the known serotypes have been linked to any human disease. This feature renders the AAVs distinct from autonomous parvoviruses, which can cause a variety of human disorders. Moreover, AAV virions are of interest as vectors for gene therapy because of their broad host range, excellent safety profile, and the duration of transgene expression in infected hosts. In general, AAV transducing vectors comprise sufficient cis-acting functions to replicate when adenovirus or herpesvirus helper functions are provided in trans. In vectors, the AAV cap and/or rep genes are frequently deleted from the viral genome and replaced with a DNA segment of choice.

As used herein, the terms "gene transfer," "gene delivery," and "gene transduction" refer to methods or systems for reliably inserting a particular nucleotide sequence (e.g., DNA) into targeted cells.

As used herein, the term "gene therapy" refers to a method of treating a patient wherein polypeptides or nucleic acid sequences are transferred into cells of a patient such that activity and/or the expression of a particular molecule is restored.

As used herein, the term "adenoviral associated virus (AAV) vector," "AAV gene therapy vector," and "gene therapy vector" refer to a vector having functional or partly functional ITR sequences and transgenes. As used herein, the term "ITR" refers to inverted terminal repeats (ITR). The ITR sequences may be derived from an adeno-associated virus serotype, including without limitation, AAV-1, AAV-2, AAV-3, AAV-4, AAV-5, and AAV-6. The ITRs, however, need not be the wild-type nucleotide sequences, and may be altered (e.g., by the insertion, deletion or substitution of nucleotides), so long as the sequences retain function to provide for functional rescue, replication and packaging. AAV vectors may have one or more of the AAV wild-type genes deleted in whole or part, preferably the rep and/or cap genes but retain functional flanking ITR sequences. Functional ITR sequences function to, for example, rescue, replicate and package the AAV virion or particle. Thus, an "AAV vector" is defined herein to include at least those sequences required for insertion of the transgene into a subject's cells. Optionally included are those sequences necessary in cis for replication and packaging (e.g., functional ITRs) of the virus.

The terms "adeno-associated virus inverted terminal repeats" or "AAV ITRs" refer to the palindromic regions found at each end of the AAV genome which function together in cis as origins of DNA replication and as packaging signals for the virus. For use in some embodiments of the present invention, flanking AAV ITRs are positioned 5' and 3' of one or more selected heterologous nucleotide sequences. Optionally, the ITRs together with the rep coding region or the Rep expression products provide for the integration of the selected sequences into the genome of a target cell.

As used herein, the term "AAV rep coding region" refers to the region of the AAV genome that encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Muzyczka (Muzyczka, Curr. Top. Microbiol. Immunol., 158:97-129 (1992)) and Kotin (Kotin, Hum. Gene Ther., 5:793-801 (1994)) provide additional descriptions of the AAV rep coding region, as well as the cap coding region described below. Suitable homologues of the AAV rep coding region include the human herpesvirus 6 (HHV-6) rep gene which is also known to mediate AAV-2 DNA replication (Thomson el al., Virol., 204: 304-311 (1994)).

As used herein, the term "AAV cap coding region" refers to the region of the AAV genome that encodes the capsid proteins VP1, VP2, and VP3, or functional homologues thereof. These cap expression products supply the packaging functions, which are collectively required for packaging the viral genome. In certain preferred embodiments, AAV2 Cap proteins may be used. In other preferred embodiments, for example, for gene therapy particles intended for use in the airways, AAV5 Cap proteins may provide the advantage of selective binding to the apical surfaces of airway epithelia (Zabner J, Seiler M, Walters R, Kotin R M, Fulgeras W, Davidson B L, Chiorini J A: Adeno-associated virus type 5 (AAV5) but not AAV2 binds to the apical surfaces of airway epithelia and facilitates gene transfer. J Virol 2000; 74: 3852-8).

As used herein, the term "AAV helper function" refers to AAV coding regions capable of being expressed in a host cell to complement AAV viral functions missing from the AAV vector. Typically, the AAV helper functions include the AAV rep coding region and the AAV cap coding region. The helper functions may be contained in a "helper plasmid" or "helper construct." An AAV helper construct as used herein, refers to a molecule that provides all or part of the elements necessary for AAV replication and packaging. Such AAV helper constructs may be a plasmid, virus or genes integrated into cell lines or into the cells of a subject. It may be provided as DNA, RNA, or protein. The elements do not have to be arranged co-linearly (i.e., in the same molecule). For example, rep78 and rep68 may be on different molecules. An "AAV helper construct" may be, for example, a vector containing AAV coding regions required to complement AAV viral functions missing from the AAV vector (e.g., the AAV rep coding region and the AAV cap coding region). Exemplary AAV helper constructs in the form of plasmids are described in Examples below.

As used herein, the terms "accessory functions" and "accessory factors" refer to functions and factors that are required by AAV for replication, but are not provided by the AAV vector or AAV helper construct. Thus, these accessory functions and factors must be provided by the host cell, a virus (e.g., adenovirus or herpes simplex virus), or another expression vector that is co-expressed in the same cell. Generally, the E1, E2A, E4 and VA coding regions of adenovirus are used to supply the necessary accessory function required for AAV replication and packaging (Matsushita et al., Gene Therapy 5:938 (1998)).

Portions of the AAV genome have the capability of integrating into the DNA of cells to which it is introduced. As used herein, "integrate," refers to portions of the genetic construct that become covalently bound to the genome of the cell to which it is administered, for example through the mechanism of action mediated by the AAV Rep protein and the AAV ITRs. For example, the AAV virus has been shown to integrate at 19q13.3-qter in the human genome. The minimal elements for AAV integration are the inverted terminal repeat (ITR) sequences and a functional Rep 78/68 protein. The present invention incorporates the ITR sequences into a vector for integration to facilitate the integration of the transgene, for example, the CFTR gene or a biologically active portion thereof, into the host cell genome for sustained transgene expression. The genetic transcript may also integrate into other chromosomes if the chromosomes contain the AAV integration site.

The predictability of insertion site reduces the danger of random insertional events into the cellular genome that may activate or inactivate host genes or interrupt coding sequences, consequences that limit the use of vectors whose integration is random, e.g., retroviruses. The Rep protein mediates the integration of the genetic construct containing the AAV ITRs and the transgene. The use of AAV is advantageous for its predictable integration site and because it has not been associated with human or non-human primate diseases, thus obviating many of the concerns that have been raised with virus-derived gene therapy vectors.

Figures 12, 12A:
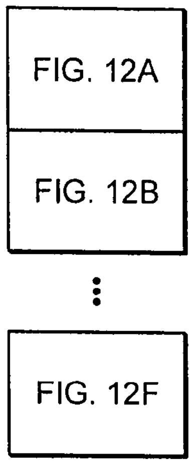

"Portion of the genetic construct integrates into a chromosome" refers to the portion of the genetic construct that will become covalently bound to the genome of the cell upon introduction of the genetic construct into the cell via administration of the gene therapy particle. The integration is mediated by the AAV ITRs flanking the transgene and the AAV Rep protein. Portions of the genetic construct that may be integrated into the genome include the transgene and the AAV ITRs. FIGS. 12 and 23 show the sequences of preferred genetic constructs of the invention (SEQ ID NOS:1 and 8, respectively).

The "transgene" may contain a transgenic sequence or a native or wild-type DNA sequence. The transgene may become part of the genome of the primate subject. In certain aspects of the invention, the transgene is integrated into the chromosomal genome, for example, into chromosome 19. A transgenic sequence can be partly or entirely species-heterologous, i.e., the transgenic sequence, or a portion thereof, can be from a species which is different from the cell into which it is introduced.

As used herein, the term "stably maintained" refers to characteristics of transgenic non-human primates that maintain at least one of their transgenic elements (i.e., the element that is desired) through multiple generations of cells. For example, it is intended that the term encompass many cell division cycles of the originally transfected cell. The term "stable transfection" or "stably transfected" refers to the introduction and integration of foreign DNA into the genome of the cell. The term "stable transfectant" refers to a cell that has stably integrated foreign DNA into the genomic DNA.

As used herein, the terms "transgene encoding," "nucleic acid molecule encoding," "DNA sequence encoding," and "DNA encoding" refer to the order or sequence of deoxyribonucleotides along a strand of deoxyribonucleic acid. The order of these deoxyribonucleotides may, for example, determine the order of amino acids along the polypeptide (protein) chain. The DNA sequence thus may code for the amino acid sequence.

As used herein, the term "wild type" (wt) refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants may be isolated, which are identified by the acquisition of altered characteristics when compared to the wild-type gene or gene product.

As used herein, the term "AAV virion," "AAV particle," or "AAV gene therapy particle," "AAV gene therapy vector," or "rAAV gene therapy vector" refers to a complete virus unit, such as a wt AAV virus particle (comprising a linear, single-stranded AAV nucleic acid genome associated with at least one AAV capsid protein coat). In this regard, single-stranded AAV nucleic acid molecules of either complementary sense (e.g., "sense" or "antisense" strands) can be packaged into any one AAV virion and both strands are equally infectious. Also included are infectious viral particles containing a heterologous DNA molecule of interest (e.g., CFTR or a biologically active portion thereof), which is flanked on both sides by AAV ITRs. In some embodiments of the present invention, a rAAV virion or gene therapy particle is produced in a suitable host cell, which contains an AAV vector, AAV helper functions and accessory functions. In this manner, the host cell is rendered capable of encoding AAV polypeptides that are required for packaging the AAV vector containing a recombinant nucleotide sequence of interest, such as CFTR, or a portion or functional fragment of CFTR, into recombinant virion particles such as the rAAV5-CB-Δ264-CFTR vector or the rAAV5-CB-Δ27-264-CFTR vector, for subsequent gene delivery to patients suffering from cystic fibrosis.

As used herein, the term "transfection" refers to the uptake of foreign DNA by a cell. A cell has been "transfected" when exogenous DNA has been introduced inside the cell membrane. A number of transfection techniques are generally known in the art (See e.g., Graham et al., Virol., 52:456 (1973); Sambrook et al., Molecular Cloning, a Laboratory Manual, Cold Spring Harbor Laboratories, New York (1989); Davis et al., Basic Methods in Molecular Biology, Elsevier, (1986); and Chu et al., Gene 13:197 (1981). Such techniques may be used to introduce one or more exogenous DNA moieties, such as a gene transfer vector and other nucleic acid molecules, into suitable recipient cells.

As used herein, the terms "stable transfection" and "stably transfected" refers to the introduction and integration of foreign DNA into the genome of the transfected cell. The term "stable transfectant" refers to a cell, which has stably integrated foreign DNA into the genomic DNA.

As used herein, the term "transient transfection" or "transiently transfected" refers to the introduction of foreign DNA into a cell wherein the foreign DNA fails to integrate into the genome of the transfected cell and is maintained as an episome. During this time the foreign DNA is subject to the regulatory controls that govern the expression of endogenous genes in the chromosomes. The term "transient transfectant" refers to cells which have taken up foreign DNA but have failed to integrate this DNA. As used herein, the term "transduction" denotes the delivery of a DNA molecule to a recipient cell either in vivo or in vitro, via a replication-defective viral vector, such as via a recombinant AAV virion.

As used herein, the term "recipient cell" refers to a cell which has been transfected or transduced, or is capable of being transfected or transduced, by a nucleic acid construct or vector bearing a selected nucleotide sequence of interest (e.g., CNTF). The term includes the progeny of the parent cell, whether or not the progeny are identical in morphology or in genetic make-up to the original parent, so long as the selected nucleotide sequence is present. The recipient cell may be the cells of a subject to which the gene therapy particles and/or gene therapy vector has been administered.

As used herein, the term "nucleic acid" sequence refers to a DNA or RNA sequence. Nucleic acids can, for example, be single or double stranded. The term includes sequences such as any of the known base analogues of DNA and RNA.

As used herein, the term "recombinant DNA molecule" refers to a DNA molecule which is comprised of segments of DNA joined together by means of molecular biological techniques.

As used herein, the term "regulatory element" refers to a genetic element which can control the expression of nucleic acid sequences. For example, a promoter is a regulatory element that facilitates the initiation of transcription of an operably linked coding region. Other regulatory elements are splicing signals, polyadenylation signals, termination signals, etc.

The term DNA "control sequences" refers collectively to regulatory elements such as promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need be present.

Transcriptional control signals in eukaryotes generally comprise "promoter" and "enhancer" elements. Promoters and enhancers consist of short arrays of DNA sequences that interact specifically with cellular proteins involved in transcription (Maniatis et al., Science 236:1237 (1987)). Promoter and enhancer elements have been isolated from a variety of eukaryotic sources including genes in yeast, insect and mammalian cells and viruses (analogous control sequences, i.e., promoters, are also found in prokaryotes). The selection of a particular promoter and enhancer depends on the recipient cell type. Some eukaryotic promoters and enhancers have a broad host range while others are functional in a limited subset of cell types (See e.g., Voss et al., Trends Biochem. Sci., 11:287 (1986); and Maniatis et al., supra, for reviews). For example, the SV40 early gene enhancer is very active in a variety of cell types from many mammalian species and has been used to express proteins in a broad range of mammalian cells (Dijkema et al, EMBO J. 4:761 (1985)). Promoter and enhancer elements derived from the human elongation factor 1-alpha gene (Uetsuki et al., J. Biol. Chem., 264:5791 (1989); Kim et al., Gene 91:217 (1990); and Mizushima and Nagata, Nucl. Acids. Res., 18:5322 (1990)), the long terminal repeats of the Rous sarcoma virus (Gorman et al., Proc. Natl. Acad. Sci. U.S.A. 79:6777 (1982)), and the human cytomegalovirus (Boshart et al., Cell 41:521 (1985)) are also of utility for expression of proteins in diverse mammalian cell types. Promoters and enhancers can be found naturally, alone or together. For example, retroviral long terminal repeats comprise both promoter and enhancer elements. Generally promoters and enhancers act independently of the gene being transcribed or translated. Thus, the enhancer and promoter used can be "endogenous," "exogenous," or "heterologous" with respect to the gene to which they are operably linked. An "endogenous" enhancer/promoter is one which is naturally linked with a given gene in the genome. An "exogenous" or "heterologous" enhancer and promoter is one which is placed in juxtaposition to a gene by means of genetic manipulation (i.e., molecular biological techniques) such that transcription of that gene is directed by the linked enhancer/promoter.

As used herein, the term "tissue specific" refers to regulatory elements or control sequences, such as a promoter, enhancers, etc., wherein the expression of the nucleic acid sequence is substantially greater in a specific cell type(s) or tissue(s). In particularly preferred embodiments, the CB promoter (CB is the same as CBA defined above) displays good expression of human CFTR, rAAV5-CB-Δ264CFTR, rAAV5-CB-Δ27-264CFTR, or another biologically active portion of CFTR. It is not intended, however, that the present invention be limited to the CB promoter or to lung specific expression, as other tissue specific regulatory elements, or regulatory elements that display altered gene expression patterns, are encompassed within the invention.

The presence of "splicing signals" on: an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York (1989), pp. 16.7-16.8). A commonly used splice donor and acceptor site is the splice junction from the 16S RNA of SV40.

Transcription termination signals are generally found downstream of a polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which has been isolated from one gene and operably linked to the 3' end of another gene. A commonly used heterologous poly A signal is the SV40 poly A signal. The SV40 poly A signal is contained on a 237 bp BamHI/BclI restriction fragment and directs both termination and polyadenylation (Sambrook et al., supra, at 16.6-16.7).

The terms "operably linked" and "operatively linked" refer to the regulatory sequences for expression of the coding sequence that are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

As used herein, the term "subject" refers to humans and other primates.

As defined herein, a "therapeutically effective amount" or "therapeutic effective dose" is an amount or dose of AAV particles or virions capable of producing sufficient amounts of a desired protein to restore the activity of the protein, thus providing a palliative tool for clinical intervention. A therapeutically effective amount or dose of transfected AAV particles that confer expression of human CFTR, for example, to a cystic fibrosis patient will decrease the symptoms of cystic fibrosis. Additionally, a therapeutically effective amount or dose of transfected AAV gene therapy particles which confer expression of human CFTR or an active portion thereof will prevent any further damage to the lungs or other tissues and prevent or cure the defects.

Cells of the subject useful for administration include all cells of a subject displaying a cystic fibrosis phenotype or which may show a cystic fibrosis phenotype upon development. Examples include, cells of the lung, pancreas, liver, sexual organs, gastrointestinal tract. As used herein, decreasing or ameliorating the symptoms of cystic fibrosis includes lessening or thinning the mucous of a CF subject, rebalancing the salts within and surrounding the cells of a CF patient, correcting the protein folding abnormalities, correcting the cytokine production of the cells, lessening the frequency and duration of lung infections or restoring liver and GI function.

AAV gene therapy vectors of the present invention may be constructed using known techniques to provide, as operably linked components, (a) control sequences including transcriptional initiation and termination regions and (b) nucleotide sequences encoding a desired protein or a functional fragment thereof. The control sequences are selected to be functional in a targeted recipient cell or cell type. The resulting construct, which contains the operatively linked components is bounded (5' and 3') with functional AAV ITR sequences.

The nucleotide sequences of AAV ITR regions are known (See e.g., Kotin, Hum. Gene Ther., 5:793-801 (1994); Berns, “Parvoviridae and Their Replication” in Fields and Knipe (eds), Fundamental Virology, 2nd Edition, for the AAV-2 sequence). AAV ITRs used in the vectors of the invention need not have a wild-type nucleotide sequence, and may be altered (e.g., by the insertion, deletion or substitution of nucleotides). Additionally, AAV ITRs may be derived from any of several AAV serotypes, including without limitation, AAV-1, AAV-2, AAV-3, AAV-4, AAV-5, and AAV6. Furthermore, 5' and 3' ITRs, which may flank a selected nucleotide sequence in an AAV gene therapy vector need not necessarily be identical or derived from the same AAV serotype or isolate, so long as they function as intended. In the gene therapy vectors of the present invention, a first and a second ITR may flank a transgene. The first ITR may be the ITR on the 5' end and the second ITR may be the ITR present on the 3' end of the transgene. The first and the second ITRs may be in the reverse orientation as well.

Heterologous control sequences may be incorporated into the gene therapy vectors. Useful heterologous control sequences generally include those derived from sequences encoding mammalian or viral genes. Examples include, but are not limited to, the SV40 early promoter, mouse mammary tumor virus LTR promoter, adenovirus major late promoter (Ad MLP), a herpes simplex virus (HSV) promoter, a cytomegalovirus (CMV) promoter such as the CMV immediate early promoter region (CMVIE), a Rous sarcoma virus (RSV) promoter, a human muscle creatine kinase promoter, synthetic promoters, hybrid promoters, and the like. A particularly preferred promoter is a chicken beta actin (CB) promoter with intron-exon sequences (324 bp) prior to the ATG translation initiation site added to increase expression. Another preferred promoter is an enhanced chicken beta actin (CB) promoter, e.g., a cytomegalovirus enhancer/chicken beta-actin promoter.

Alternatively, sequences derived from nonviral genes, such as the murine metallothionein gene can also be used. Such promoter sequences are commercially available (e.g., from Stratagene). The heterologous control sequences may drive expression of the transgene, i.e., the CFTR sequence in the AAV gene therapy vector.

Utilizing a stronger, more efficient promoter may be desirable, however with large genes like the full-length cystic fibrosis transmembrane regulator (CFTR) it is problematic due to the size constraints of AAV. A functional CFTR minigene may be used in this invention, for example, the Δ264 CFTR or a Δ27-264 CFTR. Alternatively, a trans-splicing approach may be taken. These include the use of two separate rAAV vectors whose genomes concatemerize after transduction and the use of spliceasome-mediated RNA trans-splicing. In certain preferred embodiments, a single vector is used because of efficiency. In other preferred embodiments, a truncated CFTR vector may be used.

It is contemplated that in some embodiments, tissue-specific expression of a particular protein may be desirable (e.g., expression of biologically active CFTR by lung cells). Those skilled in the art would be able to determine the proper promoter to be used for the proper tissue. It is often desirable to express a product of a transgene, for example, the CFTR gene or biologically active portion thereof, in a specific tissue or fluid, e.g., the lungs, pancreas, or liver, of a subject. Examples of tissue specific promoters include the following: a neural-specific promoter, e.g., nestin, Wnt-1, Pax-1, Engrailed-1, Engrailed-2, Sonic hedgehog; a liver-specific promoter, e.g., albumin, alpha-1 antirypsin; a muscle-specific promoter, e.g., myogenin, actin, MyoD, myosin; an oocyte specific promoter, e.g., ZP1, ZP2, ZP3; a testes-specific promoter, e.g., protamin, fertilin, synaptonemal complex protein-1; a blood-specific promoter, e.g., globulin, GATA-1, porphobilinogen deaminase; a lung-specific promoter, e.g., surfactant protein C; a skin- or wool-specific promoter, e.g., keratin, elastin; endothelium-specific promoters, e.g., Tie-1, Tie-2; a bone-specific promoter, e.g., BMP and AAV P5. General promoters can be used for expression in several tissues. Examples of general promoters include beta-actin, ROSA-21, PGK, FOS, c-myc, Jun-A, Jun-B, and CB.

AAV gene therapy vectors that contain a control sequence and a nucleotide sequence of interest, bounded or flanked by AAV ITRs (i.e., AAV gene therapy vectors), can be constructed by directly inserting selected sequences into an AAV genome with the major AAV open reading frames (“ORFs”) excised. Other portions of the AAV genome can also be deleted, so long as a sufficient portion of the ITRs remain to allow for replication and packaging functions. These constructs can be designed using techniques well known in the art (See e.g., U.S. Pat. Nos. 5,173,414 and 5,139,941, all of which are herein incorporated by reference); International Publication Nos. WO 92/01070 and WO 93/03769; Lebkowski et al., Mol. Cell. Biol., 8:3988-3996 (1988); Vincent et al., Vaccines 90 (Cold Spring Harbor Laboratory Press, 1990); Carter, Curr. Opin. Biotechnol., 3:533-539 (1992); Muzyczka, Curr. Top. Microbiol. Immunol., 158:97-129 (1992); Kotin, Hum. Gene Ther., 5:793-801 (1994); Shelling and Smith, Gene Ther., 1:165-169 (1994); and Zhou et al., J. Exp. Med., 179:1867-1875 (1994)).

Alternatively, AAV ITRs can be excised from the viral genome or from an AAV vector containing the same and fused 5' and 3' of a selected nucleic acid construct that is present in another vector using standard ligation techniques, such as those described in Sambrook et al., supra. For example, ligations can be accomplished in 20 mM Tris-Cl (pH 7.5), 10 mM $MgCl_2$, 10 mM DTT, 33 μg/ml BSA, 10 mM-50 mM NaCl, and either 40 CM ATP, 0.01-0.02 (Weiss) units T4 DNA ligase at 0° C. (for “sticky end” ligation) or 1 mM ATP, 0.3-0.6 (Weiss) units T4 DNA ligase at 4° C. (for “blunt end” ligation). Intermolecular “sticky end” ligations are usually performed at 30-100 μg/ml total DNA concentrations (5-100 nM total end concentration). AAV vectors that contain ITRs have been described in (e.g., U.S. Pat. No. 5,139,941, herein incorporated by reference). In particular, several AAV vectors are described therein which are available from the American Type Culture Collection (“ATCC”) under Accession Numbers 53222, 53223, 53224, 53225 and 53226.

Recombinant proteins may also be expressed utilizing the methods of the present invention. The nucleic acid sequences encoding the CFTR gene or portion thereof can be fused in frame, with respect to the translational reading frame, with nucleic acid sequences encoding tags or epitopes. Such tags and/or epitopes are used routinely by skilled practitioners to track protein expression and as means to purify recombinant proteins. For example, a recombinant protein comprising a histidine tag (6-8 histidine residues) may be purified by column chromatography over nickel-bound beads. Alternative tags may include, but are not limited to, the FLAG epitope, the hemagglutinin epitope, GST, and fluorescent tags, such as green fluorescent protein (GFP). The tags may be useful for detecting the expression of the transgene after administration.

Moreover, it is not intended that the present invention be limited to any specific CFTR sequence. Many natural and recombinant forms of CFTR may be useful using a variety of different regulatory elements and control sequences. Therefore, any known DNA sequences coding for biologically active portions of CFTR can be expressed, alone or in combination with at least one additional vector, using the AAV gene therapy vectors and methods of the present invention.

Nucleic acid sequences coding for the above-described proteins may be obtained using recombinant methods, such as by screening cDNA and genomic libraries from cells expressing proteins or by deriving the sequence from a vector known to include the same. Furthermore, the desired sequence may be isolated directly from cells and tissues containing the same, using standard techniques, such as phenol extraction and PCR of cDNA or genomic DNA (See e.g., Sambrook et al., supra, for a description of techniques used to obtain and isolate DNA). Nucleotide sequences encoding a protein of interest may also be produced synthetically, rather than cloned. For example, the complete sequence may be assembled from overlapping oligonucleotides prepared by standard methods and assembled into a complete coding sequence (See e.g., Edge, Nature 292:756 (1981); Nambair et al., Science 223:1299 (1984); and Jay et al., J. Biol. Chem., 259:6311 (1984)).

Although it is not intended that the present invention be limited to any particular methods for assessing the production of biologically active proteins, such methods as immunoassays, gene expression assays (e.g., PCR, RT-PCR) and biological activity assays in vitro and in vivo (e.g., $^{36}Cl^-$ efflux assays, patch clamping assays, assays of levels of cytokines or IgE, and histological or immunohistochemical studies of tissues) are contemplated.

The following is an exemplary embodiment of the present invention wherein nucleic acid sequences encoding CFTR or a biologically active portion thereof are incorporated into the AAV gene therapy vector to generate rAAV virions comprising CFTR which can transduce cells. One of skill in the art would appreciate that nucleic acid sequences encoding other proteins of interest may be incorporated into the AAV gene therapy vectors of the present invention. Generation of CFTR or truncated CFTR expressing rAAV virions or gene therapy particles generally involves the steps of: (1) introducing an AAV vector containing the CFTR or truncated CFTR gene into a host cell; (2) introducing one or more helper viruses and/or accessory function vectors into the host cell; (3) introducing a mixture of AAV helper constructs into the host cell; and (4) culturing the host cell to produce rAAV virions.

"Truncated CFTR," "biologically active portions of CFTR," "effective fragments of CFTR" and "portions of CFTR," as used herein, refer to biologically active portions of the CFTR protein that are able to rescue, reduce or ameliorate the CF phenotype and/or symptoms. For example, Δ264CFTR, which lacks the first 264 amino acids, and Δ27-264CFTR, which lacks amino acids 27-264 of the CFTR protein are exemplary truncated CFTRs. Preferably, biologically active fragments of CFTR are expressed at the plasma membrane. Although several preferred embodiments of truncated CFTR constructs are disclosed herein, the scope of the invention is intended to include any suitable truncated CFTR. One of skill in the art would know how to create other truncated biologically active forms of CFTR.

The above-described vectors and constructs can be introduced into a cell using standard methodology known to those of skill in the art (e.g., transfection). A number of transfection techniques are generally known in the art (See e.g., Graham el al., Virol., 52:456 (1973), Sambrook et al. supra, Davis et al., supra, and Chu et al., Gene 13:197 (1981)). Particularly suitable transfection methods include calcium phosphate co-precipitation (Graham et al., Virol., 52:456-467 (1973)), direct micro-injection into cultured cells (Capecchi, Cell 22:479-488 (1980)), electroporation (Shigekawa et al., BioTechn., 6:742-751 (1988)), liposome-mediated gene transfer (Mannino et al., BioTechn., 6:682-690 (1988)), lipid-mediated transduction (Felgner et al., Proc. Natl. Acad. Sci. U.S.A. 84:7413-7417 (1987)), and nucleic acid delivery using high-velocity microprojectiles (Klein et al., Nature 327:70-73 (1987)).

For the purposes of the invention, suitable host cells for producing rAAV virions and gene therapy particles include microorganisms, yeast cells, insect cells, and mammalian cells, that may be, or have been, used as recipients of a heterologous DNA molecule. The term includes the progeny of the original cell which has been transfected. Thus, as indicated above, a "host cell," or "producer cell," as used herein, generally refers to a cell which has been transfected with an exogenous DNA sequence. Cells from the stable human cell line, 293 (ATCC Accession No. CRL1573) are preferred in the practice of the present invention. The 293 cell line is a human embryonic kidney cell line that has been transformed with adenovirus type-5 DNA fragments (Graham et al., J. Gen. Virol., 36:59 (1977)), and expresses the adenoviral E1a and E1b genes (Aiello et al., Virol., 94:460 (1979)). The 293 cell line is readily transfected, and thus provides a particularly useful system in which to produce rAAV virions.

Host cells containing the above-described AAV gene therapy vectors must be rendered capable of providing AAV helper functions in order to replicate and encapsidate the nucleic acid sequences flanked by the AAV ITRs to produce rAAV virions. AAV helper functions are generally AAV-derived coding sequences that may be expressed to provide AAV gene products that, in turn, function in trans for productive AAV replication. AAV helper functions are used herein to complement necessary AAV functions that are missing from the AAV vectors. Thus, AAV helper functions include one or both of the major AAV ORFs, namely the rep and cap coding regions, or functional homologues thereof.

AAV helper functions are introduced into the host cell by transfecting the host cell with a mixture of AAV helper constructs either prior to, or concurrently with, the transfection of the AAV vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

Some preferred embodiments of rAAV vectors in accordance with the invention are pseudotyped vectors. Recombinant AAV plasmids comprising a transgene, such as a construct including a truncated CFTR coding sequence operably linked to an efficient promoter and flanked by AAV ITR sequences of one serotype (e.g., AAV-2), can be packaged into a rAAV particle of a heterologous serotype (e.g., AAV-5), to produce a rAAV2/5 pseudotyped vector. Methods for producing pseudotyped rAAV vectors are described, for example, in Zolotukhin S, et al., Production and purification of serotype 1, 2, and 5 recombinant adeno-associated viral vectors. Methods 2002; 28: 158-67. As a non-limiting example, an rAAV2-ITR-containing vector plasmid, such as plasmids described in Examples herein, can be co-transfected into cultured cells of a packaging cell line such as HEK-293 (Ad2 E1a/E1b-positive) cells, along with a helper plasmid such as pDG5 containing the AAV2 Rep gene, AAV5 Cap gene, and Ad5 E2a, E4 and VA-RNA genes. The resultant particles are encapsidated with AAV5 Cap proteins. An exemplary rAAV vector in accordance with the present invention is a rAAV2/5 pseudotyped vector that encodes a truncated biologically active fragment of the CFTR protein that expresses at the plasma membrane at high expression levels.

Mixtures of AAV helper constructs can comprise constructs containing cap genes derived from at least two AAV serotypes. In a preferred embodiment, AAV helper constructs may comprises the AAV2 cap gene. Alternately other AAV cap genes may be used, for example, AAV2 or AAV5. Infection of a recipient cell with such a helper construct, in conjunction with a vector construct and helper virus construct (as described herein), may be used to produce AAV gene therapy AAV2 particles. Optionally, the AAV2 and AAV5 vectors may be combined, for example, in a range of different ratios to produce mixtures which are capable of conferring serotype-specific properties to the AAV gene therapy particles produced following infection. Such ratios may range from, for example, 9:1, 4:1, 1:1, 1:4, to 1:9 (with respect to the molar amount of AAV2 and AAV5) for mixtures comprising AAV2 and AAV5 helper constructs. In a particular embodiment, the ratio of AAV2 to AAV5 helper vectors in the mixture may be adjusted (e.g., one part AAV2 to nine parts AAV5) to enhance the likelihood that AAV gene therapy particles produced as described above will have features more distinctive of AAV2 than AAV5.

In other embodiments, AAV helper constructs comprising cap genes derived from at least two different AAV serotypes may be mixed in various ratios to produce a helper construct mix. Infection of a recipient cell, in conjunction with a vector construct and helper virus construct (as described herein), may be used to produce AAV gene therapy particles. AAV serotype vectors may be combined in a range of different ratios to produce mixtures that may be capable of conferring serotype-specific properties to the AAV gene therapy particles produced following infection.

In preferred embodiments, these constructs are in the form of a vector, including, but not limited to, plasmids, phages, transposons, cosmids, viruses, or virions. A number of AAV helper constructs have been described, such as the commonly used plasmids pAAV/Ad and pIM29+45 that encode both Rep and Cap expression products (See e.g., Samulski et al., J. Virol., 63:3822-3828 (1989); and McCarty et al., J. Virol., 65:2936-2945 (1991)). A number of other vectors have been described which encode Rep and/or Cap expression products (See e.g., U.S. Pat. No. 5,139,941, incorporated herein by reference).

Both AAV gene therapy vectors and AAV helper constructs may be constructed to contain one or more optional selectable markers. Suitable markers include genes that confer antibiotic resistance or sensitivity to, impart color to, or change the antigenic characteristics of those cells which have been transfected with a nucleic acid construct containing the selectable marker when the cells are grown in an appropriate selective medium. Several selectable marker genes are useful in the practice of the present invention, including, without limitation, the gene encoding neomycin that allows selection in mammalian cells by conferring resistance to G418 (Sigma). Other suitable markers are known to those of skill in the art.

The host cell (or packaging cell) should also be rendered capable of providing non-AAV derived functions, or "accessory functions," in order to produce rAAV virions. Accessory functions are non-AAV derived viral and/or cellular functions upon which AAV is dependent for its replication. Thus, accessory functions include at least those non-AAV proteins and RNAs that are required in AAV replication, including those involved in activation of AAV gene transcription, stage specific AAV mRNA splicing, AAV DNA replication, synthesis of rep and cap proteins and AAV capsid assembly. Viral-based accessory: functions can be derived from any of the known helper viruses.

Accessory functions may be transfected into host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Alternatively, accessory functions may be provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors may be in the form of a plasmid, phage, virus, transposon or cosmid. Accessory vectors may also be in the form of one or more linearized DNA or RNA fragments which, when associated with the appropriate control sequences and enzymes, may be transcribed or expressed in a host cell to provide accessory functions.

Nucleic acid sequences providing the accessory functions may be obtained from natural sources, such as from the genome of adenovirus, or constructed using recombinant or synthetic methods known in the art. In this regard, adenovirus-derived accessory functions have been widely studied, and a number of adenovirus genes involved in accessory functions have been identified and partially characterized (See e.g., Carter, "Adeno-Associated Virus Helper Functions," in CRC Handbook of Parvoviruses, Vol. I (P. Tijssen, ed.) (1990), and Muzyczka, Curr. Top. Microbiol. Immun., 158:97-129 (1992)). Specifically, early adenoviral gene regions E1a, E2a, E4, VAI RNA and, possibly, E1b are thought to participate in the accessory process (Janik et al., Proc. Natl. Acad. Sci. U.S.A. 78:1925-1929 (1981)). Herpesvirus-derived accessory functions (See e.g., Young et al., Prog. Med. Virol., 25:113 (1979)) and vaccinia virus-derived accessory functions have also been described (See e.g., Carter, supra., and Schlehofer et al., Virol., 152:110-117 (1986)).

As a consequence of the infection of the host cell with a helper virus, or transfection of the host cell with an accessory function vector, accessory functions are expressed which transactivate the AAV helper constructs to produce AAV Rep and/or Cap proteins. The Rep expression products direct excision of the recombinant DNA (including, for example, nucleic acid sequences encoding CFTR, or a functional fragment thereof) from the AAV vector. The Rep proteins also serve to duplicate the AAV genome. The expressed Cap proteins assemble into capsids, and the recombinant AAV genome is packaged into the capsids. Thus, productive AAV replication ensues and the DNA is packaged into rAAV virions.

Following recombinant AAV replication, rAAV gene therapy particles may be purified from the host cell using a variety of conventional purification methods, such as CsCl gradients. As described hereinabove, rAAV gene therapy particles having AAV2 or AAV5 capsid proteins displayed on their surface may be purified via a heparin chromatography column. Further, if helper virus infection is employed to express the accessory functions, residual helper virus may be inactivated, using known methods. For example, adenovirus can be inactivated by heating to temperatures of approximately 60° C. for approximately 20 minutes or more, as appropriate. This treatment selectively inactivates the helper adenovirus which is heat labile, while preserving the rAAV which is heat stable.

The resulting rAAV gene therapy particles may be incorporated into pharmaceutical compositions that may be delivered to a subject, so as to allow production of a biologically active protein (e.g., CFTR or a biologically active portion thereof). In a particular embodiment of the present invention, pharmaceutical compositions comprising sufficient genetic material to enable a recipient to produce a therapeutically effective amount of CFTR that can reduce, stop and/or prevent cystic fibrosis. Alternatively, pharmaceutical compositions comprising sufficient genetic material to enable a recipient to produce a therapeutically effective amount of CFTR which can inhibit damage from the destructive cystic fibrosis phenotype.

AAV gene therapy particles may be administered to any tissue suitable for expression of proteins or fragments thereof. In a preferred embodiment, the AAV gene therapy particles of the present invention. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a subject alone, or in combination with other agents, precursors, drugs or hormones.

In preferred embodiments, the pharmaceutical compositions also contain a pharmaceutically acceptable excipient, also referred to herein as biocompatible pharmaceutical carriers. Such excipients or carriers include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. An exemplary pharmaceutical preparation may be a lyophilized powder which may contain any or all of the following: 1-50 mM histidine, 0.1%-2% sucrose, and 2-7% mannitol, at a pH range of 4.5 to 5.5, that is combined with buffer prior to use.). A thorough discussion of pharmaceutically acceptable excipients is available in Remington's Pharmaceutical Sciences (Mack Pub. Co., 18th Edition, Easton, Pa. (1990)).

Pharmaceutical formulations suitable for bronchial administration may be formulated in aqueous solutions, preferably in physiologically compatible buffers such as Hanks' solution, Ringer's solution, or physiologically buffered saline. Aqueous suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art. The pharmaceutical compositions of the present invention may be manufactured in any manner known in the art (e.g., by means of conventional mixing, dissolving, granulating, dragee-making, levigating, emulsifying, encapsulating, entrapping, or lyophilizing processes).

After pharmaceutical compositions have been prepared, they may be placed in an appropriate container and labeled for treatment. For administration of CFTR-containing or biologically active portion-containing vectors, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of those skilled in the art using the techniques taught in the present invention. Methods include animal studies and dose escalation studies in patients.

The pharmaceutical compositions may also contain other active and/or inactive substances. Examples of active substances include, anti-inflammatory agents.

AAV gene therapy vectors of the present invention comprising nucleic acid sequences encoding, for example, CFTR or a biologically active portion thereof may be administered to a patient by a variety of means (see below) to achieve and maintain a therapeutically effective level of CFTR or a portion thereof. A therapeutically effective level of CFTR may be in the range of between about $10^9$ to about $10^{13}$ DRP/ml. In a preferred embodiment, a therapeutically effective amount of CFTR or a biologically active portion thereof may be maintained by utilizing the AAV vectors of the present invention that encode CFTR or a portion thereof. It is intended that the dosage treatment and regimen used with the present invention will vary, depending upon the subject and the preparation used. Thus, the dosage treatment may be a single dose schedule or a multiple dose schedule. Moreover, the subject may be administered as many doses as appropriate to achieve or maintain the desired effect. Methods pertaining to the administration of standard AAV vectors to humans have been previously described by Kay et al. (2000, Nat Genet 24:257-261), the entire contents of which is incorporated herein by reference in its entirety. In certain circumstances when multiple vector administrations are necessary, it may be desirable to administer and express a protein of interest in an AAV vector which differs from the AAV vector initially administered.

Alternatively, the pharmaceutical compositions of the invention may be injected using a conventional syringe, although other delivery methods such as convection-enhanced delivery are envisioned (See e.g., U.S. Pat. No. 5,720,720, incorporated herein by reference). In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral, suppositories, and transdermal applications. For treatment of lung respiratory conditions associated with CF, a rAAV gene therapy vector may be administered by any of several administration routes known in the art, including pulmonary, endobronchial, topical, intraocular, parenteral, intranasal, intratracheal, intrabronchial, administration.

A clinician specializing in the treatment of cystic fibrosis patients may determine the optimal route for administration of the AAV gene therapy vectors comprising CFTR nucleic acid sequences or portions thereof based on a number of criteria, including, but not limited to: the serotype(s) of the vector used, the condition of the patient, and the purpose of the treatment (e.g., the stage of the disease).

Therapeutic doses of CFTR or biologically active portions thereof will depend on, among other factors, the age and general condition of the subject, the severity of the cystic fibrosis, and the strength of the control sequences. Thus, a therapeutically effective amount in humans will fall in a relatively broad range that may be determined based on the result of clinical trials and the response of individual patients to treatment.

AAV gene therapy vectors of the present invention comprising nucleic acid sequences encoding a desired protein may be administered to a patient by a variety of means (see below) to achieve and maintain a prophylactically and/or therapeutically effective level of the particular protein. In one aspect of the invention, the particular protein encoded by a nucleic acid sequence may be chosen to supplement or restore the levels of the protein in a patient. An attending physician may identify a patient who would benefit from such intervention by providing a definitive diagnosis of the protein deficiency, which typically result from genetic and/or biochemical defects.

One of skill in the art could readily determine specific protocols for using the AAV gene therapy vectors of the present invention for the prophylactic and/or therapeutic treatment of a particular patient. Protocols for the generation of AAV vectors and administration to patients have been described in U.S. Pat. Nos. 6,335,011; 6,221,349; 6,211,163; 6,200,560; 6,027,931; 6,004,797; 6,001,650; 5,962,313; 5,952,221; 5,945,335; 5,858,351; 5,846,528; 5,843,742; and 5,622,856, which are incorporated herein by reference in their entirety.

One skilled in the art will recognize that the methods and compositions described above are also applicable to a range of other treatment regimens known in the art. For example, the methods and compositions of the present invention are compatible with ex vivo therapy (e.g., where cells are removed from the body, incubated with the AAV gene therapy particles and the treated cells are returned to the body).

The AAV gene therapy particles may contain any nucleic acid sequences coding for biologically active full length CFTR. Alternatively, the AAV gene therapy vectors may contain nucleic acid sequences encoding a functional fragment of CFTR, which retains CFTRs biological activity. Administration of AAV gene therapy particles comprising CFTR, or a functional fragment thereof, to a patient can restore CFTR activity such that the subject's cystic fibrosis symptoms are decreased.

Methods of the invention also include methods for identifying an agent useful for the treatment of cystic fibrosis or for preventing or delaying the progression of cystic fibrosis. The methods may include the steps of administering an agent to a subject wherein the subject has a mutation in the CFTR gene and displays a cystic fibrosis phenotype associated with the mutation, and monitoring the cystic fibrosis phenotype in the subject, wherein a decrease in the severity of the cystic fibrosis phenotype is indicative that the agent is useful for treating cystic fibrosis. The agent may be a gene therapy particle as defined herein. The phenotype may be monitored by a qualified physician or by the subject. Objective and subjective criteria may be used to monitor the phenotype. For example, the thickness and amount of mucous and the number and duration of lung infections may be used to indicate whether the agent is useful for decreasing or eliminating CF symptoms. If an agent decreases the symptoms associated with CF, the agent may be considered useful for treating CF. If an agent decreases the symptoms of CG is may be useful to prevent or delay the progression of CF.

The studies in mice, while not revealing any obvious toxicity, were not designed to formally evaluated safety or biodistribution of the vectors of the invention. While the ITRs used in the mice study vectors are AAV2 ITRs, the change in capsid clearly could alter biodistribution in primates, which is likely to relate in large measure to capsid-receptor interactions.

EXAMPLES

It should be appreciated that the invention should not be construed to be limited to the examples that are now described; rather, the invention should be construed to include any and all applications provided herein and all equivalent variations within the skill of the ordinary artisan.

Example 1

This Example summarizes results of preclinical studies in which pseudotyped AAV2/5 vectors were utilized to combine high dose airway delivery with a serotype preferential to the airway surface.

AAV2/5 pseudotyped (rep2 cap5) vectors (both AAV2/5-GFP and AAV2/5-CFTR) were administered at doses up to $1\times10^{14}$ DRP/lung in rhesus macaques by endobronchial delivery with a PennCentury Microsprayer™. Gene transfer and expression of the GFP transgene was detected by real time PCR and RT-PCR using the Light cycler (Roche). GFP transfer was 100× greater in these AAV2/5 studies at $1\times10^{6}$ copies/μg of DNA as compared with that achievable with AAV2. GFP RNA expression was present and quantified up to $2\times10^{5}$ copies/μg of cDNA. In comparison, RNA expression was only qualitatively detected by nested RT-PCR after AAV2 dosing.

FIG. 13 is a graphical representation of the results, showing copies of DNA in each lung region measured in monkeys infected with either single or repeated dosing of AAV2 or a single dose of AAV5-GFP. All data points represent the copies of DNA measured in each lung region, but boxes filled with black, red, or blue color (as indicated by shading in the boxed legend in the drawing) are those samples that were both positive for DNA and RNA transfer. As can be seen in FIG. 13, the treatment with single dose of AAV5-GFP is much more effective than with repeated or single AAV2.

High dose airway delivery of up to $2\times10^{14}$ DRP per animal was achieved without clinical toxicity or pathologic sequelae in nonhuman primates.

These studies show that higher doses delivered to the airways are feasible, nontoxic, and result in improved gene transfer. Regions with the highest gene transfer demonstrated quantifiable RNA expression.

Example 2

Recombinant adeno-associated viral vectors lack vector-induced inflammation and have the ability to integrate into a subject's genome. AAV-serotype 2 (AAV2) has been the serotype most utilized in clinical trials and feasibility has been confirmed with successful gene transfer. This Example describes the use of pseudotyped vectors, which use capsid proteins of other AAV serotypes.

Methods: AAV2/5 pseudotyped vectors were generated using the AAV2 ITRs with the AAV5 capsid proteins expressing 1) a truncated CFTR insert (Δ268) capable of reconstituting physiologic function or 2) an reporter insert, GFP, whose expression was driven by the chicken beta actin promoter (CBA).

AAV2/5 pseudotyped vectors with either the CFTR insert or the reporter insert, as a control vector, were administered at doses up to $1\times10^{14}$ DRP/lung in nonhuman primates by aerosolized bronchoscopic delivery with a Penn Century Microsprayer™. Animals were closely observed and sacrificed at day 21, at which time the lungs were sectioned (n=9) (consistent with prior scintigraphic deposition studies) and analyzed by quantitative real time PCR and RT-PCR using a LightCycler (Roche).

Results: Vector-specific CFTR gene transfer was present in all experimental animals and averaged $1.24\times10^5$ copies/μg of DNA. Vector-specific CFTR gene transfer was absent in 35/36 lung sections from control animals. RNA expression was not only present but also quantitatively measurable (~$2\times10^4$ copies/μg of cDNA). In contrast, previous studies using AAV2 resulted in only qualitative assessment of RNA expression. CFTR protein expression was detected by immunoprecipitation using M3A7, a murine monoclonal antibody directed against the C-terminus of CFTR, and visualized and analyzed through $^{32}P$ phosphoimaging.

High dose airway delivery of a pseudotyped AAV2/5 vector resulted in enhanced gene transfer and quantitative RNA expression as well as protein expression in non human primates without clinical toxicity.

Example 3

Juvenile rhesus macaques are obtained from the Johns Hopkins University breeding colony and housed according to Animal Care and Use Committee guidelines. All macaques are tested for simian immunodeficiency virus and Herpesvirus simiae (Herpes B), and are judged to healthy by the veterinarian before any procedure.

Radiolabeled saline and rAAV-GFP vectors are admixed with radiolabel. Three hundred μCi of the radioisotope 99mtechnetium (99 mTc) (Syncor, Baltimore, Md.) are chelated to diethylene-triamine penta-acetic acid (DTPA) and admixed with 3 ml of normal saline or with 3 ml of saline and rAAV-GFP vector. To ensure that the addition of the isotope and DTPA did not alter the viability of the vector, infectivity of Human Embryonic Kidney (HEK) cells treated with rAAV-GFP alone was compared to infectivity in cells that were treated with vector admixed with 99m Tc-DTPA-saline.

Cells are analyzed by fluorescence activated cell sorting (FACS) and by fluorescence microscopy. Cells that are infected with rAAV-GFP admixed with 99 mTc-DTPA showed the same level of expression as cells that were infected with rAAV-GFP alone.

Aerosol Delivery by Microsprayer™: 99 mTc-DTPA-saline (control) and 99 mTc-DTPA-saline-rAAV5-GFP (experimental arm) is delivered directly to the tracheobronchial tree using a MicroSprayer™ (PennCentury, Philadelphia, Pa.) inserted through a 3.5 mm flexible fiber optic bronchoscope (Olympus, Melville, N.Y.). In supine position, the macaques are sedated with ketamine and isofluorane, intubated with a 5.0 mm ETT, and ventilated with supplemental oxygen. Coughing is minimized by administering 1% lidocaine (3 mL) onto the carina. The bronchoscope is advanced through an adapter in the ETT and positioned in the proximal end of either the left or right main stem bronchus. Using direct visualization, the MicroSprayer™ is inserted through the suction channel and advanced approximately 3 mm beyond the distal tip of the scope. Care is taken to avoid airway trauma. Ten aliquots of approximately 150 μl each of 99 mTc-DTPA-saline or 99 mTc-DTPA-saline-rAAV5-GFP are sprayed into each mainstem bronchus. The entire procedure lasts a few minutes.

Example 4

This Example describes procedures used in a rhesus macaque model to evaluate whether AAV5 based vectors can increase gene transfer and expression of rAAV-GFP, and to assess the effect of AAV5 capsid antigens on transgene expression.

Gamma scintigraphy. In different animals, DNase resistant particles are admixed with 99MTc-DTPA-saline, deposited immediately through a microsprayer into each lung via bronchoscope, and quantified immediately by gamma scintigraphy. Only one dose is administered per animal, with each lung from the same animal receiving the same dose. In this method of delivery, uniform numbers of particles/gm of tissue are administered to most lung regions.

Scintigraphy documents the initial biodistribution of the vector dose in nine regions of each lung (18 regions/2 lungs per animal), as illustrated in FIG. 1. Experiments are done with cohorts of two animals, one animal at each dose. After two cohorts, data are analyzed to determine statistical significance (36 regions/cohort). A total of five cohorts is used. Exemplary vectors used for these studies are shown in FIG. 2.

Utilizing this technique, we have shown previously that uniform biodistribution of recombinant virus into the lung can be achieved and it is possible to quantify the initial regional dose of vector. Evaluating AAV5 at two doses demonstrates toxicity and dose dependent gene expression for a clinical trial. Utilizing AAV5 at doses higher than for AAV2 and one log lower also enables us to use significant statistical power to evaluate whether AAV5 leads to enhanced gene transfer and transduction. It is also valuable in evaluating potential toxicity at very high doses.

Figure 1A:
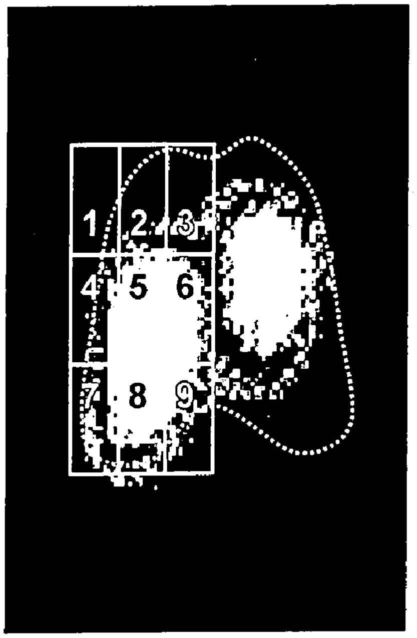
FIG. 1 depicts the determination of regional deposition, transduction, and expression of a reporter gene in a macaque subject. A nine-region grid was delineated on the 133Xe ventilation image (dotted line) and superimposed on the 99 mTc aerosol image of the macaque (1A and 1B). Three weeks after the administration of 99m Tc-rAAV-GFP by bronchoscopic microspraying, the lungs of the macaque were removed and divided into a nine-region grid. Data is shown for the right lung.

Vector is instilled at day 0 with 99 mTc-DTPA and three weeks later the lungs and heart are removed. In one study, lungs were infused with 60 cc of saline and divided into a nine-region grid per lung (FIG. 1A). These nine regions correlate the pathologic findings with the initial biplanar scintigraphic analysis. A thin slice of the cephalad portion of each of the nine regions (approximately 10% of the specimen) is preserved in 4% paraformaldehyde. The remaining 90% is flash frozen and weighed. Samples are assayed for GFP: DNA, mRNA, and protein. We have previously shown that in vivo recombinant GFP expression (void of Adenoviral helper) peaks at week 3 (Flotte 1998 Gene Therapy2:29-37).

The animals undergo bronchoscopy and BAL at days 0, 14, and at autopsy, to obtain samples for cytologic brushings of the bronchial epithelium in the proximal and distal segments. To assess humoral immune responses, blood is drawn (venopuncture, femoral vein) for CBC, ESR, anti-AAV5 antibodies, and serum IL-6 and IL-8 levels, and (BAL) fluid and nasal washes are obtained to determine neutralizing antibody titers and cell counts. Bronchoscopy and BAL procedures are spaced to allow any procedurally related inflammation to resolve before the next dosing procedure.

The animals also undergo arterial puncture (femoral artery) for arterial blood gas analysis and chest radiography to assess the clinical safety of AAV5 administration. After necropsy at day 30, lung tissue is assayed for evidence of inflammation (see Table 1 for classification of inflammation), and studies of DNA transfer, transduction, and protein expression are performed.

The animals are examined daily for clinical indices of toxicity. Common toxicity criteria can be stratified into the following categories:

1. No toxicity: no evidence of changes in respiratory rate, coughing, appetite, or activity.

2. Mild toxicity: evidence of slight increase in respiratory rate, slight cough, slightly less active and possibly a slight decrease in appetite.

3. Moderate toxicity: evidence of marked decrease in respiratory signs, pronounced cough, obviously less active, and a marked decrease in appetite.

4. Severe toxicity: evidence of marked decrease in respiratory signs, possibly including some degree of cyanosis, severe cough, obviously less active, and a severe decrease in appetite.

5. Life-threatening toxicity: marked evidence of cyanosis, failure to move about the cage, absent appetite, comatose.

After necropsy, and in a blind study, tissues are evaluated by a pathologist using the criteria outlined below, to characterize the presence and degree of inflammation. The animals are evaluated for tissue pathology and a pathology report is generated for each of the monkeys, which is represented below as Table 1:

TABLE 1

| Bronchial Associated Lymphoid Aggregates (BAL) | Present (+/−) | Diffuse/ Focal | % in 10 LPF (4X) |
|---|---|---|---|
| Bronchi w/ BAL | | | |
| BAL aggregates/bronchi | | | |
| Lymphocytic infiltrate in muscular sheath (non-aggregate) | | | |
| Bronchi w/ diffuse lymphocytic infiltrate | | | |
| BOOP-focal organizing acute and chronic peribronchiolar inflammation | | | |
| Bronchi w/ BOOP | | | |
| PMN's in alveolar spaces | | | |
| PMN's in bronchi or muscular sheath | | | |
| Perivascular inflammation | | | |
| Vessel Involvement (%) | | | |
| Necrosis-Large or small vessel-Artery or vein | | | |
| Eosinophils: Perivascular or peripheral | | | |

Example 5

This Example describes dosing regimens and protocols that can be used, e.g., for testing gene therapy methods in accordance with the invention.

To evaluate the effects of repeated dosing of AAV5 based vectors, we utilize information from the single dose experiments with regard to planned dosing. Using a similar protocol for vector instillation, two doses of AAV5-CFTR are applied to each of four monkeys at 0 and 30 days, followed by a single dose of the gene therapy particles of AAV5-GFP at day 60. The final dose of AAV5-GFP is admixed with the radioisotope Tc99m to correlate initial dose deposition with actual gene transfer. Table 2 depicts the experimental design.

TABLE 2

| | Expression Studies (Day) | | | |
|---|---|---|---|---|
| | 0 | 30 | 60 | 90 |
| Experimental Design (Vector Dosing) | AAV5-CFTR | AAV5-CFTR | AAV5-GFP | |
| Brushings for DNA PCR & RT-PCR | X | X | X | X |
| Autopsy for DNA PCR, RT-PCR, & in situ PCR, GFP or CFTR Immunology Studies | | | | X |
| Serum/BAL Antibody titers BAL | X | X | X | X |
| BAL: IL6 & IL8 | X | X | X | X |
| Lung Samples for pathology | | | | X |
| Clinical Studies (daily status assessment) | | | | |
| Physical Exam, Blood Chemistries, X-Ray | X | X | X | X |
| Clinical Pathology (see Table 1) | | | | X |

Example 6

This Example describes several tests useful, e.g., in monitoring effect of gene therapy using vectors in accordance with the invention.

Bronchial Mucosal Brushings. Cytologic brushings of the bronchial mucosa are accomplished using a 1×2 mm cytology brush (Mill Rose Lab), which is passed through the bronchoscope and gently brushed against the mucosa in the approximate area that the vector is instilled. The brushes are incubated at 37° C. for 60 minutes in serum-free media with 50% trypsin to isolate the collected cells. The cells are centrifuged at 800 RPM for 5 minutes and then resuspended in PBS for FACS analysis and cytospin.

The cytospin slides are examined for GFP expression by fluorescence microscopy and hCFTR expression by in situ PCR. Fresh BAL are analyzed for cell counting by placing 10 ml onto a cell counting chamber slide and recording the number of cells per $mm^3$. Slides for cell counts and differentials are prepared by centrifuging 100 ml of fresh BAL onto a microscope slide using a Shandon Cytospin-3 centrifuge at 500 rpm for 5 minutes, fixing in 1% gluteraldehyde, and staining with Wright-Giemsa stain. Differential analysis is performed on 100-300 cells per slide, and the percent polymorphonuclear cells per total cells counted is recorded. The remainder of the BAL are flash frozen and stored at −80° C. for analysis of IL-6 and IL-8 levels by ELISA (R&D Systems). The samples are also tested for neutralizing antibodies.

Lung Deposition Images. Immediately following the administration of 99 mTc-DTPA-saline-rAAV5-GFP aerosol, anterior lung images are obtained using a large-field-of-view gamma camera (Siemens Gammasonics, Inc., Des Plaines, Ill.). Images are acquired and analyzed with a computer (SMV, Twinsburg, Ohio). Analyses include total lung deposition fraction per each lung and regional lung deposition fraction.

Lung Deposition Fraction. To quantify deposition fraction, two additional images are acquired for each macaque prior to aerosol delivery. A transmission image is acquired to quantify the extent to which the thickness of each macaque's thorax can attenuate gamma radiation. The sedated monkeys are seated in the restraining chair facing the gamma camera. A plastic box, filled with water and 99 mTc, is positioned behind the macaque's thorax. An anterior lung image and a subsequent image of the box without the macaque is acquired. The number of counts of gamma emissions, within a representative region in the two images, is quantified and expressed as the ratio of the "counts" with and without the macaque to normalize for the individual attenuation of each macaque. A ventilation image taken, for example, with 133 Xenon gas determines the functional lung borders. The sedated macaque, seated in a restraining chair facing the camera, spontaneously inhales 133Xenon (133Xe) gas through a tight fitting anesthesia mask. 133Xe gas is re-circulated by means of a Pulmonex Xenon System (Biodex Medical Systems, Shirley, N.Y.). After attaining equilibration, an anterior lung image is acquired. The functional lung border, as defined by the 133Xe image (dotted lines in FIG. 1A), is superimposed on the subsequent 99 mTc-aerosol lung image.

Total lung deposition is quantified in microcuries, using the equation of Macey and Marshall, which incorporates the number of counts within the functional lung border (the ventilation image), the transmission value and a camera sensitivity value. The microcuries of 99 mTc measured within the lung borders is divided by the initial microcuries in the nebulizer cup or Microsprayer syringe, and expressed as percent of initial activity (deposition fraction).

Regional Deposition per Lung. Using the functional lung borders defined by the 133Xe ventilation image, the maximum height and width of the lung is divided into thirds, creating a nine-region grid that is superimposed on the 99 mTc aerosol image of each macaque. The amount of 99 mTc in each region is calculated in the same way that the lung deposition fraction is calculated and is expressed as a percentage of the initial activity in the nebulizer cup or Microsprayer™ syringe. We have used this approach previously to quantify regional aerosol deposition.

Transduction and Expression. Both lungs and other organs are removed. Each lung is infused with 60 cc of saline and divided into a nine-region grid as shown schematically in FIG. 1. A thin slice of the cephalad portion of each of the nine regions (approximately 10% of the specimen) is preserved in 4% paraformaldehyde. The remaining 90% is flash frozen and weighed.

DNA, RNA and Protein Quantitation. Quantitative PCR is used to test for GFP-specific DNA. Lung tissue specimens are homogenized with a frozen, sterilized mortar and pestle, and the homogenate is equally divided for RNA and DNA extraction. RNA extractions are performed using Trizol Reagent (Life Technologies, Rockville, Md.). Genomic DNA is isolated from lung samples and non-target organs using a mini-prep kit (Blood and Cell Culture DNA Midi Kit and DNeasy Tissue Mini Kit, respectively, Qiagen, Valencia, Calif.).

GFP-specific DNA is measured using real-time PCR (LightCycler Roche Molecular Biochemicals, Indianapolis, Ind.). Primer pairs are:

```
5'(5'-ATGTGCAGGAGAGAACCA TCT-3')   (SEQ ID NO: 2)
and

3'(5 '-GCCATTCTTTTACTTGTCGGC-3').  (SEQ ID NO: 3)
```

Ten-fold dilutions (1 pmol to 0.1 fmol) of GFP plasmid (pTR-UF5) in rhesus genomic DNA (25 ng/μl) are used as controls. The lower limit of detection, 0.1 fmol of the standard, is calculated to equal 9.6 copies of the plasmid per reaction. Melting curves are used to identify the product (Tm=84° C.) formed during each reaction. Tissue to be analyzed includes the visceral organs (liver, pancreas, kidney), GI tract (stomach, duodenum, jejunum, colon) thymus, heart, trachea, tracheal lymph nodes, pharynx, larynx, esophagus, tongue, spleen, bronchial lymph nodes, brain, muscle, gonads, and mesenteric lymph nodes.

DNase-treated (Life Technologies) RNA (6 μl) is divided into RT− and RT+ samples. RT+ samples are treated with reverse transcriptase and undergo cDNA synthesis using the First-strand cDNA Synthesis Kit (Amersham Pharmacia Biotech, Piscataway, N.J.); RT− samples are not treated with reverse transcriptase. Both RT+ and RT− samples undergo PCR to detect β-actin using the sequence specific primers:

```
5'(5'-TAAAGACTCTATGC CAACACAGT-3')   (SEQ ID NO: 4)
and

3'(5'-CACGATGGAGGGGC CGGACTCATC-3')  (SEQ ID NO: 5)
(product size: 240bp).
```

The RT− and RT+ samples are also used in nested PCR. The first round of PCR contains the primer pair:

```
5'(5'-TCTCTTATGGCGTGCAGTGCT-3')   (SEQ ID NO: 6)
and

3'(5'-TGGAGTGTTCTGTTGATAATG-3'),  (SEQ ID NO: 7)
```

and PCR Supermix (Life Technologies). Cycling is conducted with the GeneAmp PCR System 2400 (Perkin Elmer, Wellesley, Mass.). The nested round consists of amplification of 4 μl of the first round product using the same primer pair used in the quantitative PCR described above. PCR products for rounds 1 and 2 are 371 bp and 205 bp, respectively. RT+ samples are considered positive for vector RNA only if the following criteria are met: 1) presence of the 371 bp and/or the 205 bp GFP product from first and second rounds of RT-PCR, respectively; 2) presence of β-actin product in the RT+ reactions; and 3) absence of β-actin product in the RT− reactions. To eliminate false positives, negative samples (including control animal) have an absence of GFP products for both rounds of nested PCR and the presence of the β-actin product in the RT+ reactions.

Lung samples positive for RNA expression are analyzed by Western Blot for protein expression. The proteins are separated by 12% SDS-PAGE and transferred to PVDF membranes. The membranes are then blocked, washed, and incubated with the same primary antibody, Ab 6556 (Abcam, Cambridge, UK), and a secondary donkey anti-rabbit HRP-conjugate antibody (Amersham Life Science, Arlington Heights, Ill.) was used in the same manner as described above.

Protein Detection. Multiple transverse 5-micron sections are made through each of the nine regions perpendicular to visible bronchi or bronchioles when possible. We first examine unstained sections for GFP green fluorescence using confocal microscopy (PerkinElmer UltraView LCI (Live Cell Imaging) System; Perkin Elmer Life Sciences Inc., Boston, Mass.) and are processed using Dell Optiplex 400 computer, UltraView software (Perkin Elmer Life Sciences Inc., Boston, Mass.).

The same samples are also tested by immunohistochemistry using a purified rabbit polyclonal antibody to GFP, Ab 6556, as described above. The secondary antibody is a goat anti-rabbit IgG antibody conjugated to Cy3 (red) (Jackson ImmunoResearch Laboratories, Inc., West Grove, Pa.). Samples are visualized using confocal microscopy.

IL-6 and IL-8 Assays. Inflammatory cytokines such as IL-6 and IL-8 are markers of inflammation induced by viral particles. BAL fluids are analyzed for IL-6 and IL-8 by ELISA (R&D Systems). The concentrations are normalized to the amount present in the epithelial lining fluid (ELF) using the urea nitrogen (UN) concentration of the BAL fluid to correct for dilution effects. For example: $(IL\text{-}6_{ELF})=IL\text{-}6_{BAL}\times UN_{blood}/UN_{BAL}$.

Antibody response to AAV5 and neutralizing antibody titers. To assess the response of the humoral component of the immune system, neutralizing antibody titers are determined. Serial two-fold dilutions of sample (serum or BAL fluid) are incubated with serial ten-fold dilutions of rAAV5 in a 96 well dish and added to parallel wells of Ad-infected HeLa cells (m.o.i.=2). After 48 hours the number of fluorescent cells are counted. GFP fluorescence on Ad-infected HeLa cells without sera or BAL represent the positive control. Neutralizing titers are reported as the dilution corresponding to a 50× decrease in fluorescence.

Statistical Analysis. Total deposition, regional deposition, and regional vector transfer are reported as mean+standard deviation. A Kruskal-Wallis one-way analysis of variance test is used to assess the statistical significance of deposition fraction, vector dose, and vector transfer. A Spearman rank-order correlation test is used to assess the relationship between regional gene transfer and vector dose. A Fisher exact test is used to assess expression as a function of dose. Non-parametric tests are used because the data are not normally distributed. P values are significant at $\leqq 0.05$.

Evaluating the design effect, standard deviation, number of animals, and lung regions, we have determined that the statistical power is about >0.8 to determine differences in gene transfer one log between experimental maneuvers such as dose, vector serotype, and promoter strength. Notably, we have conservatively chosen a two log difference in dose and expect at least a ½ log difference in transduction. Data is based on an experiment of 4 animals per maneuver, with nine lung regions per lung (see FIG. 1) for a total of 72 lung regions. Intraclass correlation of the monkey effect with respect to copy number per lung region is approximately 0.07 for the single dose and 0.00132 for the multiple dose experiments. Because these values are low, a small number of monkeys and multiple lung regions may be used.

Example 7

This Example provides detailed methodology for immunoprecipitating CFTR protein from cell lysates and studying phosphorylation of CFTR protein in vitro.

Biochemical analysis of CFTR is performed by immunoprecipitation with the mouse monoclonal anti-CFTR antibody, M3A7 (Upstate), made to residues 1370-1380 in NBD2 followed by in vitro phosphorylation using protein kinase A and γ32P-ATP (see FIG. 3). Briefly, tissue is harvested and scraped into lysis buffer (20 mM HEPES pH 7.0, 150 mM NaCl, 2 mM EDTA, 1% Nonidet P40) containing 1 mM β-glycerol phosphate, 1 mM L-phenylalanine, 1 mM sodium orthovanadate, 50 mM sodium fluoride and the following protease inhibitors: pepstatin A 2 μg/ml, leupeptin 10 μg/ml, aporotinin 10 μg/ml, elastinal 4 μg/ml, nzamidine 0.5 mg/ml, 1 mM phenylmethane-sulfonyl fluoride, 0.4 mM iodoacetic acid, 2.5 mM phenanthroline and 0.1 mM TPCK (N-tosyle-L-phenylalanine chloromemethyl ketone) (all from Sigma).

Tissue is homogenized and lysed on ice for 60 min and centrifuged for 30 s at 10,000×g in an Eppendorf bench top centrifuge. The protein in the supernatant is quantified with BCA protein assay kit (Pierce, Rockford, Ill.) and stored at −80° C. One milligram of protein lysate is placed into a 1.5 ml Eppendorf tube containing enough lysis buffer with protease inhibitors to ensure equal volumes between different samples. The lysate is precleared by addition of 30 μl Protein A sepharose beads (Amersham Pharmacia) and incubated at 4° C. for 2 hrs. Subsequently, 2 μg of M3A7 monoclonal antibody is added and incubated at 4° C. overnight.

To pull down the antigen-antibody complex, the same amount of Protein A beads are added to each reaction and incubated at 4° C. for 2 h. The antigen-antibody-antibody complex is pelleted by a brief spin and washed 5 times for 10 min with lysis buffer. The immunoprecipitates are then washed once with Tris-buffered saline pH 8.0 and incubated with 5 units of the catalytic subunit of protein kinase A (Sigma) and 10 μCi γ32P-ATP (NEN-Dupont, Boston, Mass.) in 50 μl of PKA buffer (50 mM Tris, pH 7.5, 10 mM MgCl2, 0.1 mg/ml BSA) at 30° C. for 1 hr. Following two washes with lysis buffer, the immunoprecipitates are resuspended in 40 μl Laemmli sample buffer (BIO-RAD, Hercules, Calif.) and incubated at 65° C. for 4 min. The sample is spun for 2 min at 10,000 rpm, and the supernatant is stored at −20° C. overnight or loaded directly onto a gel.

The proteins are separated on a 5% SDS-polyacrylamide gel (BIO-RAD) and prepared for autoradiography. Exposure time is 30-60 min at −80° C. Radioactivity associated with the CFTR is quantified with phosphorimage analysis on a Fuji camera (Fuji).

Example 8

This Example describes exemplary methods useful for constructing plasmids comprising CFTR or biologically active fragments of CFTR, as well as reporter proteins, in accordance with the invention.

The rAAV-CB-Δ264CFTR vector utilizes the N-terminal deleted Δ264CFTR gene paired to a chicken beta actin (CB) promoter with intron-exon sequences (324 bp) prior to the ATG translation initiation site added to increase expression.

Plasmid pAAV-CB-Δ264CFTR was constructed by the following method. The Δ264CFTR gene was synthesized by PCR from pSA313 (a 7519 bp plasmid containing a full-length CFTR poly-adenylated gene in a Bluescript backbone), using SpeI/Kozak sequence engineered primers 5' to the ATG codon at bp position 792 and 3' to the poly-adenylation signal, yielding a 3,769 bp fragment. The resultant DNA was cut with the restriction enzymes SpeI and SnaBI (a blunt-end cutter). The 3736 bp fragment insert was then gel-purified (Qiagen gel extraction kit).

The CB backbone fragment was cut out of pTR2-UF12.1, (a 6,008 bp plasmid containing the CB enhancer-promoter hybrid with intron-exon sequences, AAV ITRs (serotype 2), origin of replication, and ampicillin resistance gene), with SpeI, followed by a BglII partial digestion. This was then gel purified (Qiagen gel extraction kit) to yield a 4,202 bp backbone fragment. The backbone fragment was subsequently treated with calf intestinal alkaline phosphatase (CIP) to remove 5' phosphate groups.

The insert and backbone fragments were then ligated (T4 DNA ligase) at a 10:1 molar ratio to yield a 7,934 bp linear fragment. The reaction mix was then treated with T4 DNA polymerase to fill-in the 5' BglII over-hang, and a blunt-ended intramolecular ligation (T4 DNA ligase) was performed to create the circular 7,934 bp plasmid, pAAV-CB-Δ264CFTR. The expression cassette was then sequenced and the integrity of the ITRs was confirmed by restriction analysis with SmaI and AvaI.

The 7,934 bp pAAV-CB-Δ264CFTR plasmid was subsequently grown in bulk culture and CsCl purified, to be used either by direct transfection, or it was packaged into infectious rAAV gene therapy particles, as further described infra. This construct yields 5,060 bp of packaged sequence. The rAAV gene therapy particles, as described above, are exemplary of the AAV gene therapy particles of the invention.

Similar methods were used to derive the luciferase constructs depicted, e.g., in FIG. 4.

The pAAV-CB-luc/EYFP vector utilizes a luciferase/enhanced yellow fluorescent protein (EYFP) fusion gene paired to the CB promoter with intron-exon sequences (324 bp) prior to the ATG translation initiation site added to increase expression.

The pAAV-CMVeRSVp-luc/EYFP vector utilizes the same luciferase/enhanced yellow fluorescent protein (EYFP) fusion gene paired to the 395 bp Rous Sarcoma Virus (RSV) promoter and the 380 bp CMV enhancer element.

The pAAV-RSV-luc/EYFP vector utilizes the same luciferase/enhanced yellow fluorescent protein (EYFP) fusion gene paired to the 395 bp Rous Sarcoma Virus (RSV) promoter.

Plasmid pTR2-CB-luc/EYFP. Plasmid pTR2-RSVp-luc/EYFP was constructed by restricting the CMVe enhancer sequence out of the pAAV-RSVpCMVe-luciferase/EYFP construct by first cutting with Acc65I and religating the plasmid ends.

For the nuclear-targeted lacZ experiments, these were packaged rAAV2 or rAAV5 versions of an RSV promoter-driven, nuclear-targeted lacZ vector.

Example 9

This Example describes methods for producing pseudotyped rAAV viral vectors useful for gene therapy, in accordance with the invention. The methods include packaging rAAV plasmid vectors (for example, plasmids as shown in FIG. 4, such as pAAV-CB-Δ264CFTR comprising nucleic acid sequence encoding a biologically active truncated CFTR sequence and an enhanced CB promoter flanked by AAV2 ITR sequences) into rAAV viral vectors comprising heterologous capsid proteins, such as AAV5 Cap proteins.

The AAV-CB-Δ264CFTR plasmid as described in Example 8 supra was packaged using pseudotyping techniques described in Zolotukhin S, Potter M, Zolotukhin I, Sakai Y, Loiler S, Fraites T J, Jr., Chiodo V A, Phillipsberg T, Muzyczka N, Hauswirth W W, Flotte T R, Byrne B J, Snyder R O: Production and purification of serotype 1, 2, and 5 recombinant adeno-associated viral vectors. Methods 2002; 28: 158-67. Briefly, the rAAV2-ITR-containing vector plasmid was co-transfected into cultures of HEK-293 (Ad2 E1a/E1b-positive) cells, along with a pDG5 helper plasmid containing the AAV2 Rep gene, AAV5 Cap gene, and Ad5 E2a, E4 and VA-RNA genes.

Vector particles were released by serial-freeze thaw and processed by iodixanol step gradient centrifugation. The physical titer (in vector genomes, vg) of the above vector preparations was determined using DNA dot-blot hybridization.

Example 10

This Example describes culture conditions and transfection methods useful for testing of vectors in accordance with the invention in IB3-1, a cystic fibrosis (CF) bronchial epithelial cell line.

Cell transfection. IB3-1 cells were seeded at $3\times10^5$ cells per well in 35 mm wells, 24 hours prior to transfection. The cells were then washed and transfected with a mixture of Fugene, serum free media and plasmid of interest and incubated for 5 hours at 37° C. One set of cells was mock transfected with no vector DNA. The transfection media was then aspirated and new media with serum and antibiotics was added to the cells and allowed to incubate at 37° C. for 48 hours. Cell lysates were then harvested and assayed for luciferase activity.

Example 11

This Example describes a reporter gene assay based on luciferase that is useful to monitor distribution of rAAV vectors comprising luciferase constructs as reporter genes, and for determining expression levels of transgenes in tissues obtained from subjects after administration of gene therapy vectors.

Luciferase Assay. Frozen lungs from animal subjects described in Examples herein were individually pulverized into a fine powder by mortar and pestle. 500 μl of Promega "lysis buffer" was added to each tube containing a homogenized lung sample, and the samples were vortexed for 15 minutes. The samples were then frozen and thawed three times using alternating liquid nitrogen and 37° C. water baths. This was followed by a 3 minute centrifugation at 10,000×g. The supernatant was transferred to another 1.5-ml tube and the extraction process repeated (without freeze-thawing) after adding another 500 μl of lysis buffer to the pellet. The first and second supernatants were then combined and assayed for luciferase with the Promega Luciferase Assay System and protocol.

Example 12

This Example describes the methodology for an assay (chloride efflux and excised inside-out patch clamp assay) that can be used to identify IB3-1 cells that have been successfully transduced with a rAAV plasmid expressing a functional CFTR gene product. More particularly, $^{36}Cl^-$ efflux assays were used to screen for CFTR activity in transfected IB3-1 clones. The CFTR ion channel specific properties were determined in positive clones by patch clamping methods.

Transfected stable clones were established through co-transfection of pAAV-CB-Δ264CFTR with pTR2-UF11, that contains screenable (GFP) as well as selectable (neomycin resistance) markers. This transfection was performed at a pAAV-CB-Δ264CFTR to pTR2-UF11 ratio of 10:1, to make it likely that clones screened and selected for the presence of pTR2-UF11 would also carry the TR2-CBA-Δ264CFTR construct.

Clones were then screened for ability to efflux $^{36}Cl^-$ by loading them with the radioisotope, followed by multiple wash steps to remove extracellular isotope, and then taking a series of media samples prior to and after the addition of a CFTR agonist mixture. These samples were then measured in a scintillation counter.

The mathematical difference between the maximal post-agonist % efflux rate and the minimal % efflux rate prior to that efflux event is defined as the "change in % efflux." Cells without significant CFTR activity will not stimulate upon exposure to agonist mixture and will display a negative "change in % efflux."

Excised inside-out patch clamping was utilized to confirm the radioisotope efflux activity as that of CFTR. pAAV-CB-Δ264CFTR stable transfectant IB3-1 clones, wild-type IB3-1 cells (negative control), and a full length CFTR corrected IB3-1 cell derived cell line (positive control) were grown on coverslips. Symmetrical 145 mM Tris-Cl solutions were used to study $Cl^-$ currents exclusively. To activate the CFTR chloride channel, 75 nM PKA and 1 mM ATP were added to cytoplasmic solution. Only patches that contained a single active channel were measured. The presence of single channel patches was ascertained by the absence of multiple simultaneous openings over the 15-45 minute time course of the experiment.

Example 13

This Example describes methods for using an inflammatory lung disease in a rodent model (CFTR−/− mouse) challenged with *Pseudomonas* to test vectors in accordance with the invention.

In challenge experiments, CFTR−/− mice were treated with rAAV5-CB-Δ264CFTR vector, rAAV5-UF11 (GFP) vector or PBS, and housed in SPF conditions for six weeks, and then challenged with 50 μl of an approximately 50% *Pseudomonas*-bead mixture (as determined by 30 minute gravity sedimentation) of $OD_{600}$ 2.0. Mice were randomized with regard to injection order to avoid any unrecognized systematic error. Weights were recorded at time of challenge and at time of sacrifice on day 4. Weight loss was expressed as the weight lost over the four day IT *Pseudomonas* challenge divided by the original day 0 weight, multiplied by 100. A blind histopathologic analysis of hematoxylin-eosin stained sections of formalin-fixed, paraffin-embedded lung tissue samples taken at the time of sacrifice, was performed by a pathologist.

Example 14

This Example describes studies to determine relative promoter efficiency in gene therapy constructs in a CF bronchial cell line.

To determine the relative transcriptional activity of the CB hybrid promoter in cell types relevant for CF gene therapy, transfection experiments were performed in the IB3-1 CF bronchial epithelial cell line, described above. An rAAV-CB-luciferase vector (rAAV-CB-luc/EYFP) was transfected into cultures of IB3-1 cells and the levels of luciferase expression were measured in the cell lysates using a standard assay. The expression levels were then compared with those observed with either an RSV-long terminal repeat (LTR) promoter, or with a CMV enhancer/RSV promoter hybrid, as shown in FIG. 4.

Referring to FIG. 5, it was seen that the cassette comprising the CB hybrid promoter was the most efficient among the promoters tested.

Example 15

This Example describes results of a comparison of expression levels of a reporter gene in IB3-1 cell line transduced with rAAV serotypes 2 and 5.

We compared an alternate serotype with the original rAAV2 in the IB3-1 CF bronchial epithelial cell line. A nuclear-targeted beta-galactosidase reporter was used (Table 3). As the table indicates, the relative efficiency was 10-fold higher with rAAV5 capsid in comparison with the rAAV2 capsid in IB3-1 cells, although both were low under these conditions (2.7% vs. 0.26%).

TABLE 3

| Vector | Mean Number of Positive Cells (%) |
|---|---|
| AAV2-nLacZ | 13 (0.26%) |
| AAV5-nLacZ | 137 (2.7%) |
| | $p < 0.00003$ |

Table 3 shows the relative in vitro transduction efficiency of IB3-1 cell cultures with rAAV-RSV-nlacZ vectors at a multiplicity of infection of 500 particles per cell. The mean is the number of positive cells per microtiter well (approximately 5000 cells).

Example 16

This Example describes results of a functional assay for CFTR-mediated chloride efflux in IB3-1 CF bronchial epithelial cells transduced with plasmid rAAV5-CB-Δ264CFTR expressing a truncated biologically active fragment of CFTR.

We screened clones of the IB3-1 CF bronchial epithelial cell line that had been transfected or transduced with rAAV5-CB-Δ264CFTR with a $^{36}Cl^-$ isotope tracer efflux assay, described above. In this assay, the increase in percent efflux after a cAMP agonist cocktail is used as an indicator of CFTR functional activity.

FIG. 6A shows cultures of CF bronchial epithelial IB3-1 cells (negative control), T84 cells (positive control), or pAAV-CB-Δ264CFTR-transfected IB3-1 cells loaded with $^{36}Cl^-$ and then monitored for isotope efflux before and after addition of a CFTR-specific cAMP-agonist cocktail. The percent increase in efflux after addition of agonist is depicted. Referring to FIG. 6A, uncorrected IB3-1 cell cultures showed a slightly negative change in percent efflux. IB3-1 cell populations transfected with the rAAV5-CB-Δ264CFTR showed a significant increase in CFTR-mediated chloride efflux. N=6 for each condition. P values are vs. IB3-1.

FIG. 6B depicts similar cAMP-stimulated chloride efflux values in IB3-1 cells transduced with packaged rAAV-CB-Δ264CFTR virions or particles, at particle multiplicities of 100 or 10,000 vector genome particles per cell. As shown in FIG. 6B, there was a dose-response relationship among the transduced clones, with increasing multiplicity of infection correlated with increasing magnitude of cAMP-activated chloride efflux. N=6 for each, P values are vs. IB3-1.

For comparison, a positive control cell line, T84, is depicted. This colonic adenocarcinoma-derived cell line is known to overexpress CFTR at approximately 4 times physiologic levels of normal cells (Flotte T R, Afione S A, Solow R, Drumm M L, Markakis D, Guggino W B, Zeitlin P L, Carter B J: Expression of the cystic fibrosis transmembrane conductance regulator from a novel adeno-associated virus promoter. J Biol Chem 1993; 268: 3781-90). Referring to FIG. 6B, the transduced clones exceeded the levels of chloride efflux seen in T84, suggesting that CFTR expression is very robust from this construct. By way of comparison, the first rAAV2-CFTR vector described by our laboratory indicated $^{36}Cl$-efflux at approximately one-half of the level of T84 by transfection, which is 2-fold higher than T84 at best by infection (Flotte, PNAS, 1993).

To confirm this result, the CFTR mRNA levels were compared semi-quantitatively using RT-PCR. FIG. 7 depicts the results of reverse transcriptase (RT)-PCR analysis to detect vector-derived CFTR mRNA after transduction of IB3-1 cells with rAAV-CB-Δ264CFTR. FIG. 7A shows negative images of ethidium bromide stained agarose gels showing an RT-PCR product of the predicted size. The levels compared favorably with that seen in the T84 control cell line (FIG. 7). A low baseline level of mRNA in untransduced IB3-1 cells is as previously observed with this cell line. FIG. 7B demonstrates that the band is not present without active RT, thus ruling out the possibility of DNA contamination of these DNase-treated, dT-column purified RNA extracts.

To definitively identify the cAMP-activated chloride efflux activity as CFTR, excised, inside-out patch clamp analysis was performed as described above. FIG. 8 depicts results of this analysis in IB3-1 cells transfected either with full length CFTR (8A, 8B) or the pAAV-CB-Δ264CFTR construct (8C, 8D). In the current vs. time plots (8B and 8D), channel openings appear as step-like downward deflections in the panels after application of a CFTR-specific cAMP agonist cocktail.

Figure 8A:
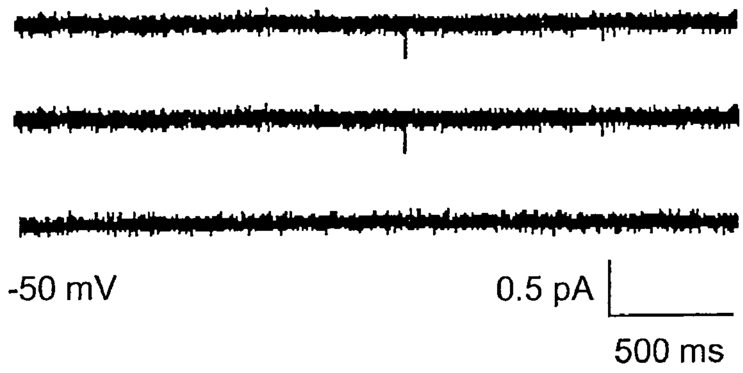
Figure 8B:
Figure 8C:
Figure 8D:

After treatment with a cAMP cocktail, channel openings were observed in the rAAV5-CB-Δ264CFTR-transfected IB3-1 cells (FIGS. 8C and 8D). The characteristics of this channel were similar to that seen with transfection of full-length wild-type CFTR (FIGS. 8A and 8B). Although the wild type CFTR control in this example was RSV-promoter-driven, the data with the previous rAAV2-CFTR was essentially indistinguishable (Egan, et al., 1992). There was a linear current-voltage relationship with a conductance of approximately 10 pS, which is typical for CFTR (data not shown). These studies confirmed the identity of the chloride channel activated within the rAAV5-CB-Δ264CFTR-treated cells.

Example 17

This Example describes results of a study demonstrating correction of the CF lung disease phenotype in vivo in a CFTR−/− mouse model of CF.

While in vitro studies are suitable for identification of correction of the chloride channel defect in CF, the relationship between CFTR chloride channel activity and the lung disease phenotype in CF patients is not entirely clear. We utilized a well-characterized CFTR−/− mouse strain that had gut-specific transgenic CFTR rescue to determine a specific correlation between transgene expression and correction of a CFTR phenotype in vivo and to enhance viability of the mice in a *Pseudomonas aeruginosa* (PA01 strain) agarose bead airway challenge paradigm.

It has previously been established that these mice have a greater degree of weight loss and mortality by 4 days after PA01 challenge (Heeckeren A, Walenga R, Konstan M W, Bonfield T, Davis P B, Ferkol T: Excessive inflammatory response of cystic fibrosis mice to bronchopulmonary infection with *Pseudomonas aeruginosa*. J Clin Invest 1997; 100: 2810-5). Weight was the primary indicator of successful amelioration of the CF defect.

FIG. 9 shows the results of an RT-PCR reaction which demonstrates CFTR mRNA expression in the lungs of rAAV5-CB-Δ264CFTR-treated CF mice. The RT-PCR was performed on whole lung RNA samples in a manner analogous to that presented for cell line mRNA in FIG. 7. In an initial experiment, matched groups of four CF mice were successfully treated with rAAV5-CB-Δ264-CFTR, as evidenced by RT-PCR (FIG. 9). More particularly, the CFTR-specific band is shown in the upper panel, and a GAPDH control, to demonstrate the presence of intact mRNA in each sample, is shown in the bottom panel. Lung RNA samples from three independent saline-injected control animals are shown on the left half of the figure ("control" lanes), while lung RNA samples from three vector-injected animals are shown on the right half (rAAV5-CFTR).

Animals were injected intratracheally with $1.2\times10^{11}$ VG of the rAAV5-CB-Δ264CFTR vector, and six weeks later were challenged with a *Pseudomonas aeruginosa* (PA01)-agarose bead slurry, using the van Heeckeren protocol. As has been previously seen with this model, the PBS-control CFTR −/− mice lost approximately 25% of their body weight by day 4 after PA01 challenge, while the rAAV5 vector-treated animals lost only 9.5% of their body weight. Stated another way, the weight loss was 2.5-fold greater in the control mice than it was in the vector-treated animals (Table 4).

TABLE 4

| Treatment Group | % Weight Loss |
|---|---|
| PBS | 24.7 ± 2.8 |
| Vector | 9.5 ± 12.5 |
| | p = 0.05 |

Table 4 shows prevention of weight loss by rAAV5-CB-Δ264CFTR pretreatment prior to PA01 challenge.

Unexpectedly, in these same mice, there was a dramatic difference in the histopathology of the lung tissue. Referring to FIG. 10, the [top] six panels show randomly-selected, representative fields of hematoxylin-eosin stained lung sections from PBS-treated control CFTR −/− mice 3 to 4 days after *Pseudomonas* challenge. The [bottom] six panels show similar fields from animals pre-treated with rAAV5-CB-Δ264CFTR. Untreated animals showed severe inflammatory infiltration of the airways and focal disease in the lung parenchyma. Neutrophils were very prominent in the airways, as was type II pneumocyte hyperplasia. One change that was seen exclusively in the untreated mice was dilatation of the non-cartilagenous airways, i.e., bronchiolectasis, a change very reminiscent of the small airways pathology in CF patients.

By contrast, this finding was non-existent in the vector-treated animals. To confirm the magnitude of these changes, the mice were scored independently, in a blinded manner, by a veterinary pathologist (Table 5).

TABLE 5

| Histologic Finding/Group | PBS | Vector | p |
|---|---|---|---|
| Endobronchial PMN (% affected) | 92.5 | 34.0 | 0.013* |
| Endobronchial PMN (severity) | 3.8 | 2.5 | 0.057+ |
| Peribronchial PMN (severity) | 3.5 | 2.0 | 0.029+ |
| Parenchymal loss (%) | 62.5 | 20.0 | 0.057+ |
| Ttype II pneumocyte hyperplasia (severity) | 2.0 | 1.0 | 0.029+ |
| Bronchiolectasis | 3 of 4 | 0 of 4 | |

Table 5 shows the histologic scoring of airway inflammation and prevention of pathologic changes by vector rescue.

Because of the reported variability of this model, we chose to reproduce the entire experiment, in this case increasing the number of rAAV5-CB-Δ264CFTR-treated animals to seven, and using a more appropriate control group, a rAAV5-CB-waited 10 weeks after intratracheal vector administration before challenging with PA01. Mice were then weighed daily for three days prior to sacrifice.

Although histologic changes were milder in these shorter-term (3 vs. 4 day) cohorts and did not differ appreciably between groups, the degree of weight loss was once again highly significantly different between the two groups on days 1 and 2 post-challenge, with a maximum loss of 23% in the GFP control group vs. approximately 15% in the vector-treated group (FIG. 11). The difference was no longer statistically significant by day 3. Nonetheless, the vector-rescued group again showed definite evidence of phenotypic correction by rAAV5-CB-Δ264 CFTR, based on the primary end point of weight loss.

Example 18

This Example describes a mouse model of allergic bronchopulmonary aspergillosis (ABPA) based on a CFTR knockout mouse.

In order to gain insight into aberrant cytokine regulation in cystic fibrosis (CF), we compared the phenotypic manifestations of allergen challenge in gut-corrected CFTR-deficient (CFTR 489x−/−, FABP-hCFTR+/+) mice and in background matched C57B16 (B6) mice. *Aspergillus fumigatus* (Af) antigen was used to mimic ABA, a peculiar hyper-IgE syndrome with a remarkably high prevalence in CF patients.

Methods:

CFTR knockout B6 and FVB/NJ mice (N=5) were sensitized with 20 ug of Af antigen by two serial IP injections separated by 2 weeks. Control mice from each strain were mock-sensitized with PBS. Challenges were performed by inhalation of a 0.25% Af aerosol. Serum IgE levels were measured after challenge from sensitized and unsensitized mice. Bronchoalveolar lavage fluid was analyzed after challenge by differential cell counts, cytokine levels, and histologic examination was performed.

Results:

After Af challenge, histologic analysis showed extensive goblet cell hyperplasia and lymphocytic infiltration in both strains. However, total serum IgE levels (ng/ml) were markedly elevated in the CFTR knockout mice, with and without specific sensitization. Sensitized CF mice (36,416±9257) showed a 5-fold greater IgE response to sensitization as compared with B6 sensitized (7,182±4,623) and FVB/NJ (7,796±2321). In agreement, Af specific IgE levels in CF mice were 5 fold higher than in FVB and 20 fold higher than in B6 mice.

IgG1 serum levels were also significantly higher in the CF mice (1419±93 ug/ml) when compared to the B6 mice (477±20 ug/ml). Furthermore, the BAL differential counts in CF mice showed a mixed response of both macrophages (45±2%) and eosinophils (52±6%) vs. an eosinophil-predominant response (74±11%) in the B6 mice. Consistent with the higher eosinophil infiltration, the B6 mice exhibited higher levels of IL-5 in the lungs (593+/−41 pg/ml) compared to the CFTR knockout mice (404+/−88 pg/ml).

Taken together, this data demonstrates that the CFTR mutation caused a shift from an IL-5-predominant to an IL-4-predominant cytokine profile resulting in a hyper-IgE response to Af antigen sensitization. This system models a very specific type of airway inflammation in CF and could provide insights into pathogenesis and treatment of the disease.

Example 19

This Example describes correction of the ABPA phenotype in CFTR deficient mice by rAAV-mediated gene therapy. In the above-described model of airway inflammation in a CFTR knockout mouse utilizing *Aspergillus fumigatus* (Af) antigen to mimic allergic bronchopulmonary aspergillosis (ABPA), an unusual IgE mediated hypersensitivity syndrome is seen. This condition is seen in up to 15% of CF patients and rarely outside of CF. This Example describes experiments indicating that replacement of CFTR via targeted gene delivery to the airway epithelium can correct aberrant epithelial cytokine signaling and thus ameliorate the ABPA phenotype in CFTR-deficient (CFTR 489x−/−, FABP-hCFTR+/+) mice.

Methods:

Six week-old CFTR knockout mice underwent intratracheal (IT) administration of recombinant adeno-associated virus serotype 5 (rAAV5-CBA-Δ-264CFTR) (N=7) or rAAV5GFP (N=4) at $2.58\times10^{12}$ viral genomes (VG)/mouse. All mice were then sensitized by two serial injections with 20 μg of crude Af antigen via an intraperitoneal (IP) route, separated by two weeks. Non-injected mice (N=3) were sensitized without prior virus exposure. Challenges were performed on all mice two weeks after final sensitization, using a 0.25% Af solution delivered by aerosol inhalation in a closed chamber on three consecutive days. Serum IgE levels (ng/ml) were then obtained, as well as bronchoalveolar lavage (BAL) fluid for differential cell counts, and histologic and cytokine analysis. Real-time quantitative polymerase chain reaction (PCR) and RT-PCR were utilized to confirm the presence of viral vector DNA and mRNA, respectively, in lung tissue.

Results:

FIG. 14 is shows down regulation of IgE responses following AAV5-CFTR gene therapy. Total serum IgE levels were measured by ELISA. More particularly, CFTR S489X −/−; FABP-hCFTR (+/+) mice were injected with rAAV virus expressing the delta264CFTR mini gene or GFP, driven by a CB promoter. Subsequently the mice were sensitized with *Aspergillus Fumigatus* (Af) crude extract via the intraperitoneal route and challenged with nebulized Af extract in an enclosed chamber. Serum was harvested 48 hrs after the last challenge for IgE analysis.

Referring to FIG. 14, it is seen that following challenge with Af, rAAV5-CFTR mice had significantly lower total serum IgE levels (17,251±3,214) as compared to rAAV5-GFP controls (26,892±7,430)(p=0.037), as well as non-injected, sensitized controls (24,816±7,299). The IgE levels in the latter mice are similar to those observed by us previously.

Figure 15B:
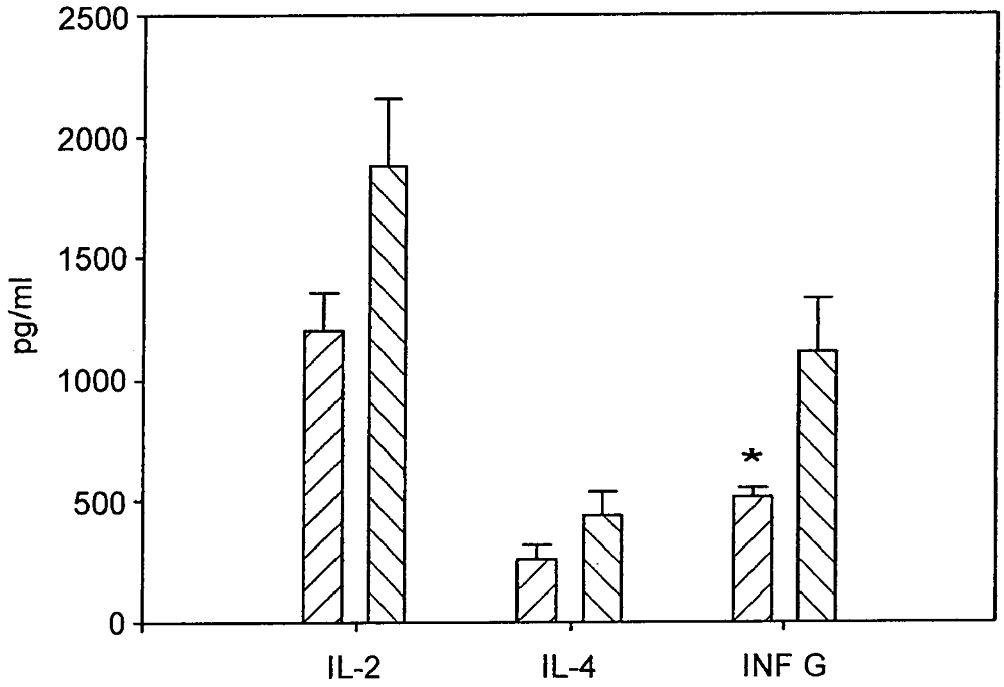

Splenocytes from rAAV5-CFTR and rAAV5-GFP treated mice were harvested 48 hrs after the last Af challenge. FIGS. 15A and 15B are two graphs depicting the effects of rAAV5-CFTR gene therapy on the secretion of cytokines by splenocytes. The splenocytes were plated in 96-well plates at a density of $10^5$ cells/well and activated with ConA. Supernatants were collected at 48 hrs and subsequently analyzed for levels of cytokines including IL-5, GM-CSF, TNF-α, IL-13, RANTES, IL-2, IL-4 and INF G, using a Luminex 100 system.

Conclusions: In a reproducible model of Af hyper-IgE-mediated sensitization in CF mice that mimics the ABPA phenotype, targeted gene replacement of CFTR via rAAV5-mediated vector delivery to airway epithelium in CFTR−/− mice results in a significant decrease in total serum IgE levels, as compared to GFP-injected and non-injected controls. These data support the concept that CFTR in the airway epithelium plays a critical role in cytokine regulation with systemic effects on the inflammatory response and help provide insight into the complex interactions between epithelial and systemic immuno-regulation in CF.

Example 20

This Example demonstrates gene transfer in airways of non-human primates using a pseudotyped AAV5 vector that shows improved transduction as well as protein expression relative to rAAV2 vectors, without evidence of clinical toxicity.

Materials and Methods:

Animals. Young adult *Rhesus macaques* (5 experimental, 1 untreated control) were from the Johns Hopkins University breeding colony and housed according to Animal Care and Use Committee guidelines. All macaques tested negative for simian immunodeficiency virus and Herpes virus simiae (Herpes B), and were evaluated by a veterinarian. The macaques ranged in weight from 10-14 lb. The experimental monkeys were 4 males (10-11 lbs) and the control monkeys were a female and male (~14 lb).

Figure 1B:
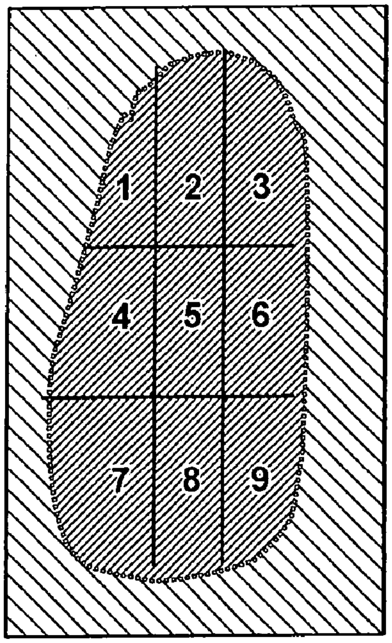

Study Design. This design was constructed to test if gene transfer by a rAAV5-pseudotyped vector could lead to transgene levels sufficient for gene expression. The experimental design is outlined in FIG. 1A. A total of 6 lungs received either $0.5\times10^{14}$ or $1\times10^{14}$ DRP/lung, 4 lungs were treated with a $1\times10^{14}$ DRP of an irrelevant transgene (internal control), and two lungs represent the untreated control animal. The treated animals received either $0.5\times10^{14}$ or $1\times10^{14}$ DRP aerosolized rAAV5-GFP per lung endobronchially delivered while spontaneously breathing as previously described [41]. The controls received $1\times10^{14}$ DRP of a pseudotyped rAAV5 vector with an internal control gene. Three weeks following vector administration, the animals were autopsied for detection of GFP DNA, RNA, and protein expression by confocal microscopy on frozen sections, as well as pathologic analysis. Sera were also taken prior to vector administration and just before necropsy. The indicated lung regions are defined as nine per lung (18 regions per animal) biplanar, non-anatomic sections for regional analysis, previously characterized by scintigraphy and described in this airway delivery model [41](FIG. 1B). Each region (108 total) was analyzed for GFP DNA transfer, mRNA transduction, and protein expression either by microscopy or Western blot analysis.

Vectors. The vectors were produced in the Vector Core at the University of Florida and packaged using pseudotyping techniques described above. A triple plasmid technique used the pXYZ5 plasmid, which is a construct of both the AAV2rep/AAV1 cap and AAV2rep/AAV5 cap helper plasmids constructed into an adenoviral plasmid backbone containing AD E4 genes. The recombinant AAV vector constructs, both the pseudotyped AAV5-GFP and pseudotyped AAV5-irrelevant gene insert, were assembled on the pTR-UF backbone. Vector preparations were from a single pooled stock with 99% purity and titers of $6.22\times10^{13}$ vector genomes/ml.

These two pseudotyped AAV5 vectors were administered at two doses differing by a ½log($0.5\times10^{14}$ or $1\times10^{14}$ DRP/lung) by endobronchial delivery with a PennCentury Microsprayer™ in rhesus macaques. FIG. 1A illustrates the dosing patterns per lung per monkey. Five macaques were dosed with up to $2\times10^{14}$ DRP of either pseudotyped AAV5-GFP and/or AAV5-irrelevant gene. Six lungs received either $0.5\times10^{14}$ or $1\times10^{14}$ DRP pseudotyped-AAV5-GFP and 4 lungs received $1\times10^{14}$ DRP of the irrelevant gene as an internal control. Untreated macaque lung tissue was also obtained for use as a negative untreated control.

Aerosol Delivery by Microsprayer™. rAAV5-pseudotyped (rep2 cap5) vectors were delivered directly to a mainstem bronchus using a MicroSprayer™ (PennCentury, Philadelphia, Pa.) inserted through a 3.5 mm flexible fiberoptic bronchoscope (Olympus, Melville, N.Y.). The macaques were sedated with ketamine and isofluorane, intubated with a 5.0 mm endotracheal tube (ETT), and given supplemental oxygen, but maintained spontaneous inhalation. Lidocaine (1%) was directly instilled onto the carina to minimize coughing as needed. Each vector dose was diluted in normal saline for a total volume of 3 ml (1.5 mL vector per lung). The Microsprayer™ was advanced approximately 3 mm beyond the tip of the bronchoscope in order to visualize aerosolization (10 sprays of approximately 150 μl each) of each vector into the right and left mainstem bronchi as previously described [41].

DNA and RNA Analysis. At necropsy (day 21), the lungs were harvested and infused with 60 cc of saline and divided into a nine-region grid as previously described (FIG. 1A). Approximately 90% of each lung region sample was flash frozen. The remaining 10% was frozen in optimum cutting temperature (OCT) compound (Sakura Finetek; Torrance, Calif.) and sectioned onto slides for histological analysis.

All lung regions were individually weighed, homogenized, and divided for RNA, DNA, and protein extraction. Quantitative PCR and RT-PCR were performed to test each lung region for GFP-specific transfer or transduction, respectively, using the LightCycler (Roche Molecular Biochemicals, Indianapolis, Ind.). The GFP-specific product was 205 bp, amplified from either 100 ng of genomic DNA or 360 ng cDNA, and using the same methodology, primers, and controls as previously described [49]. The RT reaction consisted of treating the RNA samples with DNase and reverse transcriptase before undergoing cDNA synthesis using the First-strand cDNA Synthesis Kit (Amersham Pharmacia Biotech, Piscataway, N.J.); RT− samples were not treated with reverse transcriptase. Then, 360 ng of that cDNA was used in quantitative PCR for GFP-specific detection. GFP-specific DNA or cDNA was measured using real-time PCR (LightCycler Roche Molecular Biochemicals, Indianapolis, Ind.) with standard controls of $10^5$, $10^4$, $10^3$, $10^2$, and $10^1$ plasmid copies per reaction. All samples were done in triplicate to ensure statistical significance.

Qualitative PCR and RT-PCR cycling for controls was conducted with the GeneAmp PCR System 2400 (Perkin Elmer, Wellesley, Mass.). RT-samples were used as negative controls and underwent PCR to detect both β-actin and GFP. RT+ samples were also controls for β-actin using sequence-specific primers, as previously described [41].

Protein Analysis. For Western blot analysis of respective lung samples for GFP protein expression (27 KD), 60 μg of lung protein was separated by 12% SDS-PAGE and transferred to PVDF membranes. The membranes were then blocked, washed, and incubated with a 1:4000 dilution of primary antibody to GFP, Ab 6556 (Abcam, Cambridge, UK), and a 1:10,000 dilution of secondary antibody (donkey anti-rabbit HRP-conjugate, Amersham Life Science, Arlington Heights, Ill.) in the same manner, as previously described [49].

Protein Analysis-Microscopy. Multiple transverse 5 μM sections were made through each of the nine regions perpendicular to visible bronchi or bronchioles when possible. We first examined unstained sections for GFP green fluorescence using a Zeiss Axiskop (Thornwood, N.Y.) upright epi-fluorescence microscope equipped with a GFP-specific filter set (excitation HQ470/40x, emitter HQ 515/30M).

Neutralizing Antibody Experiments. Serial dilutions of experimental and control sera were analyzed for the presence of anti-AAV5 neutralizing antibodies as previously described [49] using hepatoma cells (c12 #CRL-2710; ATCC, Manassas, Va.). The various dilutions of sera at necropsy were directly compared to the dilutions of sera obtained prior to AAV5 exposure. The various dilutions of sera were incubated with $10^5$ IU of rAAV-GFP for one hour prior to being added to c12 cells. Then 10 MOI/cell of wild-type adenovirus type 5

(Ad5) was added to the cells and media (Alpha minimum essential medium supplemented with 10% heat-inactivated fetal bovine serum and 1% penicillin-streptomycin). After approximately 24-hour incubation, the cells were visualized with a fluorescence microscope to detect the number of GFP-fluorescing cells. Neutralizing antibody titers were expressed as a reciprocal dilution of sera required for 10-fold neutralization. If documented as >10,000, then titer required to remove the inhibitory effect exceeded 1:10,000.

Anti-GFP antibody detection. Anti-GFP antibodies were measured in the pre and post-dosing sera of the five monkeys in an enzyme-linked immunosorbant assay (ELISA). Immunlon 4 HBX flat well absorbance protein binding plates (Dynex, Chantilly, Va.) were coated with 100 ng of purified recombinant GFP protein (Clontech, Palo Alto, Calif.) in 100 mM carbonate buffer, pH 9.6, and incubated overnight at 4° C. The antigen solution was then removed and replaced with 200 μl of blocking buffer (1% BSA, 5% Normal Goat Serum in PBS) and incubated for 2 hr at room temperature (rt). The plates were washed 2×3 min with wash buffer (0.05% Tween-20 in PBS) before sera (diluted 1:100 in blocking buffer) was added and then incubated at rt for 1 hr. The plates were washed 3×3 min and then the secondary antibody, peroxidase conjugated affinity purified goat anti-human IgG F(c) (Rockland, Gilbertsville, Pa.) diluted to 1:500 in blocking buffer was added and the plates were incubated for 1 hr at rt. The positive control was antigen laden microtiter wells stained with Living Colors® A.v. peptide antibody-HRP Conjugate (Clontech) diluted 1:500. The background control was the antigen laden microtiter wells stained only with the secondary antibody diluted 1:500. The plates were washed 5×3 min and incubated with 100 μl of substrate solution (o-Phenylenediamine dihydrochloride, Sigma, St. Louis, Mo.) before being read with the spectrophotometer (E max precision microplate reader (Molecular Devices, Sunnyvale, Calif.) at 450 nm.

Statistical analysis. Data are reported as means with median as the data are non-gaussian. S-Plus 6.2 (Insightful, Seattle, Wash.) was used to perform a Kruskal-Wallis rank sum test to assess the statistical significance of regional deposition fraction and vector transfer (copy number per region). Nonparametric tests were used because the data were not normally distributed. Box plots of statistical distributions were generated in Origin 7.5 (OriginLab, Northampton, Mass.). P values were deemed significant at ±0.05.

Results 1. rAAV5-mediated GFP DNA transfer. The schematic design was to deliver aerosolized pseudotyped AAV5-GFP vector at $0.5\times10^{14}$ DNase resistant particles (DRP)/lung in two lungs or $1\times10^{14}$ DRP/lung into four lungs (FIG. 16). The doses were chosen such that the low dose duplicated those achieved in prior rAAV2 studies in macaques and then was doubled to test whether a higher achievable dose resulted in higher gene transfer, transduction, or toxicity.

FIG. 17A-C depicts GFP doses per lung. FIG. 17A is a box plot demonstrating GFP dose per lung region versus DNA transfer (copy #/μg DNA). The GFP doses were either a low dose ($0.5\times10^{14}$ DRP/lung) for 18 samples, or high dose ($1\times10^{14}$ DRP/lung) for 28 samples. The black squares (■) represent the averaged mean and the line (-) represents the median. The x's (x) represent the 95% and 5% confidence intervals.

Referring to FIG. 17A, gene transfer of the GFP transgene was reproducibly detected by real time PCR. All GFP-treated lung regions (54/54) were positive for GFP-DNA transfer. The average copy number was $3.28\times10^5$ and $1.34\times10^6$ copies/μg of DNA (median $1.04\times10^5$ and $6.46\times10^4$ respectively) for those dosed with $0.5\times10^{14}$ or $1\times10^{14}$ DRP/lung of pseudotyped AAV5-GFP, respectively. The average was slightly higher in the $1\times10^{14}$ DRP/lung group, but was not statistically different. GFP was detected in the contralateral lungs as well ($5.16\times10^3$ copies/μg DNA, median=$4.60\times10^2$).

The untreated monkey demonstrated no evidence of GFP in any lung region as expected. The monkey that received the irrelevant control gene in both lungs did demonstrate evidence of GFP transfer in 9 out of 18 regions, albeit at two logs lower ($1.7\times10^3$ copies/μg DNA) than the GFP transfer achieved in treated lungs. The detection of the vector in the contralateral lungs of treated animals is most likely attributable to the dynamics of breathing, the potential effect of positive pressure of the airway on vector redistribution, and the aerosolized state of the vector. The presence of GFP in the control animal may reflect passive exposure to aerosolized GFP from shared housing, since the macaque treated with the irrelevant control was in a separate cage, but housed in the same environs of the experimental animals.

2. rAAV5-mediated RNA expression. To evaluate whether higher achievable vector delivery resulted in gene transduction, we determined the presence of mRNA expression by quantitative RT-PCR. GFP RNA expression was present and quantifiable in all treated regions (54/54 regions). FIG. 17B is a box plot showing GFP dose per lung region versus RNA transduction (vector copy #/μg cDNA). The GFP doses were either a low dose ($0.5\times10^{14}$ DRP/lung) for 18 samples or high dose ($1\times10^{14}$ DRP/lung) for 28 samples. The black squares (■) represent the averaged mean and the line (-) represents the median. The x's (x) represent the 95% and 5% confidence intervals.

Referring to FIG. 17B, RNA expression averaged $4.76\times10^4$ and $1.50\times10^6$ copies/μg RNA (median $4.29\times10^3$ and $1.10\times10^5$ respectively), for the two doses of vector, $0.5\times10^{14}$ and $1\times10^{14}$ DRP/lung. Contralateral lungs expressed $2.11\times10^3$ copies/μg RNA; median=$2.35\times10^3$. Notably, the control animal showed no evidence of GFP RNA expression, despite the presence of detectable DNA transfer (in 9/18 regions). This result suggests the possibility of detecting false positives as well as the potential redistribution of aerosolized vector due to pulmonary mechanics. The untreated lungs showed evidence of neither GFP transfer nor GFP expression.

FIG. 17C is a graph demonstrating the gene transfer (copy #/μg DNA) per lung region analyzed versus RNA transduction (vector copy #/μg DNA). The circles (°) represent low dose GFP ($0.5\times10^{14}$ DRP/lung) and the triangles (Δ) represent high dose GFP $1\times10^{14}$ DRP/lung. FIG. 17C shows that the dose effect of increasing DNA transfer associated linearly with the level of mRNA expression. Increasing mRNA expression is demonstrated at higher levels of GFP transfer. Additional results from these studies are illustrated in FIG. 21 and further described in the legend accompanying the drawing.

3. rAAV5-mediated protein expression. GFP protein expression via fluorescence was detected by confocal microscopy in the epithelial cells of the airways of all experimental animals. FIG. 18A-D demonstrates GFP protein expression following gene transfer in experimental and control animals. Fluorescent GFP expression was analyzed by microscopy in bronchial epithelium three weeks after dosing with the vector. Lungs were sectioned into nine regions/lung and dissected at the level of segmental branching and processed for frozen sectioning before being analyzed for GFP fluorescent expression by microscopy.

FIG. 18A demonstrates GFP expression in the cytoplasm of ciliated airway epithelial cells in a pseudotyped AAV5-GFP treated macaque, whereas there is an absence of GFP-specific expression in pulmonary sections from a control macaque (FIG. 18C). FIGS. 18B and 18D are bright field images of the sections corresponding to FIGS. 18A and 18C, respectively. Magnification is 1000×. More specifically, FIG. 18A shoes GFP fluorescence in the cytoplasm of ciliated epithelial cells along bronchial airways and in submucosal glands, observed in all experimental animals. The arrows delineate the apical border of the airway epithelial cells, shown in the bright field picture, and illustrate the corresponding absence of intracellular green fluorescence in the control (FIG. 18C, 18D).

Western blot analysis further verified the presence of rAAV5-mediated GFP protein expression in representative regions from vector-treated animals at both doses. FIG. 18E is a Western blot showing rAAV5-mediated GFP expression in the lung.

In summary, the results of these experiments demonstrate that the gene transfer resulted in rAAV5-mediated GFP expression, as confirmed both by confocal microscopy in situ as well as by Western blot analysis.

4. Evidence of Minimal rAAV5-Mediated Inflammation

All macaques tolerated bronchoscopies and anesthetics without adverse sequelae. All macaques remained healthy with vigorous appetites, normal behavior, and no signs of respiratory distress or acute upper respiratory infections. Their clinical course was evaluated twice a day minimally and after 72 hours was evaluated on a daily basis.

Upon comprehensive review of frozen tissue sections from each lung, there was no evidence of acute or chronic inflammation along the airways, interstitial, or alveolar spaces present in experimental animals, as compared to the control animal as examined by a pathologist, blinded to the experiment. A review of hematoxylin-and-eosin stained lung sections from each lung revealed no identifiable difference in the histology between the experimental and control animals. Specifically, there was no evidence of destructive acute changes such as eosinophilia, enlarged bronchial lymphoid aggregates, or inflammatory infiltrates, or chronic changes such as chronic bronchiectasis obliterans or bronchiectasis in the lungs after administration of the rAAV5 vectors. These findings were compared with baseline findings established in non-treated controls, and no evidence of pathologic sequelae was detected (FIG. 19).

5. Analysis of anti-AAV5 neutralizing activity in sera. To determine whether dosing with rAAV5 elicited a significant humoral immune response to the AAV5 serotype, sera from treated animals were analyzed for anti-AAV5 neutralizing antibodies prior to and after treatment. Anti-AAV5 neutralizing activity is a functional measure of the capacity of antibodies in the sera to block re-infection following exposure to rAAV5. The higher the titer or the reciprocal of the dilution required to inhibit rAAV5-mediated in vitro expression, the greater the potency of the elicited anti-serotypic antibody response. Serum from all macaques was obtained prior to vector exposure and three weeks following vector exposure.

FIG. 20A-F depicts results of analysis of anti-AAV neutralizing antibody activity. FIGS. 20A-B show fluorescent micrographs of hepatoma c 12 cells infected with a pseudotyped rAAV5-GFP viral vector and preincubated with monkey sera either prior to dosing (20A) or three weeks post dosing (20B). Similar fluorescent micrographs are shown for sera from an animal treated with irrelevant gene prior to dosing (20D) or three weeks post dosing (20E). FIG. 20C represents the positive in vitro control of AAV5-GFP c12 cells co-infected with Ad5 without sera. FIG. 20F depicts an ELISA demonstrating no anti-GFP reactivity in the sera. Anti-AAV5 antibodies were detected at low levels (1:5000) after one aerosolized dose and did not grossly vary between animals despite the animals being exposed to doses of $1\times10^{14}$, $1.5\times10^{14}$, or $2\times10^{14}$ DRP per animal. Furthermore, an ELISA was performed to detect whether a humoral response specific to the GFP, a foreign transgene, was induced.

The results demonstrated that anti-GFP antibodies were not detectable in the sera either before or after the administration of rAAV5-GFP. The absence of anti-GFP antibodies may reflect the low expression of GFP upon the single initial exposure to GFP.

6. Comparison with studies using AAV2 vectors. Prior scintigraphy studies in AAV2-treated macaques did result in dose-dependent gene transfer which confirmed that greater deposition translates into enhanced gene transfer [41]. Likewise, AAV2-mediated expression was enhanced when the dose exceeded a threshold level ($3\times10^9$ i.u. per lung region), suggesting that limited expression can be explained by the dose.

In these studies with a pseudotyped AAV5, both doses of vector, i.e., $0.5\times10^{14}$ and $1\times10^{14}$ DRP/lung, resulted in gene transfer. In comparison to historical comparisons with the AAV2 studies in this same animal model, the averaged gene transfer was $1.89\times10^4$, as compared with $3.27\times10^5$ copies/μg of DNA in the current studies for similarly dosed macaques. Significantly, this difference is approximately a 20-fold increase in gene transfer, commensurate with the reported 30-fold increase seen in mice due to the efficiency of AAV5 infectivity. This log difference in gene transfer resulted in both vector-derived gene expression in all regions and RNA expression at a quantifiable level, which had not been accomplished in prior studies. More importantly, in those studies, RNA expression was detected only qualitatively by nested RT-PCR in some of the regions and was not sufficient for quantitative analysis.

The vector-derived expression in this study was further confirmed by Western analysis with a purified polyclonal rabbit anti-GFP antibody and upon direct microscopy for detection of green GFP fluorescence. The detection of gene transfer without corresponding vector-mediated transduction in the lungs treated with an irrelevant control gene suggests detection of false positives or contamination from residual aerosol during shared facilities.

Similar to prior studies in nonhuman primates, there was no evidence of toxicity despite the higher titer of vector, gene transfer, transduction, and expression. The lack of toxicity was assessed both by clinical observational parameters and by histology, read by a pathologist blinded to the study. The anti-neutralizing antibody experiments did not demonstrate the presence of antibodies in the serum to the higher titers of AAV5. Likewise, the ELISA confirmed the absence of an antibody response to GFP expression, as would be expected upon a single antigenic exposure. Prior studies in rodents have shown escalating neutralizing antibodies such as the readministration of AAV2 inhibiting gene transfer upon reexposure in mice and rabbits[40,50]. In fact, Halbert et al. demonstrated the efficacy of transient immunosuppression to abrogate the neutralizing antibodies blocking gene transfer in mice.

In contrast to rodent models, anti-neutralizing antibodies that block gene transfer have not been detected in primates in the AAV2 studies as well as the current AAV5 studies. In clinical trials, redosing with AAV2-CFTR has resulted in increased anti-AAV2 titers but is not consistently shown to block gene transfer; thus, the primate model more closely mirrors the human trials. Furthermore, the lack of association between preexisting serum anti-AAV2 titers and gene transfer supports the idea that the immune system may be partially compartmentalized in humans and primates, and that hematogenous immunity may not be reflected in mucosal immunities.

In summary, these studies have demonstrated enhanced gene transfer using a pseudotyped AAV5 vector with improved transduction as well as protein expression without evidence of toxicity. The discovery of the relative inefficiency of AAV2 at transducing airway epithelia has led to the investigation of other serotypes and the characterization of even rescuable serotypes from primates, creating a rich source of potential vectors. The divergence of AAV5 is particularly promising since it has a distinct receptor very applicable to using alternative serotypes for readministration of vector and thus can expand the utility of AAV vectors for gene transfer.

Example 21

This Example describes a pseudotyped AAV2/5 vector comprising a biologically active fragment of a CFTR protein operably linked to an efficient promoter in a construct optimized to fit into an AAV viral vector.

As discussed above, the large size of the CFTR cDNA insert is a limitation that precludes the inclusion of certain highly efficient promoters, due to the limited packaging capacity of AAV viral particles. Accordingly, there is a need to generate optimized AAV gene therapy vectors containing nucleic acid sequences encoding functionally active truncated CFTR fragments that are expressed at a high level. An important feature of a truncated CFTR fragment suitable for CFTR rescue by gene therapy is that the protein is expressed at the plasma membrane of the recipient cell.

A particularly preferred AAV vector that directs robust expression of CFTR at the plasma membrane is designated rAAV5-CB-Δ27-264CFTR and expresses a truncated human CFTR protein ("Δ27-264CFTR" or "del 27-264CFTR") that includes the first 26 amino acids of CFTR and is missing the portion between the $27^{th}$ and $264^{th}$ amino acid of the protein. The nucleic acid sequence encoding the truncated CFTR protein is operably linked to a powerful exogenous promoter, i.e., an enhanced chicken beta actin (CBA) promoter, i.e., a cytomegalovirus enhancer/chicken beta-actin promoter.

An exemplary AAV plasmid vector comprising a del 27-264CFTR construct driven by a CBA promoter that is suitable for packaging into rAAV particles is the plasmid pLGT2-CB-del 27-264 CFTR, shown in FIG. 22. The DNA sequence of pLGT2-CB-del 27-264 CFTR vector (SEQ ID NO: 8) is shown in FIG. 23, and the corresponding amino acid sequence (SEQ ID NO:9) is shown in FIG. 24.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant adenoviral associated virus (AAV) gene therapy particle comprising a nucleic acid encoding a truncated cystic fibrosis transmembrane conductance regulator (CFTR) protein consisting of the amino acid sequence of SEQ ID NO 9, operatively linked to a promoter, and a first and a second AAV inverted terminal repeat (ITR) sequence flanking the sequence encoding the truncated CFTR protein.

2. The rAAV gene therapy particle of claim 1, wherein the promoter is a chicken beta actin (CB) promoter or a cytomegalovirus enhancer/chicken beta-actin promoter.

3. The rAAV gene therapy particle of claim 1, wherein the ITR nucleotide sequences are derived from AAV serotype 2 (AAV-2).

4. A pharmaceutical composition comprising the AAV gene therapy particle of claim 1 in a biocompatible pharmaceutical carrier.

* * * * *

SEQUENCE LISTING

```
<160> NUMBER OF SEQ ID NOS: 9

<210> SEQ ID NO 1
<211> LENGTH: 7934
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1

ttggccactc cctctctgcg cgctcgctcg ctcactgagg ccgggcgacc aaaggtcgcc      60

cgacgcccgg gctttgcccg ggcggcctca gtgagcgagc gagcgcgcag agagggagtg     120

gccaactcca tcactagggg ttcctagatc tgaattcggt accctagtta ttaatagtaa     180

tcaattacgg ggtcattagt tcatagccca tatatggagt tccgcgttac ataacttacg     240

gtaaatggcc cgcctggctg accgcccaac gacccccgcc cattgacgtc aataatgacg     300

tatgttccca tagtaacgcc aatagggact ttccattgac gtcaatgggt ggactattta     360

cggtaaactg cccacttggc agtacatcaa gtgtatcata tgccaagtac gccccctatt     420

gacgtcaatg acggtaaatg gcccgcctgg cattatgccc agtacatgac cttatgggac     480

tttcctactt ggcagtacat ctacgtatta gtcatcgcta ttaccatggt cgaggtgagc     540

cccacgttct gcttcactct ccccatctcc cccccctccc caccccaat tttgtattta      600

tttatttttt aattattttg tgcagcgatg ggggcggggg gggggggggg gcgcgcgcca     660

ggcggggcgg ggcggggcga ggggcggggc ggggcgaggc ggagaggtgc ggcggcagcc     720

aatcagagcg gcgcgctccg aaagtttcct tttatggcga ggcggcggcg gcggcggccc     780
```

-continued

```
tataaaaagc gaagcgcgcg gcgggcggga gtcgctgcga cgctgccttc gccccgtgcc    840
ccgctccgcc gccgcctcgc gccgcccgcc ccggctctga ctgaccgcgt tactcccaca    900
ggtgagcggg cgggacggcc cttctcctcc gggctgtaat tagcgcttgg tttaatgacg    960
gcttgtttct tttctgtggc tgcgtgaaag ccttgagggg ctccgggagc tagagcctct   1020
gctaaccatg ttcatgcctt cttctttttc ctacagctcc tgggcaacgt gctggttatt   1080
gtgctgtctc atcattttgg caaagaattc ctcgaagatc cgaaggggtt caagcttaaa   1140
aactagtgcc gccaccatga tcgagaacat ccaatctgtt aaggcatact gctgggaaga   1200
agcaatggaa aaaatgattg aaaacttaag acaaacagaa ctgaaactga ctcggaaggc   1260
agcctatgtg agatacttca atagctcagc cttcttcttc tcagggttct ttgtggtgtt   1320
tttatctgtg cttccctatg cactaatcaa aggaatcatc ctccggaaaa tattcaccac   1380
catctcattc tgcattgttc tgcgcatggc ggtcactcgg caatttccct gggctgtaca   1440
aacatggtat gactctcttg gagcaataaa caaaatacag gatttcttac aaaagcaaga   1500
atataagaca ttggaatata acttaacgac tacagaagta gtgatggaga atgtaacagc   1560
cttctgggag gagggatttg gggaattatt tgagaaagca aaacaaaaca ataacaatag   1620
aaaaacttct aatggtgatg acagcctctt cttcagtaat ttctcacttc ttggtactcc   1680
tgtcctgaaa gatattaatt tcaagataga aagaggacag ttgttggcgg ttgctggatc   1740
cactggagca ggcaagactt cacttctaat gatgattatg ggagaactgg agccttcaga   1800
gggtaaaatt aagcacagtg gaagaatttc attctgttct cagttttcct ggattatgcc   1860
tggcaccatt aaagaaaata tcatctttgg tgtttcctat gatgaatata gatacagaag   1920
cgtcatcaaa gcatgccaac tagaagagga catctccaag tttgcagaga aagacaatat   1980
agttcttgga gaaggtggaa tcacactgag tggaggtcaa cgagcaagaa tttctttagc   2040
aagagcagta tacaaagatg ctgatttgta tttattagac tctccttttg gatacctaga   2100
tgttttaaca gaaaaagaaa tatttgaaag ctgtgtctgt aaactgatgg ctaacaaaac   2160
taggattttg gtcacttcta aaatggaaca tttaaagaaa gctgacaaaa tattaatttt   2220
gcatgaaggt agcagctatt tttatgggac attttcagaa ctccaaaatc tacagccaga   2280
ctttagctca aaactcatgg gatgtgattc tttcgaccaa tttagtgcag aaagaagaaa   2340
ttcaatccta actgagacct tacaccgttt ctcattagaa ggagatgctc ctgtctcctg   2400
gacagaaaca aaaaaacaat cttttaaaca gactggagag tttggggaaa aaaggaagaa   2460
ttctattctc aatccaatca actctatacg aaaattttcc attgtgcaaa agactccctt   2520
acaaatgaat ggcatcgaag aggattctga tgagccttta gagagaaggc tgtccttagt   2580
accagattct gagcagggag aggcgatact gcctcgcatc agcgtgatca gcactggccc   2640
cacgcttcag gcacgaagga ggcagtctgt cctgaacctg atgacacact cagttaacca   2700
aggtcagaac attcaccgaa agacaacagc atccacagga aaagtgtcac tggcccctca   2760
ggcaaacttg actgaactgg atatatattc aagaaggtta tctcaagaaa ctggcttgga   2820
aataagtgaa gaaattaacg aagaagactt aaaggagtgc ctttttgatg atatggagag   2880
cataccagca gtgactacat ggaacacata ccttcgatat attactgtcc acaagagctt   2940
aatttttgtg ctaatttggt gcttagtaat tttttctggca gaggtggctg cttctttggt   3000
tgtgctgtgg ctccttggaa acactcctct tcaagacaaa gggaatagta ctcatagtag   3060
aaataacagc tatgcagtga ttatcaccag caccagttcg tattatgtgt tttacattta   3120
cgtgggagta gccgacactt tgcttgctat gggattcttc agaggtctac cactggtgca   3180
```

-continued

```
tactctaatc acagtgtcga aaattttaca ccacaaaatg ttacattctg ttcttcaagc   3240
acctatgtca accctcaaca cgttgaaagc aggtgggatt cttaatagat tctccaaaga   3300
tatagcaatt ttggatgacc ttctgcctct taccatattt gacttcatcc agttgttatt   3360
aattgtgatt ggagctatag cagttgtcgc agttttacaa ccctacatct ttgttgcaac   3420
agtgccagtg atagtggctt ttattatgtt gagagcatat ttcctccaaa cctcacagca   3480
actcaaacaa ctggaatctg aaggcaggag tccaattttc actcatcttg ttacaagctt   3540
aaaaggacta tggacacttc gtgccttcgg acggcagcct tactttgaaa ctctgttcca   3600
caaagctctg aatttacata ctgccaactg gttcttgtac ctgtcaacac tgcgctggtt   3660
ccaaatgaga atagaaatga tttttgtcat cttcttcatt gctgttacct tcatttccat   3720
tttaacaaca ggagaaggag aaggaagagt tggtattatc ctgactttag ccatgaatat   3780
catgagtaca ttgcagtggg ctgtaaactc cagcatagat gtggatagct tgatgcgatc   3840
tgtgagccga gtctttaagt tcattgacat gccaacagaa ggtaaaccta ccaagtcaac   3900
caaaccatac aagaatggcc aactctcgaa agttatgatt attgagaatt cacacgtgaa   3960
gaaagatgac atctggccct caggggggcca aatgactgtc aaagatctca cagcaaaata   4020
cacagaaggt ggaaatgcca tattagagaa catttccttc tcaataagtc ctggccagag   4080
ggtgggcctc ttgggaagaa ctggatcagg gaagagtact ttgttatcag ctttttttgag   4140
actactgaac actgaaggag aaatccagat cgatggtgtg tcttgggatt caataacttt   4200
gcaacagtgg aggaaagcct ttggagtgat accacagaaa gtatttattt tttctggaac   4260
atttagaaaa aacttggatc cctatgaaca gtggagtgat caagaaatat ggaaagttgc   4320
agatgaggtt gggctcagat ctgtgataga acagtttcct gggaagcttg actttgtcct   4380
tgtggatggg ggctgtgtcc taagccatgg ccacaagcag ttgatgtgct tggctagatc   4440
tgttctcagt aaggcgaaga tcttgctgct tgatgaaccc agtgctcatt tggatccagt   4500
aacataccaa ataattagaa gaactctaaa acaagcattt gctgattgca cagtaattct   4560
ctgtgaacac aggatagaag caatgctgga atgccaacaa tttttggtca tagaagagaa   4620
caaagtgcgg cagtacgatt ccatccagaa actgctgaac gagaggagcc tcttccggca   4680
agccatcagc ccctccgaca gggtgaagct ctttccccac cggaactcaa gcaagtgcaa   4740
gtctaagccc cagattgctg ctctgaaaga ggagacagaa gaagaggtgc aagatacaag   4800
gctttagaga gcagcataaa tgttgacatg ggacatttgc tcatggaatt ggcaggccta   4860
ataaagagct cagatgcatc gatcagagtg tgttggtttt ttgtgtgtac tgaggaaccc   4920
ctagtgatgg agttggccac tccctctctg cgcgctcgct cgctcactga ggccgcccgg   4980
gcaaagcccg ggcgtcgggc gacctttggt cgcccggcct cagtgagcga gcgagcgcgc   5040
agagagggag tggccaaccc cccccccccc cccccctgcag cccagctgca ttaatgaatc   5100
ggccaacgcg cggggagagg cggtttgcgt attgggcgct cttccgcttc ctcgctcact   5160
gactcgctgc gctcggtcgt tcggctgcgg cgagcggtat cagctcactc aaaggcggta   5220
atacggttat ccacagaatc aggggataac gcaggaaaga acatgtgagc aaaaggccag   5280
caaaaggcca ggaaccgtaa aaaggccgcg ttgctggcgt ttttccatag gctccgcccc   5340
cctgacgagc atcacaaaaa tcgacgctca agtcagaggt ggcgaaaccc gacaggacta   5400
taaagatacc aggcgtttcc ccctggaagc tccctcgtgc gctctcctgt tccgaccctg   5460
ccgcttaccg gatacctgtc cgcctttctc ccttcgggaa gcgtggcgct ttctcaatgc   5520
tcacgctgta ggtatctcag ttcggtgtag gtcgttcgct ccaagctggg ctgtgtgcac   5580
```

```
gaacccccccg ttcagcccga ccgctgcgcc ttatccggta actatcgtct tgagtccaac   5640
ccggtaagac acgacttatc gccactggca gcagccactg gtaacaggat tagcagagcg   5700
aggtatgtag gcggtgctac agagttcttg aagtggtggc ctaactacgg ctacactaga   5760
aggacagtat ttggtatctg cgctctgctg aagccagtta ccttcggaaa aagagttggt   5820
agctcttgat ccggcaaaca aaccaccgct ggtagcggtg gtttttttgt ttgcaagcag   5880
cagattacgc gcagaaaaaa aggatctcaa gaagatcctt tgatcttttc tacggggtct   5940
gacgctcagt ggaacgaaaa ctcacgttaa gggattttgg tcatgagatt atcaaaaagg   6000
atcttcacct agatcctttt aaattaaaaa tgaagtttta aatcaatcta aagtatatat   6060
gagtaaactt ggtctgacag ttaccaatgc ttaatcagtg aggcacctat ctcagcgatc   6120
tgtctatttc gttcatccat agttgcctga ctccccgtcg tgtagataac tacgatacgg   6180
gagggcttac catctggccc cagtgctgca atgataccgc gagacccacg ctcaccggct   6240
ccagatttat cagcaataaa ccagccagcc ggaagggccg agcgcagaag tggtcctgca   6300
actttatccg cctccatcca gtctattaat tgttgccggg aagctagagt aagtagttcg   6360
ccagttaata gtttgcgcaa cgttgttgcc attgctacag gcatcgtggt gtcacgctcg   6420
tcgtttggta tggcttcatt cagctccggt tcccaacgat caaggcgagt tacatgatcc   6480
cccatgttgt gcaaaaaagc ggttagctcc ttcggtcctc cgatcgttgt cagaagtaag   6540
ttggccgcag tgttatcact catggttatg gcagcactgc ataattctct tactgtcatg   6600
ccatccgtaa gatgcttttc tgtgactggt gagtactcaa ccaagtcatt ctgagaatag   6660
tgtatgcggc gaccgagttg ctcttgcccg gcgtcaatac gggataatac cgcgccacat   6720
agcagaactt taaaagtgct catcattgga aaacgttctt cggggcgaaa actctcaagg   6780
atcttaccgc tgttgagatc cagttcgatg taacccactc gtgcacccaa ctgatcttca   6840
gcatctttta ctttcaccag cgtttctggg tgagcaaaaa caggaaggca aaatgccgca   6900
aaaaagggaa taagggcgac acggaaatgt tgaatactca tactcttcct ttttcaatat   6960
tattgaagca tttatcaggg ttattgtctc atgagcggat acatatttga atgtatttag   7020
aaaaataaac aaataggggt tccgcgcaca tttccccgaa aagtgccacc tgacgtctaa   7080
gaaaccatta ttatcatgac attaacctat aaaaataggc gtatcacgag gccctttcgt   7140
ctcgcgcgtt tcggtgatga cggtgaaaac ctctgacaca tgcagctccc ggagacggtc   7200
acagcttgtc tgtaagcgga tgccgggagc agacaagccc gtcagggcgc gtcagcgggt   7260
gttggcgggt gtcggggctg gcttaactat gcggcatcag agcagattgt actgagagtg   7320
caccatatgc ggtgtgaaat accgcacaga tgcgtaagga gaaaataccg catcaggaaa   7380
ttgtaaacgt taatattttg ttaaaattcg cgttaaattt ttgttaaatc agctcatttt   7440
ttaaccaata ggccgaaatc ggcaaaatcc cttataaatc aaaagaatag accgagatag   7500
ggttgagtgt tgttccagtt tggaacaaga gtccactatt aaagaacgtg gactccaacg   7560
tcaaagggcg aaaaaccgtc tatcagggcg atggcccact acgtgaacca tcaccctaat   7620
caagtttttt ggggtcgagg tgccgtaaag cactaaatcg gaaccctaaa gggagccccc   7680
gatttagagc ttgacgggga aagccggcga acgtggcgag aaaggaaggg aagaaagcga   7740
aaggagcggg cgctagggcg ctggcaagtg tagcggtcac gctgcgcgta accaccacac   7800
ccgccgcgct taatgcgccg ctacagggcg cgtcgcgcca ttcgccattc aggctacgca   7860
actgttggga agggcgatcg gtgcgggcct cttcgctatt acgccagctg gctgcagggg   7920
gggggggggg gggg                                                     7934
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
atgtgcagga gagaaccatc t 21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gccattcttt tacttgtcgg c 21

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
taaagactct atgccaacac agt 23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
cacgatggag gggccggact catc 24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tctcttatgg cgtgcagtgc t 21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
tggagtgttc tgttgataat g 21

<210> SEQ ID NO 8
<211> LENGTH: 3730
<212> TYPE: DNA
<213> ORGANISM: Artificial Sequence
<220> FEATURE:
<223> OTHER INFORMATION: Description of Artificial Sequence: Synthetic construct

<400> SEQUENCE: 8
atgcagaggt cgcctctgga aaaggccagc gttgtctcca aactttttt cagctggacc 60 agaccaattt tgaggaaaat gattgaaaat atccaatctg ttaaggcata ctgctgggaa 120
gaagcaatgg aaaaaatgat tgaaaactta agacaaacag aactgaaact gactcggaag 180
gcagcctatg tgagatactt caatagctca gccttcttct tctcagggtt ctttgtggtg 240
tttttatctg tgcttcccta tgcactaatc aaaggaatca tcctccggaa aatattcacc 300
accatctcat tctgcattgt tctgcgcatg gcggtcactc ggcaatttcc ctgggctgta 360
caaacatggt atgactctct tggagcaata aacaaaatac aggatttctt acaaaagcaa 420
gaatataaga cattggaata taacttaacg actacagaag tagtgatgga gaatgtaaca 480
gccttctggg aggagggatt tggggaatta tttgagaaag caaaacaaaa caataacaat 540
agaaaaactt ctaatggtga tgacagcctc ttcttcagta atttctcact tcttggtact 600
cctgtcctga aagatattaa tttcaagata gaaagaggac agttgttggc ggttgctgga 660
tccactggag caggcaagac ttcacttcta atgatgatta tgggagaact ggagccttca 720
gagggtaaaa ttaagcacag tggaagaatt tcattctgtt ctcagttttc ctggattatg 780
cctggcacca ttaaagaaaa tatcatcttt ggtgtttcct atgatgaata tagatacaga 840
agcgtcatca aagcatgcca actagaagag gacatctcca agtttgcaga gaaagacaat 900
atagttcttg gagaaggtgg aatcacactg agtggaggtc aacgagcaag aatttcttta 960
gcaagagcag tatacaaaga tgctgatttg tatttattag actctccttt tggataccta 1020
gatgttttaa cagaaaaaga aatatttgaa agctgtgtct gtaaactgat ggctaacaaa 1080
actaggattt tggtcacttc taaaatggaa catttaaaga aagctgacaa aatattaatt 1140
ttgaatgaag gtagcagcta tttttatggg acattttcag aactccaaaa tctacagcca 1200
gactttagct caaaactcat gggatgtgat tctttcgacc aatttagtgc agaaagaaga 1260
aattcaatcc taactgagac cttacaccgt ttctcattag aaggagatgc tcctgtctcc 1320
tggacagaaa caaaaaaaca atcttttaaa cagactggag agtttgggga aaaaaggaag 1380
aattctattc tcaatccaat caactctata cgaaaatttt ccattgtgca aaagactccc 1440
ttacaaatga atggcatcga agaggattct gatgagcctt tagagagaag gctgtcctta 1500
gtaccagatt ctgagcaggg agaggcgata ctgcctcgca tcagcgtgat cagcactggc 1560
cccacgcttc aggcacgaag gaggcagtct gtcctgaacc tgatgacaca ctcagttaac 1620
caaggtcaga acattcaccg aaagacaaca gcatccacac gaaaagtgtc actggcccct 1680
caggcaaact tgactgaact ggatatatat tcaagaaggt tatctcaaga aactggcttg 1740
gaaataagtg aagaaattaa cgaagaagac ttaaaggagt gcctttttga tgatatggag 1800
agcataccag cagtgactac atggaacaca taccttcgat atattactgt ccacaagagc 1860 ttaattttg tgctaatttg gtgcttagta atttttctgg cagaggtggc tgcttctttg 1920
gttgtgctgt ggctccttgg aaacactcct cttcaagaca aagggaatag tactcatagt 1980
agaaataaca gctatgcagt gattatcacc agcaccagtt cgtattatgt gttttacatt 2040
tacgtgggag tagccgacac tttgcttgct atgggattct tcagaggtct accactggtg 2100

```
catactctaa tcacagtgtc gaaaatttta caccacaaaa tgttacattc tgttcttcaa   2160

gcacctatgt caaccctcaa cacgttgaaa gcaggtggga ttcttaatag attctccaaa   2220

gatatagcaa ttttggatga ccttctgcct cttaccatat ttgacttcat ccagttgtta   2280

ttaattgtga ttggagctat agcagttgtc gcagttttac aaccctacat ctttgttgca   2340

acagtgccag tgatagtggc ttttattatg ttgagagcat atttcctcca aacctcacag   2400

caactcaaac aactggaatc tgaaggcagg agtccaattt tcactcatct tgttacaagc   2460

ttaaaaggac tatggacact tcgtgccttc ggacggcagc cttactttga aactctgttc   2520

cacaaagctc tgaatttaca tactgccaac tggttcttgt acctgtcaac actgcgctgg   2580

ttccaaatga gaatagaaat gatttttgtc atcttcttca ttgctgttac cttcatttcc   2640

attttaacaa caggagaagg agaaggaaga gttggtatta tcctgacttt agccatgaat   2700

atcatgagta cattgcagtg ggctgtaaac tccagcatag atgtggatag cttgatgcga   2760

tctgtgagcc gagtctttaa gttcattgac atgccaacag aaggtaaacc taccaagtca   2820

accaaaccat acaagaatgg ccaactctcg aaagttatga ttattgagaa ttcacacgtg   2880

aagaaagatg acatctggcc ctcagggggc caaatgactg tcaaagatct cacagcaaaa   2940

tacacagaag gtggaaatgc catattagag aacatttcct tctcaataag tcctggccag   3000

agggtgggcc tcttgggaag aactggatca gggaagagta ctttgttatc agctttttg   3060

agactactga acactgaagg agaaatccag atcgatggtg tgtcttggga ttcaataact   3120

ttgcaacagt ggaggaaagc ctttggagtg ataccacaga aagtatttat tttttctgga   3180

acatttagaa aaaacttgga tccctatgaa cagtggagtg atcaagaaat atggaaagtt   3240

gcagatgagg ttgggctcag atctgtgata gaacagtttc ctgggaagct tgactttgtc   3300

cttgtggatg gggctgtgt cctaagccat ggccacaagc agttgatgtg cttggctaga   3360

tctgttctca gtaaggcgaa gatcttgctg cttgatgaac ccagtgctca tttggatcca   3420

gtaacatacc aaataattag aagaactcta aaacaagcat ttgctgattg cacagtaatt   3480

ctctgtgaac acaggataga agcaatgctg gaatgccaac aatttttggt catagaagag   3540

aacaaagtgc ggcagtacga ttccatccag aaactgctga acgagaggag cctcttccgg   3600

caagccatca gcccctccga cagggtgaag ctctttcccc accggaactc aagcaagtgc   3660

aagtctaagc cccagattgc tgctctgaaa gaggagacag aagaagaggt gcaagataca   3720

aggctttaga                                                          3730
```

```
<210> SEQ ID NO 9
<211> LENGTH: 1242
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 9

Met Gln Arg Ser Pro Leu Glu Lys Ala Ser Val Val Ser Lys Leu Phe
  1               5                  10                  15

Phe Ser Trp Thr Arg Pro Ile Leu Arg Lys Met Ile Glu Asn Ile Gln
             20                  25                  30

Ser Val Lys Ala Tyr Cys Trp Glu Glu Ala Met Glu Lys Met Ile Glu
         35                  40                  45

Asn Leu Arg Gln Thr Glu Leu Lys Leu Thr Arg Lys Ala Ala Tyr Val
     50                  55                  60

Arg Tyr Phe Asn Ser Ser Ala Phe Phe Phe Ser Gly Phe Phe Val Val
```

-continued

```
65                  70                  75                  80

Phe Leu Ser Val Leu Pro Tyr Ala Leu Ile Lys Gly Ile Ile Leu Arg
                85                  90                  95

Lys Ile Phe Thr Thr Ile Ser Phe Cys Ile Val Leu Arg Met Ala Val
            100                 105                 110

Thr Arg Gln Phe Pro Trp Ala Val Gln Thr Trp Tyr Asp Ser Leu Gly
        115                 120                 125

Ala Ile Asn Lys Ile Gln Asp Phe Leu Gln Lys Gln Glu Tyr Lys Thr
    130                 135                 140

Leu Glu Tyr Asn Leu Thr Thr Thr Glu Val Val Met Glu Asn Val Thr
145                 150                 155                 160

Ala Phe Trp Glu Glu Gly Phe Gly Glu Leu Phe Glu Lys Ala Lys Gln
                165                 170                 175

Asn Asn Asn Asn Arg Lys Thr Ser Asn Gly Asp Asp Ser Leu Phe Phe
            180                 185                 190

Ser Asn Phe Ser Leu Leu Gly Thr Pro Val Leu Lys Asp Ile Asn Phe
        195                 200                 205

Lys Ile Glu Arg Gly Gln Leu Leu Ala Val Ala Gly Ser Thr Gly Ala
    210                 215                 220

Gly Lys Thr Ser Leu Leu Met Met Ile Met Gly Glu Leu Glu Pro Ser
225                 230                 235                 240

Glu Gly Lys Ile Lys His Ser Gly Arg Ile Ser Phe Cys Ser Gln Phe
                245                 250                 255

Ser Trp Ile Met Pro Gly Thr Ile Lys Glu Asn Ile Ile Phe Gly Val
            260                 265                 270

Ser Tyr Asp Glu Tyr Arg Tyr Arg Ser Val Ile Lys Ala Cys Gln Leu
        275                 280                 285

Glu Glu Asp Ile Ser Lys Phe Ala Glu Lys Asp Asn Ile Val Leu Gly
    290                 295                 300

Glu Gly Gly Ile Thr Leu Ser Gly Gly Gln Arg Ala Arg Ile Ser Leu
305                 310                 315                 320

Ala Arg Ala Val Tyr Lys Asp Ala Asp Leu Tyr Leu Leu Asp Ser Pro
                325                 330                 335

Phe Gly Tyr Leu Asp Val Leu Thr Glu Lys Glu Ile Phe Glu Ser Cys
            340                 345                 350

Val Cys Lys Leu Met Ala Asn Lys Thr Arg Ile Leu Val Thr Ser Lys
        355                 360                 365

Met Glu His Leu Lys Lys Ala Asp Lys Ile Leu Ile Leu Asn Glu Gly
    370                 375                 380

Ser Ser Tyr Phe Tyr Gly Thr Phe Ser Glu Leu Gln Asn Leu Gln Pro
385                 390                 395                 400

Asp Phe Ser Ser Lys Leu Met Gly Cys Asp Ser Phe Asp Gln Phe Ser
                405                 410                 415

Ala Glu Arg Arg Asn Ser Ile Leu Thr Glu Thr Leu His Arg Phe Ser
            420                 425                 430

Leu Glu Gly Asp Ala Pro Val Ser Trp Thr Glu Thr Lys Lys Gln Ser
        435                 440                 445

Phe Lys Gln Thr Gly Glu Phe Gly Glu Lys Arg Lys Asn Ser Ile Leu
    450                 455                 460

Asn Pro Ile Asn Ser Ile Arg Lys Phe Ser Ile Val Gln Lys Thr Pro
465                 470                 475                 480

Leu Gln Met Asn Gly Ile Glu Glu Asp Ser Asp Glu Pro Leu Glu Arg
                485                 490                 495
```

-continued

```
Arg Leu Ser Leu Val Pro Asp Ser Glu Gln Gly Glu Ala Ile Leu Pro
            500                 505                 510

Arg Ile Ser Val Ile Ser Thr Gly Pro Thr Leu Gln Ala Arg Arg Arg
        515                 520                 525

Gln Ser Val Leu Asn Leu Met Thr His Ser Val Asn Gln Gly Gln Asn
    530                 535                 540

Ile His Arg Lys Thr Thr Ala Ser Thr Arg Lys Val Ser Leu Ala Pro
545                 550                 555                 560

Gln Ala Asn Leu Thr Glu Leu Asp Ile Tyr Ser Arg Arg Leu Ser Gln
                565                 570                 575

Glu Thr Gly Leu Glu Ile Ser Glu Glu Ile Asn Glu Glu Asp Leu Lys
            580                 585                 590

Glu Cys Leu Phe Asp Asp Met Glu Ser Ile Pro Ala Val Thr Thr Trp
        595                 600                 605

Asn Thr Tyr Leu Arg Tyr Ile Thr Val His Lys Ser Leu Ile Phe Val
    610                 615                 620

Leu Ile Trp Cys Leu Val Ile Phe Leu Ala Glu Val Ala Ala Ser Leu
625                 630                 635                 640

Val Val Leu Trp Leu Leu Gly Asn Thr Pro Leu Gln Asp Lys Gly Asn
                645                 650                 655

Ser Thr His Ser Arg Asn Asn Ser Tyr Ala Val Ile Ile Thr Ser Thr
            660                 665                 670

Ser Ser Tyr Tyr Val Phe Tyr Ile Tyr Val Gly Val Ala Asp Thr Leu
        675                 680                 685

Leu Ala Met Gly Phe Phe Arg Gly Leu Pro Leu Val His Thr Leu Ile
    690                 695                 700

Thr Val Ser Lys Ile Leu His His Lys Met Leu His Ser Val Leu Gln
705                 710                 715                 720

Ala Pro Met Ser Thr Leu Asn Thr Leu Lys Ala Gly Gly Ile Leu Asn
                725                 730                 735

Arg Phe Ser Lys Asp Ile Ala Ile Leu Asp Asp Leu Leu Pro Leu Thr
            740                 745                 750

Ile Phe Asp Phe Ile Gln Leu Leu Leu Ile Val Ile Gly Ala Ile Ala
        755                 760                 765

Val Val Ala Val Leu Gln Pro Tyr Ile Phe Val Ala Thr Val Pro Val
    770                 775                 780

Ile Val Ala Phe Ile Met Leu Arg Ala Tyr Phe Leu Gln Thr Ser Gln
785                 790                 795                 800

Gln Leu Lys Gln Leu Glu Ser Glu Gly Arg Ser Pro Ile Phe Thr His
                805                 810                 815

Leu Val Thr Ser Leu Lys Gly Leu Trp Thr Leu Arg Ala Phe Gly Arg
            820                 825                 830

Gln Pro Tyr Phe Glu Thr Leu Phe His Lys Ala Leu Asn Leu His Thr
        835                 840                 845

Ala Asn Trp Phe Leu Tyr Leu Ser Thr Leu Arg Trp Phe Gln Met Arg
    850                 855                 860

Ile Glu Met Ile Phe Val Ile Phe Phe Ile Ala Val Thr Phe Ile Ser
865                 870                 875                 880

Ile Leu Thr Thr Gly Glu Gly Glu Gly Arg Val Gly Ile Ile Leu Thr
                885                 890                 895

Leu Ala Met Asn Ile Met Ser Thr Leu Gln Trp Ala Val Asn Ser Ser
            900                 905                 910

Ile Asp Val Asp Ser Leu Met Arg Ser Val Ser Arg Val Phe Lys Phe
        915                 920                 925
```

-continued

```
Ile Asp Met Pro Thr Glu Gly Lys Pro Thr Lys Ser Thr Lys Pro Tyr
    930                 935                 940

Lys Asn Gly Gln Leu Ser Lys Val Met Ile Ile Glu Asn Ser His Val
945                 950                 955                 960

Lys Lys Asp Asp Ile Trp Pro Ser Gly Gly Gln Met Thr Val Lys Asp
                965                 970                 975

Leu Thr Ala Lys Tyr Thr Glu Gly Gly Asn Ala Ile Leu Glu Asn Ile
            980                 985                 990

Ser Phe Ser Ile Ser Pro Gly Gln Arg Val Gly Leu Leu Gly Arg Thr
        995                 1000                1005

Gly Ser Gly Lys Ser Thr Leu Leu Ser Ala Phe Leu Arg Leu Leu Asn
   1010                1015                1020

Thr Glu Gly Glu Ile Gln Ile Asp Gly Val Ser Trp Asp Ser Ile Thr
1025                1030                1035                1040

Leu Gln Gln Trp Arg Lys Ala Phe Gly Val Ile Pro Gln Lys Val Phe
               1045                1050                1055

Ile Phe Ser Gly Thr Phe Arg Lys Asn Leu Asp Pro Tyr Glu Gln Trp
           1060                1065                1070

Ser Asp Gln Glu Ile Trp Lys Val Ala Asp Glu Val Gly Leu Arg Ser
       1075                1080                1085

Val Ile Glu Gln Phe Pro Gly Lys Leu Asp Phe Val Leu Val Asp Gly
   1090                1095                1100

Gly Cys Val Leu Ser His Gly His Lys Gln Leu Met Cys Leu Ala Arg
1105                1110                1115                1120

Ser Val Leu Ser Lys Ala Lys Ile Leu Leu Leu Asp Glu Pro Ser Ala
               1125                1130                1135

His Leu Asp Pro Val Thr Tyr Gln Ile Ile Arg Arg Thr Leu Lys Gln
           1140                1145                1150

Ala Phe Ala Asp Cys Thr Val Ile Leu Cys Glu His Arg Ile Glu Ala
       1155                1160                1165

Met Leu Glu Cys Gln Gln Phe Leu Val Ile Glu Glu Asn Lys Val Arg
   1170                1175                1180

Gln Tyr Asp Ser Ile Gln Lys Leu Leu Asn Glu Arg Ser Leu Phe Arg
1185                1190                1195                1200

Gln Ala Ile Ser Pro Ser Asp Arg Val Lys Leu Phe Pro His Arg Asn
               1205                1210                1215

Ser Ser Lys Cys Lys Ser Lys Pro Gln Ile Ala Ala Leu Lys Glu Glu
           1220                1225                1230

Thr Glu Glu Glu Val Gln Asp Thr Arg Leu
       1235                1240
```